US012761235B2

(12) United States Patent
Fusaro et al.

(10) Patent No.: US 12,761,235 B2
(45) Date of Patent: Oct. 13, 2026

(54) CONTAINER AND AUTOMATED ACCESSIONING AND ASSEMBLY PLATFORM

(71) Applicant: Laboratory Corporation of America Holdings, Burlington, NC (US)

(72) Inventors: Vincent Alfred Fusaro, San Francisco, CA (US); David John Guckenberger, Jr., Oakland, CA (US); Johnathan Carl Hoar Whittaker, San Francisco, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 435 days.

(21) Appl. No.: 18/288,134

(22) PCT Filed: Apr. 29, 2022

(86) PCT No.: PCT/US2022/026949
§ 371 (c)(1),
(2) Date: Oct. 24, 2023

(87) PCT Pub. No.: WO2022/232519
PCT Pub. Date: Nov. 3, 2022

(65) Prior Publication Data
US 2024/0210432 A1 Jun. 27, 2024

Related U.S. Application Data

(60) Provisional application No. 63/227,282, filed on Jul. 29, 2021, provisional application No. 63/219,255,
(Continued)

(51) Int. Cl.
*G01N 35/00* (2006.01)
*A61B 5/15* (2006.01)
(Continued)

(52) U.S. Cl.
CPC ....... *G01N 35/04* (2013.01); *A61B 5/150351* (2013.01); *A61B 5/150786* (2013.01);
(Continued)

(58) Field of Classification Search
CPC ............. G01N 35/04; G01N 35/00732; G01N 2035/00742; G01N 2035/0405;
(Continued)

(56) References Cited

U.S. PATENT DOCUMENTS

2004/0131499 A1* 7/2004 Okada .................. G01N 35/025 422/64
2015/0056716 A1 2/2015 Oyler et al.
(Continued)

OTHER PUBLICATIONS

International Search Report and Written Opinion mailed Aug. 29, 2022 for International Application No. PCT/US2022/026949.
(Continued)

*Primary Examiner* — Benjamin R Whatley
(74) *Attorney, Agent, or Firm* — Wolf, Greenfield & Sacks, P.C.

(57) ABSTRACT

An accessioning system is configured to retrieve sample vials from a container. An assembly system is configured to assemble a container containing a sample vial. The container includes a base and a cap, where the cap may have a larger longitudinal length than the base. The longitudinal length of the cap may form a majority of an overall length of the container. The container may include a watertight seal. The container may also include a hydrochromic indicator configured to indicate the present or past presence of a liquid, solution, or other substance inside an internal volume of the container.

17 Claims, 30 Drawing Sheets

Related U.S. Application Data filed on Jul. 7, 2021, provisional application No. 63/182,312, filed on Apr. 30, 2021.

(51) Int. Cl.

| | |
|---|---|
| ***B01L 9/06*** | (2006.01) |
| ***G01N 35/04*** | (2006.01) |
| *A61B 10/00* | (2006.01) |
| *B01L 3/00* | (2006.01) |

(52) U.S. Cl.

CPC .......... *B01L 9/06* (2013.01); *G01N 35/00732* (2013.01); *A61B 5/15003* (2013.01); *A61B 5/150343* (2013.01); *A61B 10/0045* (2013.01); *B01L 3/502* (2013.01); *B01L 3/50825* (2013.01); *B01L 2200/141* (2013.01); *B01L 2200/18* (2013.01); *B01L 2200/185* (2013.01); *B01L 2300/021* (2013.01); *B01L 2300/042* (2013.01); *B01L 2300/047* (2013.01); *B01L 2300/0609* (2013.01); *B01L 2300/0663* (2013.01); *B01L 2300/12* (2013.01); *G01N 2035/00742* (2013.01); *G01N 2035/0405* (2013.01)

(58) Field of Classification Search

CPC ........ A61B 5/150351; A61B 5/150786; A61B 5/15003; A61B 5/150343; A61B 10/0045; A61B 5/154; B01L 9/06; B01L 3/502; B01L 3/50825; B01L 2200/141; B01L 2200/18; B01L 2200/185; B01L 2300/021; B01L 2300/042; B01L 2300/047; B01L 2300/0609; B01L 2300/0663; B01L 2300/12; B01L 2200/025; B01L 2200/026; B01L 2200/04; B01L 2200/0689; B01L 2300/0627; B01L 2300/0832

See application file for complete search history.

(56) References Cited

U.S. PATENT DOCUMENTS

| | | | | |
|---|---|---|---|---|
| 2017/0042460 | A1* | 2/2017 | Holmes | A61B 5/150946 |
| 2019/0234980 | A1* | 8/2019 | Wilson | G01N 35/04 |
| 2019/0331703 | A1 | 10/2019 | Olson et al. | |
| 2019/0350808 | A1 | 11/2019 | Olson et al. | |
| 2020/0022684 | A1* | 1/2020 | Sessions | A61B 10/0045 |
| 2020/0094248 | A1 | 3/2020 | Picart et al. | |
| 2020/0101464 | A1* | 4/2020 | Fujii | G01N 35/026 |
| 2020/0156056 | A1 | 5/2020 | Williams et al. | |
| 2021/0011039 | A1* | 1/2021 | Masutani | B01L 9/06 |

OTHER PUBLICATIONS

International Preliminary Report on Patentability mailed Nov. 9, 2023 for International Application No. PCT/US2022/026949.

* cited by examiner

CONTAINER AND AUTOMATED ACCESSIONING AND ASSEMBLY PLATFORM

RELATED APPLICATIONS

This application is a national stage filing under 35 U.S.C. § 371 of International Application Ser. No. PCT/US2022/026949, filed Apr. 29, 2022, which claims the benefit of priority under 35 U.S.C. § 119(e) to U.S. Provisional Application Ser. No. 63/182,312, filed Apr. 30, 2021, U.S. Provisional Application Ser. No. 63/219,255, filed Jul. 7, 2021, and U.S. Provisional Application Ser. No. 63/227,282, filed Jul. 29, 2021, each of which is incorporated herein by reference in its entirety.

FIELD

Disclosed embodiments are related to containers, automated container accessioning platforms, automated container assembly platforms, and related methods of use.

BACKGROUND

Sample vials including liquid samples of biological compounds are frequently sent through ecommerce channels which have continued to expand over the recent years. In recent times, there has been a particular emphasis on contactless delivery and taking of sample for a wide variety of diagnostic tests ranging from DNA tests to COVID-19 tests. Currently, samples are shipped in multiple containers which are layered to reduce chances of a sample being inadvertently released. For example, in some instances a sample container is placed inside of a sealed bag, inside of a box, inside of another bag before the sample container is suitable for shipping through standard ecommerce package delivery channels.

SUMMARY

In some embodiments, a container includes a base including a base internal volume, where the base has a base longitudinal length; a cap configured to removably couple to the base, where the cap includes a cap internal volume and an external cap key, the external cap key configured to engage with a gripper of a decapper for removal of the cap off of the base, where the cap internal volume is greater than the base internal volume, and where the cap has a cap longitudinal length, and where the cap longitudinal length is greater than the base longitudinal length.

In some embodiments, a container includes a base including a base internal volume and a base key, a cap configured to receive and removably couple to the base, where the cap includes a cap internal volume and a cap key, and a closure configured to couple the base to the cap, where the closure includes a radial projection and a channel configured to receive the radial projection, where the channel terminates in a closed end. The closure further includes a protrusion, the protrusion being spaced from the closed end, where sliding of the radial projection past the protrusion produces a click, and where the base and the cap mate together to form a watertight seal.

In some embodiments, a container includes a base having a base internal volume and an external base key, a cap configured to receive and removably couple to the base, where the cap includes a cap internal volume and an external cap key, and a closure configured to couple the base to the cap. The closure forms a watertight seal when the base is coupled to the cap, where the base internal volume and the cap internal volume combine to form an internal volume when the base is coupled to the cap, and where the internal volume is configured to receive and enclose a sample vial.

In some embodiments, a method of detecting leakage of a sample vial inside of a container, where the container includes a base and a cap, and where at least a portion of the container is translucent, includes imaging an internal volume of the container through a wall of the container with an imaging sensor, where the internal volume contains the sample vial, and detecting, based on the imaging, a state of a hydrochromic indicator disposed inside of the internal volume, where the hydrochromic indicator has a first state in which the hydrochromic indicator is a first color, and where the hydrochromic indicator has a second state in which the hydrochromic indicator is a second color, where exposing the hydrochromic indicator to liquid, substance, or other solution causes the hydrochromic indicator to change from the first state to the second state. The method further includes upon detecting the first state of the hydrochromic indicator, removing the cap from the base with a gripper, and upon detecting the second state of the hydrochromic indicator, allowing the cap to remain on the base.

In some embodiments, a method of removing a sample vial from a container, where the container includes a base and a cap, where the cap has a cap longitudinal length and the base has a base longitudinal length, the cap longitudinal length being greater than the base longitudinal length, where the sample vial has a vial longitudinal length greater than the base longitudinal length, includes removing the cap from the base to expose the sample vial, the sample vial being supported by the base, imaging a portion of the sample vial with an imaging sensor, determining an orientation state of the sample vial, where the sample vial has an upright orientation where a vial cap of the sample vial is above a bottom portion of the sample vial, and where the sample vial has an inverted orientation where the bottom portion of the sample vial is above the vial cap, grasping the sample vial with a first gripper, lifting the sample vial out of the base with the first gripper, and upon detecting the inverted orientation, rotating the sample vial from the inverted orientation to the upright orientation.

In some embodiments, a container retrieval system for retrieving sample vials from containers, the containers including a container including a base, a cap, an internal volume, the internal volume having both a hydrochromic indicator and a sample vial disposed therein, includes a conveyor configured to support and move the container, an imaging sensor configured to obtain an image of the hydrochromic indicator through a wall of the container for detecting a state of the hydrochromic indicator, where at least a part of the wall is translucent, and a processor. The processor is configured to obtain the image of the hydrochromic indicator obtained by the imaging sensor, detect, by processing the image, the state of the hydrochromic indicator, and determine, based on the detected state of the hydrochromic indicator, whether the hydrochromic indicator was exposed to liquid, substance, or other solution.

In some embodiments, a system for retrieving a sample vial from a container, the container including a base, a cap, and an internal volume, and a sample vial disposed in the internal volume, includes a conveyor configured to support and move the container by the base, where the conveyor inhibits rotation of the base, a first gripper configured to remove the cap from the base by rotating the cap relative to the base, an imaging sensor configured to determine an orientation state of the sample vial, where the sample vial has an upright orientation where a vial cap of the sample vial is above a bottom portion of the sample vial, and where the sample vial has an inverted orientation where the bottom portion of the sample vial is above the vial cap, and a second gripper configured to grasp the sample vial and lift the sample vial out of the base, and where the second gripper is configured to rotate the sample vial from the inverted orientation to the upright orientation.

In some embodiments, a system for retrieving sample vials from a plurality of containers, each container of the plurality of containers including a base, a cap, and an internal volume, and a sample vial disposed in the internal volume, includes a hopper configured to receive the plurality of containers, a receiver configured to receive a first container from the hopper, where the receiver is configured to orient the first container in a first orientation, where in the first orientation the cap is positioned above the base, a conveyor configured to receive the first container from the receiver, where the conveyor is configured to support and move the first container by the base, where the conveyor inhibits rotation of the base, and a first gripper configured to remove the cap from the base by rotating the cap relative to the base.

In some embodiments, a method of removing sample vials from a plurality of containers, where each container of the plurality of containers includes a base and a cap, where the cap has a cap longitudinal length and the base has a base longitudinal length, the cap longitudinal length being greater than the base longitudinal length, where the sample vials have a vial longitudinal length greater than the base longitudinal length, includes placing the plurality of containers in a hopper, transferring a first container of the plurality of containers from the hopper to a receiver, orienting the first container to a first orientation where the cap is positioned above the base with the receiver, transferring the first container to a conveyor, where the conveyor supports the first container by the base, where the conveyor inhibits rotation of the base, and removing the cap from the base to expose a sample vial disposed in the first container, the sample vial being supported by the base.

In some embodiments, a method of assembling a container, where the container includes a base and a cap, includes placing a sample vial in the base with an automated assembly system, placing the cap on the base with the automated assembly system, and rotating the cap relative to the base with the automated assembly system to couple the cap to the base.

In some embodiments, a method of assembling a container, where the container includes a base and a cap, includes placing an object in the base with an automated assembly system, placing the cap on the base with the automated assembly system, and rotating the cap relative to the base with the automated assembly system to couple the cap to the base. Rotating the cap relative to the base includes engaging an external base key with a base receptacle and engaging an external cap key with a gripper.

In some embodiments, a system for retrieving sample vials from a plurality of containers, each container of the plurality of containers comprising a base, a cap, and an internal volume, and a sample vial disposed in the internal volume, includes a conveyor configured to receive and move the plurality of containers, at least one imaging sensor configured to observe at least one characteristic of each container of the plurality of containers disposed on the conveyor, a first gripper configured to remove a container of the plurality of containers from the conveyor, a hopper configured to receive the plurality of containers from the conveyor, wherein the hopper is configured to vibrate containers disposed in the hopper, and a second gripper configured to remove a container of the plurality of containers from the hopper.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1A:
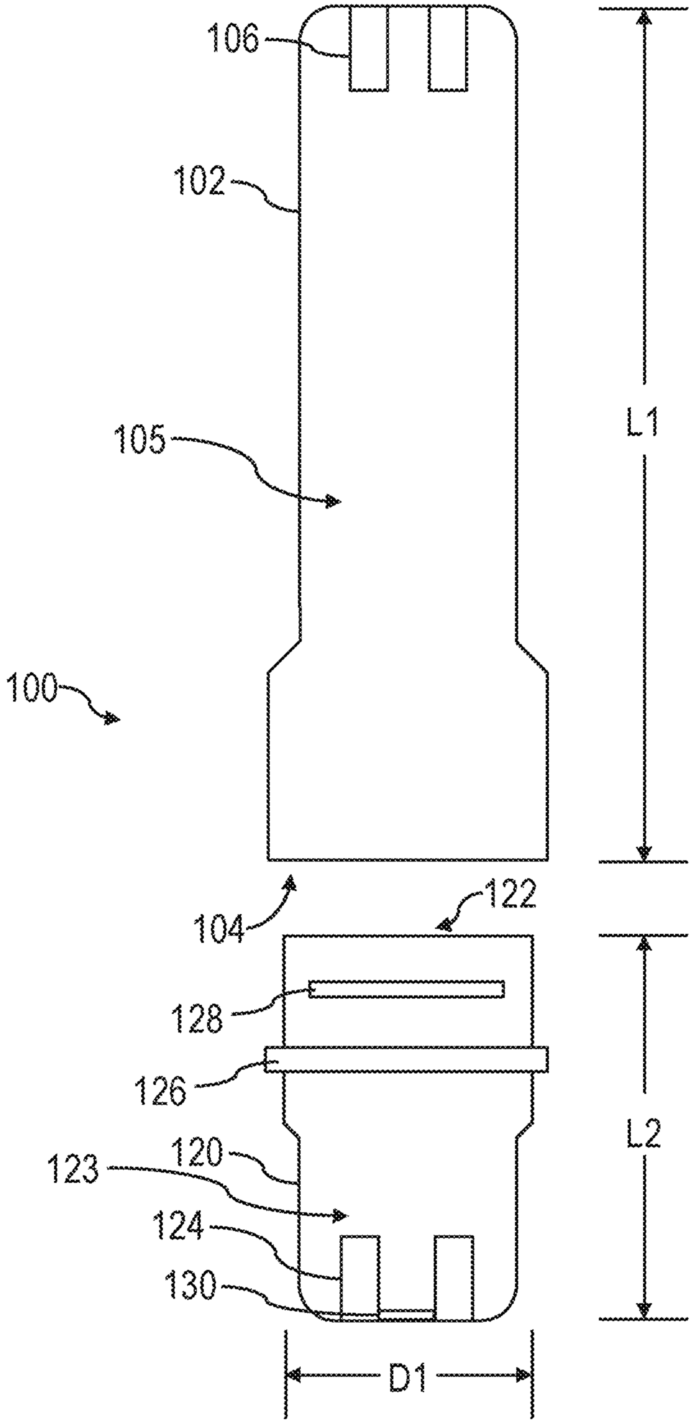
FIG. 1A is a side schematic of one embodiment of a container in an empty state.

Sample vials including liquid samples of biological compounds are frequently sent through ecommerce channels which have continued to expand over the recent years. In recent times, there has been a particular emphasis on contactless delivery and taking of samples for a wide variety of diagnostic tests ranging from DNA tests to COVID-19 tests. Currently, samples are shipped in multiple containers which are layered to reduce chances of a sample being inadvertently released. For example, in some instances a liquid-tight sample vial is placed inside of a sealed bag, inside of a box, inside of another bag before the sample container is suitable for shipping through standard ecommerce package delivery channels. Such an arrangement makes automated accessioning of the sample vials difficult and complex, as the bags and boxes are difficult for robotic systems to open and manipulate. Accordingly, conventionally sample vials are manually retrieved from such packaging by workers, which is a slow, time-consuming, and expensive process.

In view of the above, the inventors have recognized the benefits of an automated accessioning platform that employs a rigid container for holding a sample vial, and a container accessioning system that simplifies the accessioning of the sample vial from the container. The container includes rigid dimensions that are detectable by a variety of sensors making the container well suited for manipulation by robotic system. The container may be configured to contain a sample vial without any additional soft packaging or bags that may interfere with an automated accessioning process. In some embodiments, the container may be shipped through traditional channels without additional rigid packaging (e.g., boxes) that may interfere with an automated accessioning process. The container may be configured to allow the accessioning system to access and extract a sample vial from the container with a gripper. The container may be configured such that a wide variety of sample vial sizes may be accommodated and extracted from a single size of container. The container may include a closure configured to allow relative rotation between a cap and a base of the container in a first direction to close the container, and in a second direction to open the container. The container may be watertight, such that any leakage of sample vials is contained within the container.

In some embodiments, a container includes a cap and a base. The base includes a base internal volume and has a base longitudinal length. The cap includes a cap internal volume and a cap longitudinal length. The cap and the base are configured to removably couple together to create a combined internal volume formed by the cap internal volume and the base internal volume. In particular, the cap includes an external cap key configured to engage with a gripper of a decapper of an accessioning system such that the gripper may selectively remove the cap off of the base. In some embodiments, the external cap key is configured to engage the gripper to transmit torque between the cap and the gripper. The container is configured to receive and enclose a sample vial in the internal volume, where the sample vial is supported by the base. The base longitudinal length is configured such that a variety of sample vials of different lengths protrude out of the base and are accessible to a gripper of an accessioning system. The cap longitudinal length is greater than that of the base longitudinal length, such that sample vials having a variety of lengths may be accommodated in the internal volume. Correspondingly, the cap internal volume may also be greater than the base internal volume. In some embodiments, the cap longitudinal length may be 2 to 4 times greater than the base longitudinal length. Such an arrangement may allow the base to support both short and long sample vials, allowing both sizes to protrude out of the base for extraction by a gripper of an accessioning system.

As used herein, a "base" refers to a bottom portion of the container, which is configured to support a sample vial against the force of gravity. The base of a container may be configured to be received in a conveyor and may be held in the conveyor by force of gravity. A "cap" refers to an upper portion of a container, which is configured to be removed to reveal the sample vial. Together the cap and the base may form an internal volume that accommodates the sample vial.

According to exemplary embodiments described herein, a cap of a container may include an external cap key. The external cap key may be configured to allow a gripper of a decapper to interface with the cap such that force may be applied to remove the cap from a base. In some embodiments, the external cap key may be configured to allow torque transmission between the gripper and the cap, such that the gripper may rotate the cap. For example, the external cap key may include one or more flats, notches, protrusions, and/or any features alone or in combination that form a torque transmitting interface between the gripper and the cap. In some embodiments, the external cap key may be configured to allow longitudinal force transmission between the cap and the gripper. In some embodiments, the base of a container may include an external base key. Similar to the external cap key, the external base key may be configured to allow force transmission between the base and a conveyor of an accessioning system. In some embodiments, the external base key may be configured to allow torque transmission between the base and the conveyor, such that the conveyor may resist rotation of the base. According to such embodiments, the conveyor may resist rotation of the base while a gripper applies torque to the cap, thereby allowing relative rotation between the cap and the base such that the cap may be removed from the base. In some embodiments, the external base key may include one or more flats, notches, protrusions, and/or any other features alone or in combination that form a torque transmitting interface between the conveyor and the base.

According to exemplary embodiments described herein, a container may include a closure configured to couple the base to the cap. In some embodiments, the closure may be configured to form a watertight seal between the cap and the base when the cap and the base mate together. In some embodiments, the watertight seal may be formed by a compliant gasket, threads, or any other suitable watertight seal. In some embodiments, a closure may be a rotary closure. That is, the closure may allow the cap and the base to be coupled to one another via relative rotation of the cap and the base. For example, in some embodiments, the closure may include threads. As another example, in some embodiments the closure may include a projection and a channel. The channel may be configured to receive the projection, where rotation of the base relative to the cap while the radial projection is disposed in the channel is configured to couple the base and the cap and form a watertight seal. In some embodiments, the channel may be disposed on the cap and the base includes the projection. In other embodiments, the channel may be disposed on the base and the cap includes the projection. In some embodiments, when the radial projection is received in the channel, relative rotation of the base and the cap moves the base closer to the cap.

The inventors have also appreciated the benefits of a container including an indicator configured to provide an external indication of the past or current presence of a liquid, solution, or other substance inside an internal volume of the container (e.g., due to a leak from the sample vial). In such embodiments, the indicator may be configured to alert the accessioning system or a user to the past or current presence of a liquid, solution, or other substance inside an internal volume of the container, thereby allowing the container to be easily quarantined for cleanup and/or further processing.

In some embodiments, a container may include a hydrochromic indicator configured to indicate the past or current presence of a liquid, solution, or other substance in an internal volume of the container. The hydrochromic indicator may be configured to irreversibly change state (e.g., color) when exposed to liquid, a solution, or other substance. In some embodiments, the hydrochromic indicator includes a desiccant to absorb the liquid, solution, or other substance. In some embodiments, the hydrochromic indicator may have a first state in which the hydrochromic indicator is a first color, and a second state in which the hydrochromic indicator is a second color. Exposing the hydrochromic indicator to liquid may cause the hydrochromic indicator to change from the first state to the second state. The hydrochromic indicator may be a hydrochromic dye, a hydrochromic coating disposed on an inner wall of the container, and/or a liquid contact indicator. In some embodiments, the hydrochromic indicator may be configured to create a visible change in pattern, opacity, and/or color when exposed to liquid. In some embodiments, hydrochromic indicator may reveal a symbol or text when exposed to liquid. The hydrochromic indicator may be visible form a location external to the container. In some embodiments, at least a portion of a wall of a container (e.g., on a cap or base) may be translucent or may otherwise include a window configured to allow the hydrochromic indicator to be optically observed and detected externally (e.g., by an imaging sensor). In some embodiments, the entire cap of the container may be translucent. In some embodiments, at least a portion of the container may be formed out of a hydrochromic material and may thus function as a hydrochromic indicator. For example, the portion of the container formed out of a hydrochromic material may be extend from the internal volume of the container to an external surface of the container such that the portion of the container changes color or otherwise indicates when the liquid is disposed in the internal volume from the sample vial, and the color change or indication is visible from outside of the internal volume of the container. For example, a wall of the container, including the internal and external surfaces of the wall, may change color when liquid is disposed in the internal volume of the container, such that the color change is visible from outside of the container.

In some embodiments, an accessioning system may be configured to detect the state of a hydrochromic indicator and perform an action depending on the state of the hydrochromic indicator. In some embodiments, the accessioning system may include an imaging sensor configured to image a sealed container, where a cap of the container is coupled to the base of the container. Imaging the sealed container may include imaging the hydrochromic indicator. In some embodiments, imaging the sealed container may include imaging an internal volume of the container through the wall of the container, where the wall may be translucent. A processor of the accessioning system receiving information from the imaging sensor may determine whether the hydrochromic indicator is in a first state or a second state. The determination of the first state and second state may be based on differences in color, pattern, opacity of the wall, and/or the presence of a specific symbol or text. Upon detecting the first state of the hydrochromic indicator, which may be associated with no liquid disposed in the internal volume, the cap of the container may be removed from the base. Upon detecting the second state of the hydrochromic indicator, which may be associated with the past or current presence of a liquid, solution, or other substance in the internal volume, the cap may be allowed to remain on the base. The container having a hydrochromic indicator in the second state may be removed from the accessioning system and placed in a quarantine receptacle. In this manner, the accessioning system may avoid opening containers in which there may be spilled samples or other contamination. Accordingly, these containers may be separated for separate processing and cleaning, while allowing containers without leakage to continue through the accessioning system. In some embodiments, the processor may be configured to update a status of the container in a database based on the detected state of the hydrochromic indicator.

In some embodiments, where at least a portion of a container is transparent and an accessioning system includes an imaging sensor configured to image an internal volume of the container, the imaging sensor may observe a sample vial disposed in the internal volume directly. In some embodiments, an accessioning system may determine a status of the sample vial based on the images from the imaging sensor (e.g., by software executing on one or more computing devices, such as a computer having the processor configured to execute the software). In some embodiments, the accessioning system may determine a status of the sample vial, including, but not limited to, the presence of a sample vial cap, the presence of a crack or defect in the sample vial (e.g., detecting a crack in glass or plastic), and leakage of biological specimen that is not strictly liquid.

In some embodiments, a container may include a desiccant configured to at least partially absorb liquid disposed in an internal volume of the container. Such an arrangement may assist in cleanup of accidental leakage inside the internal volume. In some embodiments, the desiccant may be removably retained in the internal volume with one or more tabs. For example, in some embodiments, the desiccant may be retained adjacent a top portion of the cap by one or more tabs. In some embodiments, a hydrochromic indicator may be configured to irreversibly change color when exposed to liquid, such that even if liquid in the internal volume is absorbed by the desiccant, the hydrochromic indicator may still indicate past leakage inside the container. In some embodiments, the desiccant may include the hydrochromic indicator. In some embodiments, the hydrochromic indicator may include the desiccant. In some embodiments, the desiccant and the hydrochromic indicator are combined to create an absorbent device capable of absorbing liquid and changing color when coming into contact with a liquid, solution, or other substance.

In addition to the above, the inventors have recognized the benefits of an accessioning system configured to retrieve sample vials from containers according to exemplary embodiments described herein. The accessioning system may be configured to decouple a cap from a base of a container. The accessioning system may include a hopper configured to receive a plurality of containers in bulk. The hopper may feed containers sequentially to a conveyor, which is configured to receive and support the base of each container. In some embodiments, the hopper and/or receiver may orient each container in an upright orientation such that the base may be reliably received by the conveyor. In some embodiments, such orienting may include flipping or rotating a container having an incorrect orientation. The accessioning system may also include a decapper configured to engage the cap of each container and remove the cap from the base. As discussed previously, in some embodiments, removing the cap from the container may include rotating the cap relative to the base and/or applying longitudinal force to the cap to remove the cap from the base. Once the cap is removed, a sample vial supported by the base may be exposed. The accessioning system may also include a gripper configured to grasp the sample vial and remove the sample vial from the base.

In some embodiments, the accessioning system may include an imaging sensor configured to read an identification marker disposed on an exterior surface of the base of a container. The identification marker may include information related to the container and/or sample vial including type of sample, age of sample, age of the subject from which the sample was obtained, manufacturing information, etc. The imaging sensor may be configured to provide the information to a processor. The processor may be configured to update a status of the container in a database based on the information. In some embodiments, the identification marker may be a QR code, barcode, or other symbol configured to convey information. The imaging sensor may be a camera, barcode reader, and/or other imaging sensor configured to retrieve the information. In some embodiments, depending on the identification marker, the processor may flag the container for prioritized accession. In some embodiments, reading the identification marker may allow the processor to determine whether the container is in an upright orientation. In such an embodiment, the identification marker may be read prior to placing the container in a conveyor, such that the reading of the identification marker ensures the base of the container is ready to be received in the conveyor. In some embodiments, the processor may employ the information obtained by the imaging system to index a particular container on a conveyor. Accordingly, the accessioning system may store a position of the container on the conveyor based on the reading of the identification marker.

In some embodiments, a portion of a container may be color coded with a color which corresponds to a type of sample vial. For example, in some embodiments, a cap of a container may be color coded with a first color which is configured to be employed when the container holds a sample vial of a first type. In a corresponding example, the cap of the container may be color coded with a second color which is configured to be employed when the container holds a sample vial of a second type. In this manner, the type of contents of a sample vial held within a container may be determined visually based on the color of the portion of a container (e.g., the cap). Of course, in other embodiments, a base of a container may be colored according to a sample vial type, as the present disclosure is not so limited. In some embodiments, the cap and/or base may be color coded by forming the cap and/or base of a material having that color.

In some embodiments, a particular color of a container cap or container base may be provided to a user with a corresponding sample vial, such that the match between the color and sample vial type is ensured. In some embodiments, the color of the portion of the container may be detected by a camera or other imaging sensor of an automated accessioning system. In some embodiments, depending on the color of the portion of the container, a processor may flag the container for prioritized accession. In some embodiments, the processor may employ the information obtained by the imaging sensor to index a particular container on a conveyor. Accordingly, an accessioning system may store a position of the container on the conveyor based on the detection of a particular color. Such an arrangement may ensure that a sample vial retrieved from the container is sorted to an appropriate location based on the type of the sample vial. In some embodiments, an automated accessioning system may store containers having a particular color for accession at a certain point in time. In some such embodiments, the accessioning system may be configured to process containers having a particular color in series. For example, an accessioning system may first access green-colored containers that correspond to a type of sample (e.g., a blood sample) in series. In another example, the accessioning system may then access purple-colored containers that correspond to another type of sample (e.g., a stool sample) after the green-colored containers are accessed. Such an arrangement may simplify sorting and processing of containers containing different types of samples. Of course, an automated accessioning system may access containers in any desired order, as the present disclosure is not so limited.

In some embodiments, a QR code, barcode, or other symbol may be included on a container provided to the user. In such embodiments, the QR code, barcode or other symbol is employed by an automated accessioning system to assist in managing accession. In some embodiments, the barcode of the container may be detected by a camera or other sensor (e.g., imaging sensor) of an automated accessioning system. In some embodiments, depending on the information accessible based on the barcode, a processor may flag the container for prioritized accession. In some embodiments, the barcode itself may include information regarding a contained sample (e.g., sample type), age of the sample, or patient identification information that may be employed to prioritize certain containers. For example, samples of a type that may expire sooner may be prioritized for accession over samples that have longer remaining viability. In some embodiments, the barcode may be employed to lookup information in a database, such as a laboratory information management system (LIMS). In some embodiments, the barcode may be associated with metadata that is specific to order information associated with the particular container. For example, the metadata specific to the order information can include the type of sample associated with the order, patient information associated with the order, the type of assay associated with the order, the type of container associated with the order, etc. In some embodiments, the processor may employ the information associated with the detected barcode to index a particular container on a conveyor. Accordingly, an accessioning system may store a position of the container on the conveyor based on information associated with the barcode. Such an arrangement may ensure that a sample vial retrieved from the container is sorted to an appropriate location based on the type of the sample vial or other information associated with the barcode. In some embodiments, an automated accessioning system may store containers having a particular type (as determined based on information associated with the barcode) for accession at a certain point in time. In some such embodiments, the accessioning system may be configured to process containers having a particular type in series. For example, an accessioning system may first access containers that correspond to a type of sample (e.g., a blood sample) in series. In another example, the accessioning system may then access containers that correspond to another type of sample (e.g., a stool sample) after the first type of containers are accessioned. Such an arrangement may simplify sorting and processing of containers containing different types of samples. An automated accessioning system may access containers in any desired order based on any information associated with a barcode, as the present disclosure is not so limited.

In some embodiments, an accessioning system may include a gripper configured to grasp a sample vial disposed in a base of a container after a cap of the container has been removed. In such an embodiment, the gripper may be configured to grasp the sample vial and lift the sample vial out of the base. The sample vial may be in one of two orientations while supported by the base. In some cases, the sample vial may be in an upright orientation where a sample vial cap is above a sample vial body (e.g., a bottom portion of the sample vial). In other cases, the sample vial may be in an inverted orientation where a sample vial cap is below a sample vial body (e.g., a bottom portion of the sample vial). In some embodiments, in order to compensate for these differences in orientation, the accessioning system may include an imaging sensor configured to determine an orientation state of the sample vial. The imaging sensor may provide orientation information to a processor, which may determine the orientation of the sample vial via machine vision or detection of a particular marker (e.g., the visibility of the sample vial cap). Upon detecting the sample vial is in the inverted orientation, the processor may cause (e.g., instruct or command) the gripper to lift and rotate the sample vial from the inverted orientation to the upright orientation. Upon detecting that the sample vial is in the upright orientation, the processor may command the gripper to lift the sample vial from the base without rotating the sample vial.

In some embodiments, the accessioning system may include a second gripper configured to grasp the sample vial and to remove the sample vial from the gripper. As discussed previously, in some embodiments, a plurality of containers may contain a plurality of sample vials having different dimensions including length. Accordingly, in such embodiments, the accessioning system may include a height sensor configured to detect the height of a sample vial while held by the gripper. The height sensor may provide height information to the processor, which may cause (e.g., instruct or command) the second gripper to grip the sample vial at a predetermined distance from a sample vial cap. Accordingly, the height sensor may allow the second gripper to grip a wide variety of sample vials at an appropriate location on the sample vial based on the height information from the height sensor.

According to exemplary embodiments described herein, an accessioning system may be operated by one or more processors. The one or more processors may be configured to execute computer readable instructions stored in volatile or non-volatile memory. The one or more processors may communicate with one or more actuators associated with various elements of the accessioning system (e.g., receiver, conveyor, grippers, hopper, etc.) to control movement of the various elements. The one or more processors may receive information from one or more sensors that provide feedback regarding the various elements of the accessioning system. For example, the one or more processors may receive position information regarding a conveyor or gripper. In this manner, the machine controller may implement proportional control, integral control, derivative control, or a combination thereof (e.g., PID control). Other feedback control schemes are also contemplated, and the present disclosure is not limited in this regard. Any suitable sensors in any desirable quantities may be employed to provide feedback information to the one or more processors. Accelerometers, rotary encoders, potentiometers, imaging sensors (e.g., cameras), and height sensors may be employed in coordination with desirable processing techniques (e.g., machine vision). The one or more processors may also communicate with other controllers, computers, and/or processors on a local area network, wide area network, or internet using an appropriate wireless or wired communication protocol. In some embodiments, a processor may execute computer readable instructions based at least in part on input from a user. For example, a processor may receive input including a series of actions to be executed by the accessioning system. The one or more processors may execute the instructions based at least partly on the input to access the contents of one or more containers. It should be noted that while exemplary embodiments described herein are described with reference to a single processor, any suitable number of processors may be employed as a part of an accessioning system, as the present disclosure is not so limited.

The inventors have also recognized the benefits of a reusable rigid container for transportation of one or more different types of sample vials. In many instances, conventional shipping materials for sample vials are single use, meaning that any boxes and/or bags employed may be destroyed or otherwise discarded after use. The inventors have appreciated that containers according to exemplary embodiments described herein may be reused multiple times as they may be cleaned (e.g., cleaned, sanitized, disinfected and/or sterilized) between uses. In some embodiments, conventional boxes or bags may be employed to ship containers of exemplary embodiments described herein, as the present disclosure is not so limited. In some such embodiments, a label (e.g., barcode) or other identifier in a box or bag (e.g., RFID) may be employed to assist with sorting and tracking a container, as well as updating a database, according to exemplary embodiments described herein.

In some embodiments, an automated accessioning system may be configured to remove a cap of a container from a base of the container to access a sample vial held within the container. Once the sample vial is accessed, the caps may be moved (e.g., by a gripper) to a cap rack for storage and/or further processing, while the bases may be moved (e.g., by a gripper) to a base rack for storage and further processing. In some embodiments, the caps and bases may be cleaned (e.g., cleaned, sanitized, disinfected and/or sterilized), e.g., for re-use or for removal of biohazards prior to discarding.

In some embodiments, the caps and/or bases may be cleaned via any suitable process, e.g., a UV, chemical, autoclave, dry heat, radiation, etc. In some embodiments, the cap rack and/or base rack may be autoclavable racks, such that a cap rack and/or base rack containing a plurality of caps and/or bases, respectively, may be placed into an autoclave to sterilize the plurality of caps and/or bases.

In some embodiments, a particular cap and particular base may be interchanged with other caps and/or bases for reuse. That is, a particular cap may not need to be reused with the same base with which it was used previously. According to some such embodiments, an automated accessioning system may not sort and index individual caps and racks on a cap rack and/or base rack.

In some embodiments, a cap and/or rack may include a unique manufacture identifier (e.g., barcode, QR code, RFID tag, or other form of label) that may allow tracking of an individual cap and/or base. In some embodiments, the manufacture identifier may be read by a camera, barcode reader, other imaging sensor, and/or RFID reader. In some embodiments, a manufacture identifier may be employed to track how many times a cap and/or base has passed through an automated accessioning system. Such tracking may allow a cap and/or base to be retired after a certain number of uses, and/or such tracking may be employed to track wear or general usage of caps and bases. In some embodiments, the manufacture identifier may be an identification marker disposed on a cap and/or base, as described according to other exemplary embodiments described herein. According to such embodiments, an identification marker may be employed to convey information regarding the container, sample vial, manufacturing information, and/or the cap or base on which the identification marker is disposed. Of course, in other embodiments, the manufacture identifier may be distinct from an identification marker. In some embodiments, a manufacture identifier may be etched, laser engraved, or otherwise physically formed on a portion of a cap or base. In some such embodiments, the manufacture identifier may be updated when the cap or base passes through an automated accessioning system. For example, the manufacture identifier may include a number of markings equal to the number of times the cap or base has been through an accessioning system, where the accessioning system adds a marking when the cap or base passes through the accessioning system. In some alternative embodiments, the manufacture identifier may be updated after a certain number of cycles through an accessioning system. For example, the manufacture identifier may be updated every other time through an accessioning system, every five times through an accessioning system, or any other desired number, as the present disclosure is not so limited.

The inventors have also recognized the benefits of a container including a shipping identifier disposed on a portion of a container according to exemplary embodiments described herein. In some cases, as discussed above, a container according to exemplary embodiments described herein may be employed to ship a sample vial through traditional channels without other soft and/or rigid packaging (e.g., boxes, bags, etc.). That is, a container according to exemplary embodiments described herein may replace a combination of boxes and bags that are currently employed to ship sample vials. Accordingly, in some embodiments, a shipping identifier may be disposed on a portion of a container (e.g., an exterior portion) and may be employed to retrieve shipping related information. The shipping identifier may be a barcode, QR code, RFID tag, or other form of label that may convey information regarding the destination of the container, source of the container, sender information, recipient information, and/or contents of a sample vial disposed in the container. In some embodiments, the shipping identifier may be read by a camera, barcode reader, other imaging sensor, and/or RFID reader, which may retrieve information conveyed by the shipping identifier. In some embodiments, the shipping identifier may be an identification marker, as described according to other exemplary embodiments herein. In some embodiments, the shipping identifier may be a manufacture identifier, as described according to other exemplary embodiments herein. In some embodiments, an identification marker may function as both a shipping identifier and a manufacture identifier, as the present disclosure is not so limited. In some embodiments, a container may include a company label and may have suitable dimensions to meet preferences of a shipping provider.

The inventors have also recognized the benefits of a container that includes environmental control for a sample vial contained within the container. In some cases, particular samples may be susceptible to temperature variations or should be maintained at certain environmental conditions. Accordingly, in some embodiments, a container may include a cold pack, ice pack, hot pack, or other suitable chemically activated or passive environmental control. The environmental control may be activated in any suitable way—for example, the environmental control may be activated automatically without user intervention, or may be activated by the user.

In some embodiments, an environmental control may be releasably retained within an internal volume of a container (e.g., with one or more tabs). In some embodiments, an environmental control may be integrated into a portion of a container. For example, refrigerant gel may be disposed in a refrigerant volume formed in a container, such that the container may be frozen before use and the refrigerant gel may maintain the temperature of an internal volume of the container. In some embodiments, an environmental control may be chemically activated when a user seals a container. For example, in some embodiments, sealing a container may apply pressure to an environmental control (e.g., instant hot or cold pack) such that a chemical reaction is initiated in the environmental control. Such an arrangement may ensure that an environmental control maintains environmental conditions inside of an internal volume of the container for as long as possible.

The inventors have also recognized the benefits of an automated container assembly system. The automated container assembly system may be configured to prepare a container and related object for shipping or delivery to a user prior to use of the object by the user. In some embodiments, the automated container assembly system may include one or more grippers configured to place objects (e.g., a sample vial, hydrochromic indicator, environmental control, sample collecting components such as a swab, etc.) inside of a container. The automated container assembly system may also be configured to couple a cap to a base, such that the one or more objects placed in the base are captured in an internal volume of the container. Coupling the cap to the base may include rotating the cap relative to the base with a gripper and/or applying a longitudinal force to the cap in a direction of the base with a gripper. In some embodiments, the automated container assembly system may include an imaging sensor configured to image the container after the container is closed. In some embodiments, a processor may be configured to determine whether the container is closed based on the image from the imaging sensor. If the container is closed, the processor may allow the container to continue on the automated container assembly system to be shipped or otherwise delivered to a user. If the container is not closed, the processor may cause (e.g., instruct or control) the automated container assembly system to move the container to a separate area for further processing. In some embodiments, the processor may cause (e.g., control or instruct) the automated container assembly system to attempt to recouple the cap to the base if the container is not closed (e.g., with a gripper). In this manner, the automated container assembly system may prepare a container including the base materials for collecting a sample from an end user in an automated manner. In other embodiments, the automated container assembly system may be employed to assemble containers containing other objects, as the present disclosure is not so limited in this regard.

Containers according to exemplary embodiments described herein may be employed for a wide range of sample vials. Sample vials may include, but are not limited to, blood sample vials, saliva sample vials, urine sample vials, stool sample vials, and nasal mucus sample vials. Accordingly, containers according to exemplary embodiments described herein may be employed with any suitable type of sample vial, as the present disclosure is not so limited.

It should be noted that while exemplary dimensions are discussed herein with reference to some embodiments, alternative dimensions are contemplated. Accordingly, specific dimensions are not limiting and specific dimensions of a container according to exemplary embodiments described herein may be scaled and/or adjusted for specific desirable applications. For example, in some embodiments, a container may have a first diameter when employed with a first type of sample vial, while a container may have a second, larger diameter when employed with a second type of sample vial. In this manner, any suitable dimensions may be employed, as the present disclosure is not so limited.

It should also be noted that while exemplary containers for containing sample vials are discussed herein with reference to some embodiments, alternative objects contained by such containers are contemplated. For example, in some embodiments, containers according to exemplary embodiments herein may be configured to contain sanitary or other hygienic products (e.g., napkins, tampons, pads, soap, etc.). Of course, a container may be configured to contain any suitable objects, as the present disclosure is not so limited. For example, containers may be configured to contain edible items (e.g., candy, snacks), travel accessories (e.g., headsets, eye masks, socks, slippers, toothbrushes, toothpaste), electronics (e.g., flash drives, memory cards, chargers, batteries), eyewear (e.g., glasses, sunglasses), medicines, stationery (e.g., pens, pencils, erasers) or any other suitable object.

In some such embodiments, a container according to exemplary embodiments herein may be configured to be employed in vending machines.

The container may protect the object until used by an end user. In some embodiments, an end user may be able to recycle the container, allowing container to be reused after processing (e.g., cleaning, restocking, etc.).

According to exemplary embodiments described herein, an accessioning system may be configured to accession 8,000 samples contained in exemplary containers described herein in a 24-hour period. In some cases, an accessioning system may be configured to accession one sample every 10 seconds. In some embodiments multiple accessioning systems may be employed to increase the rate of container accession. Additionally, in some embodiments, a lesser or greater rate of containers may be accessioned as desired, as the present disclosure is not so limited.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1A is a side schematic of one embodiment of a container 100 in an empty state. As shown in FIG. 1A, the container includes a cap 102 and a base 120. The cap is configured to be removably coupled to the base to create an internal volume. According to the embodiment of FIG. 1A, the cap 102 includes a cap internal volume 105 accessible via a cap opening 104. Similarly, the base 120 includes a base internal volume 123 accessible via a base opening 122. The cap 102 also includes an external cap key 106, which is configured to engage a decapper to allow the decapper to apply torque to the cap. Similarly, the base 120 includes an external base key 124 configured to engage a conveyor to allow the conveyor to apply torque to the base (or alternatively, resist torque applied to the conveyor by the base). In the embodiment of FIG. 1A, the external cap key and external base key are configured as notches formed the cap and base, respectively. In the embodiment of FIG. 1A, the external cap key and external base key each include a plurality of notches. Additionally, in the embodiment of FIG. 1A, the external cap key and the external base key share the same shape. Of course, in other embodiments, the external cap key and external base cap may have different shapes, as the present disclosure is not so limited.

According to the embodiment of FIG. 1A, the cap 102 of the container 100 is configured to receive the base 120 such that an inner diameter of the cap is greater than an outer diameter of the base. In other embodiments, the base may be configured to receive the cap (e.g., an inner diameter of the base is greater than an outer diameter of the cap), as the present disclosure is not so limited. As shown in FIG. 1A, the base includes a closure 128 and a flange 126. The closure 128 of the depicted embodiment is a protrusion which is configured to engage the cap 102 to removably couple the base 120 to the cap. In particular, the cap 102 may include a receptacle configured to receive the protrusion such that the base is coupled to the cap. To remove the base from the cap, a threshold force may be applied to the cap 102 in a direction away from the base 120. Accordingly, the closure of FIG. 1A may be a longitudinal closure, where force applied along a longitudinal axis of the container may be employed to open or close the container 100. The flange 126 may function as a stop to resist further movement of the base into the cap. In some embodiments, the flange may be employed by an accessioning system for retaining and/or orienting the base (for example, sec FIGS. 15A-15C).

According to the embodiment of FIG. 1A, the cap 102 has a cap longitudinal length L1 and the base 120 has a base longitudinal length L2. As shown in FIG. 1A, the cap longitudinal length is greater than the base longitudinal length. In particular, in the embodiment of FIG. 1A, the cap longitudinal length is greater than twice the base longitudinal length. In the embodiment of FIG. 1A, the cap and the base approximately share a container diameter of D1. Accordingly, the cap internal volume 105 is also greater than the base internal volume 123 in the embodiment of FIG. 1A. As will be discussed further with reference to FIG. 1B, such an arrangement may allow the container 100 to accommodate sample vials having any height greater than the base longitudinal length up to the combination of the base longitudinal length and the cap longitudinal length minus any overlap therebetween when the container is closed. When the cap is removed from the base, such a sample vial will protrude from the base, allowing the sample vial to be reliably extracted by an accessioning system.

In some embodiments as shown in FIG. 1A, the base 120 includes an identification marker 130. The identification marker 130 is configured to convey information to an imaging sensor (e.g., a camera). In some embodiments, the identification marker may convey information including one or more selected from the group of type of sample, age of sample (e.g., manufacturing date, shipping date, etc.), and manufacturing information. In some embodiments, the identification marker is a QR code. In other embodiments, the identification marker is a barcode. In still other embodiments, the identification marker is a symbol detectable by optical character recognition or another imaging processing technique (e.g., machine vision). In some embodiments, the identification marker is disposed on a bottom exterior surface of the base 120. In some embodiments, the identification marker is disposed on a top exterior surface of the cap 102.

Figure 1B:
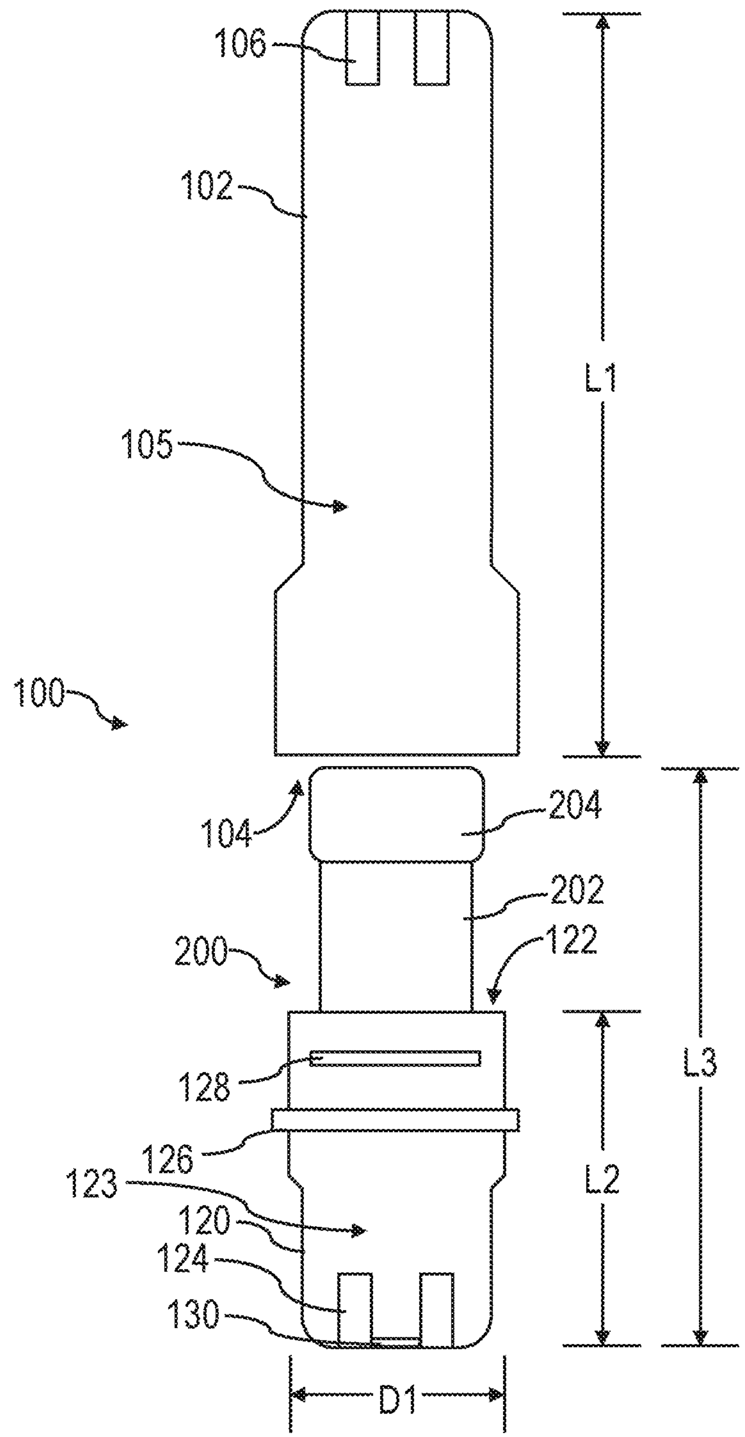
FIG. 1B is a side schematic of the container of FIG. 1A in a full state carrying a sample vial.

FIG. 1B is a side schematic of the container 100 of FIG. 1A in a full state carrying a sample vial 200. As shown in FIG. 1B, the sample vial 200 is supported by the base 120 of the container. In the state shown in FIG. 1B, the sample vial includes a sample vial body 202 and a sample vial cap 204. The sample vial body 202 is disposed in the base internal volume. The sample vial protrudes out of the base opening 122. The sample vial has a sample vial length L3 which is greater than the base longitudinal length L2. The sample vial length L3 is between the base longitudinal length L2 and C1, the overall container length when the container is fully closed (see FIG. 1C). C1 may also be expressed as L1+L2 minus the overlap between L1 and L2 when the container is closed. Sample vials of any length between L2 and C1 may be accommodated by the container of FIG. 1B. In some embodiments, the cap longitudinal length L1 may be between 70 and 100 mm (e.g., 80 mm). In some embodiments, the base longitudinal length L2 may be between 35 and 45 mm (e.g., 42 mm). In some embodiments, the container diameter D1 is between 20 and 25 mm (e.g., 24 mm). In some embodiments, the overall container length C1 is between 100 and 130 mm (e.g., 117 mm). Of course, other measurements of various portions of the container are contemplated, and the present disclosure is not so limited in this regard.

Figure 1C:
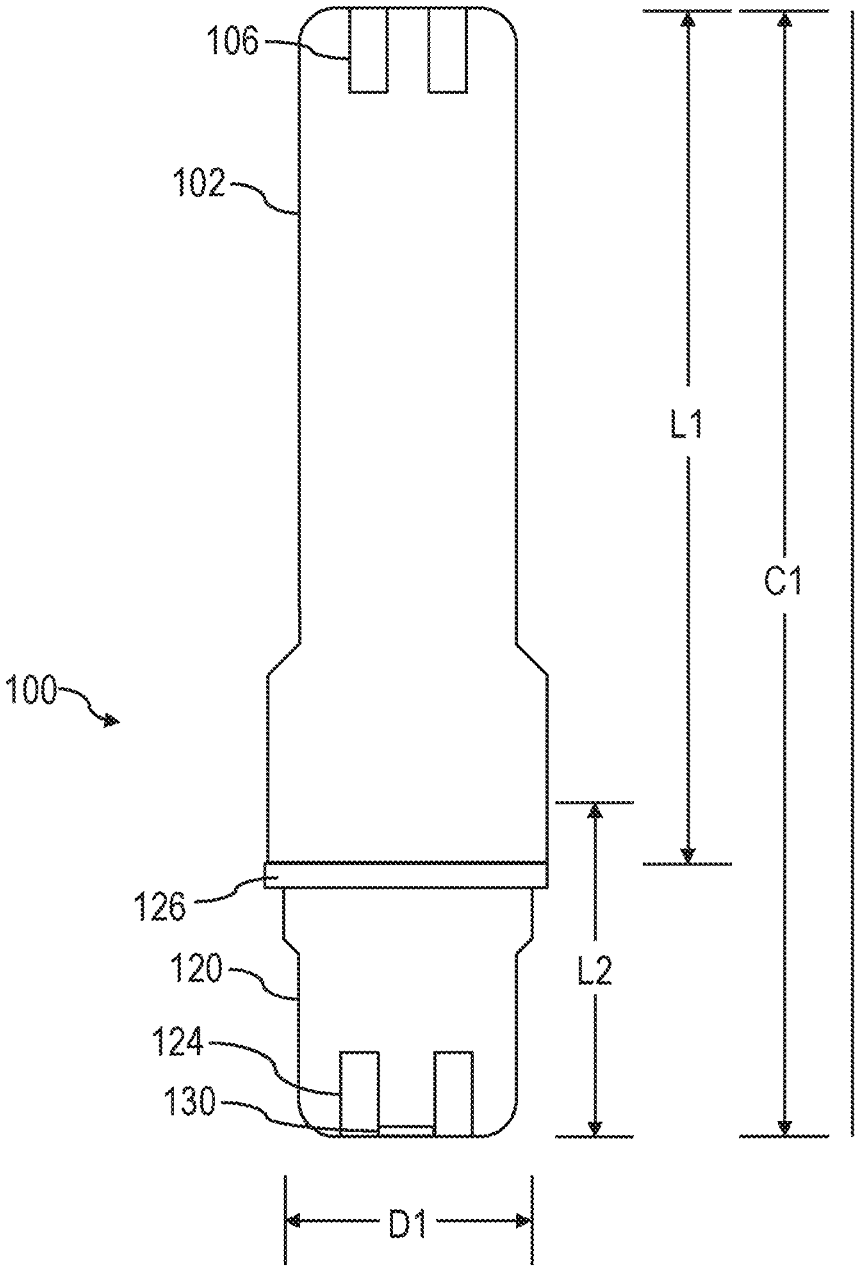
FIG. 1C is a side schematic of the container of FIG. 1A in a closed state.

FIG. 1C is a side schematic of the container 100 of FIG. 1A in a closed state. As shown in FIG. 1B, the container 100 has an overall container length C1 when the container is closed. The overall container length C1 may establish the maximum length of a sample vial accommodated by the container. That is, the sample vial may have a length between the longitudinal base length L2 and the container length C1. The container length C1 may be equal to the combination of the cap longitudinal length L1 and the base longitudinal length L2 minus overlap therebetween when the cap is coupled to the base. According to some embodiments as shown in FIG. 1C, the cap longitudinal length L1 forms a majority (e.g., greater than 50%) of the overall container length C1 when the container is in the closed state. In some embodiments, the cap longitudinal length L1 may form greater than 75% of the overall container length C1 when the container is in the closed state.

Figure 2:
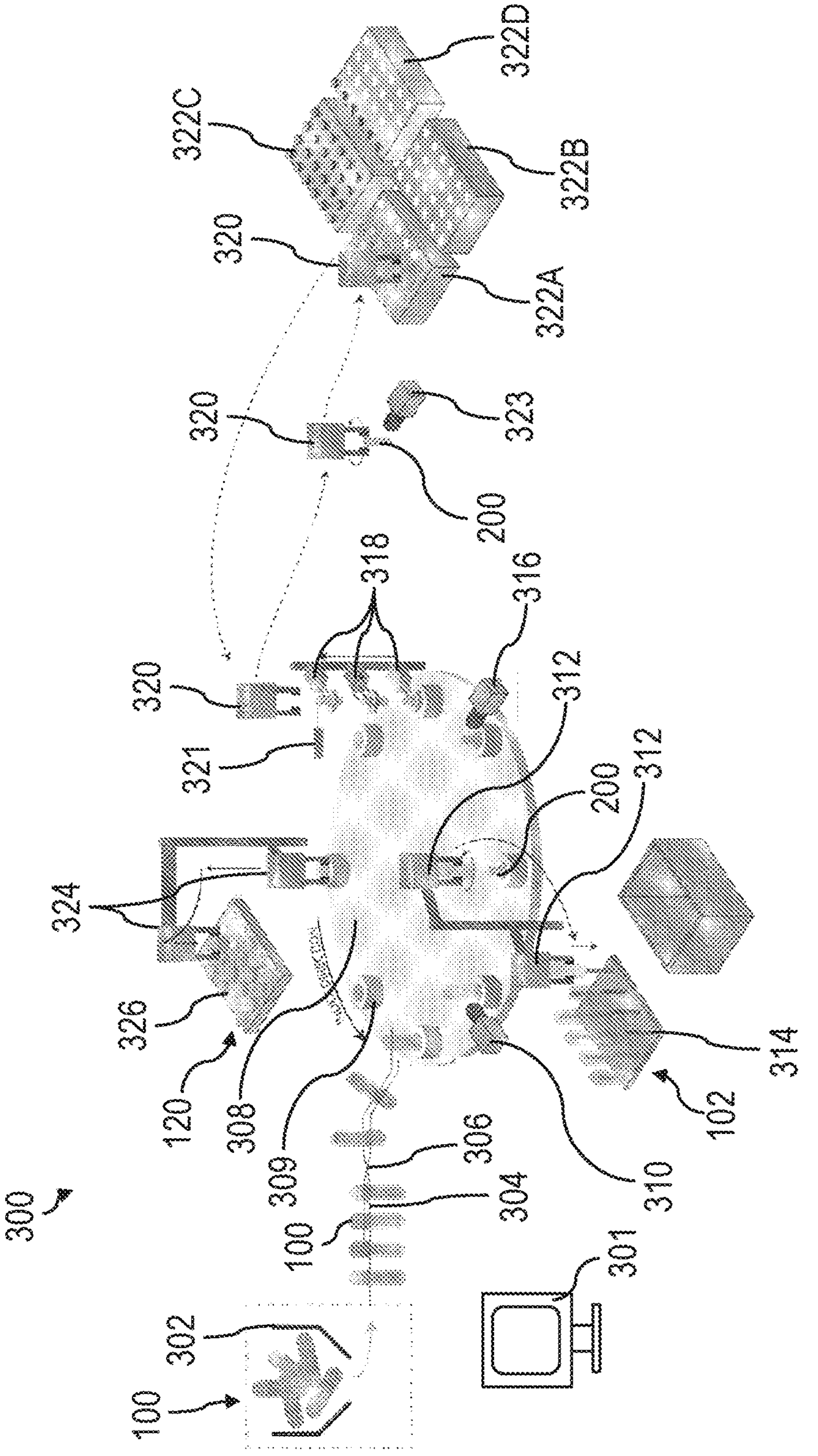
FIG. 2 is a schematic of one embodiment of an automated accessioning system.

FIG. 2 is a schematic of one embodiment of an automated accessioning system 300. As shown in FIG. 2, the system includes a hopper 302. The hopper 302 is configured to receive a plurality of containers 100 according to exemplary embodiments described herein. In some embodiments as shown in FIG. 2, the system also includes a receiver 304. In one embodiment, the receiver is configured to sequentially receive containers from the hopper 302 and move the containers toward a conveyor 308. In the embodiment of FIG. 2 the receiver 304 includes an orienting portion 306 configured to flip the containers to an upright orientation where the base is disposed below the cap. In the embodiment of FIG. 2, the receiver 304 is configured as a transporter track, though other arrangements are contemplated. For example, in some other embodiments, the receiver 304 may include a gripper configured to select a container from the hopper 302 and place the container on the conveyor 308. Such an exemplary arrangement will be discussed further with reference to FIGS. 30A-30B. In some embodiments, the number of containers 100 in hopper 302 are at or below a threshold number, where the threshold number is selected to make it efficient, easier, and/or faster to select a container from the hopper 302. In some embodiments, the hopper 302 is a vibratory canister feeder configured to vibrate to cause the plurality of containers to lay flat and separate from one another to allow the gripper to easily pick the container from the hopper 302. Such an arrangement is also discussed further with reference to exemplary FIGS. 30A-30B. In some such embodiments, the accessioning system may include a sensor configured to determine an orientation of a container dispensed from the hopper, and the gripper may be used to orient the container to a desired orientation (e.g., an upright orientation).

In some such embodiments, the accessioning system 300 may include an imaging sensor (not shown) configured to image one or more of the plurality of containers 100 in the hopper 302. In one such embodiment, the imaging sensor is configured to image an internal volume of the container. In some embodiments, a wall of the container may be translucent such that the internal volume is at least partially visible to the imaging sensor. The imaging sensor may provide information to at least one processor configured to detect a presence of droplets, liquid, a solution or other substance on the wall of the container which may be indicative of a leak in the container. In some embodiments, the processor may also update a status of the container in a database if the container is not properly closed or there is a leak in the container. In one such embodiment, the imaging sensor is configured to image the overall container. The imaging sensor may provide information to a processor configured to determine whether the container is partially open, missing a portion of the container (e.g., the cap of the container), or is otherwise damaged. In some embodiments, the imaging sensor may provide information to the at least one processor that may employ the information to determine if a base 120 and a cap 102 of a container are in alignment (e.g., fully closed). For example, alignment markings on the cap and base (e.g., a stripe, a line, structural feature, etc.) may be imaged by the imaging sensor. If the alignment markings on the cap and base are not aligned, the at least one processor may determine that the container is not closed. In some embodiments, if a processor determines that the base 120 and cap 102 of the container 100 are not closed and/or determines that there is a leak (or otherwise that there is a presence of liquid) in a container, the container in question may be flagged for removal from the hopper 302 and placed in a quarantine location. In some embodiments, if a processor determines that a container is partially open, missing a portion of the container (e.g., the cap of the container), or otherwise damaged, the container may be flagged for removal from the hopper 302 and placed in a quarantine location. In one embodiment, when the hopper 302 is a vibratory canister feeder, the vibration of the hopper 302 is stopped when the container is flagged for removal. Such an arrangement may ensure any liquid is not spread in or by the hopper. If the processor determines that there is no leak in the container, not partially open, not missing a portion of the container, and/or not damaged, the container may be allowed to stay in the hopper 302 until the container is selected by the gripper to continue through an accessioning process.

According to the embodiment of FIG. 2, the conveyor 308 includes a plurality of receptacles 309, each of which is configured to receive a base of a container. In the embodiment of FIG. 2, the conveyor is a rotary conveyor configured to rotate the receptacles 309 in a circle. Other arrangements of the conveyor are also contemplated, including, but not limited to, linear conveyors. According to the embodiment of FIG. 2, the receptacles 309 are configured to hold a container in an upright orientation by the base of the container. In some embodiments, the accessioning system may include an imaging sensor configured to read an identification marker disposed on the base of the container 100. Such an exemplary embodiment will be discussed further with reference to 15A-15C. In some embodiments, an accessioning system may include no intermediate receiver between the hopper 302 and the conveyor 308. In such embodiments, the hopper 302 may dispense a container directly onto the conveyor. In some such embodiments, the hopper 302 may dispense a container directly into one of the plurality of receptacles 309.

As shown in FIG. 2, once a container 100 is received in a receptacle 309 of the conveyor 308, the conveyor may move the container in a counter-clockwise direction. The accessioning system 300 includes a first imaging sensor 310 configured to image a cap of the container. In particular, the first imaging sensor 310 is configured to image an internal volume of the container. In some embodiments, a wall of the container may be translucent such that the internal volume is at least partially visible to the first imaging sensor. The containers may include a hydrochromic indicator disposed in the internal volume that is configured to change colors when exposed to liquid, a solution, or other substance in the internal volume. In some embodiments, the hydrochromic indicator includes a desiccant to absorb the liquid, solution, or other substance in the internal volume. In some embodiments, the desiccant and the hydrochromic indicator are combined to create an absorbent device capable of absorbing liquid and changing color when coming into contact with a liquid, solution, or other substance in the internal volume. The first imaging sensor may provide information to a processor configured to determine a state of the hydrochromic indicator. If the processor determines that the hydrochromic indicator has been or is currently exposed to liquid, a solution, or other substance, the container may be flagged for removal from the conveyor 308 and placed in a quarantine location. In some embodiments, the processor may also update a status of the container in a database if the hydrochromic indicator has been exposed to liquid. If the processor determines that the hydrochromic indicator has not been exposed to liquid, a solution, or other substance, the container may be allowed to continue on the conveyor 308 through an accessioning process.

According to the embodiment of FIG. 2, the accessioning system 300 includes a decapper configured as a first gripper 312. The first gripper 312 is configured to engage a cap 102 of the container 100 and remove the cap from the base 120 of the container. In the specific embodiment of FIG. 2, the first gripper 312 is configured to rotate the cap relative to the base. The receptacle 309 is configured to resist rotation of the base such that torque applied to the cap by the first gripper rotates the cap relative to the base. Once the cap is decoupled from the base, the first gripper moves the cap 102 to an optional cap rack 314, which may be used to store and/or clean (e.g., clean, sanitize, disinfect, and/or sterilize) a plurality of caps. In other embodiments, the cap 102 may be stored in a cap container, general storage container (e.g., that is shared between caps and bases) or another suitable location. In some embodiments, an automated cap processing system may convey the caps to a separate location or container. In other embodiments, the first gripper 312 or another gripper may place the caps in a container or another suitable location. Once the cap is removed from the container, a sample vial 200 stored in the container is revealed and protrudes out of the base 120 and receptacle 309. While in the embodiment of FIG. 2 the accessioning system is configured to de-cap a single container at a time with the first gripper 312, in other embodiment a decapper may include a plurality of grippers configured to simultaneously de-cap multiple containers. In some such embodiments, the conveyor 308 may include a plurality of receptacles arranged in grouped arrays, where each array is configured to hold multiple containers at the same time. The decapper may include a plurality of grippers configured to engage each of the containers in the array simultaneously. Accordingly, the grippers may also be arranged in an array matching that of the receptacles.

In some embodiments, the cap 102 of each container in the cap rack 314 may be reused. That is, each cap may be cleaned before being provided to additional users for shipping an additional sample vial. In some embodiments, each cap of a container may include a manufacture identifier that allows the automated accessioning system to track a unique cap. In some embodiments, when the cap is moved to the cap rack 314, a marking may be etched or laser engraved into a portion of the cap, such that the cap manufacture identifier is updated each time a cap passes through the automated accessioning system. In this manner, a particular cap of a container may be tracked throughout its lifecycle. It should also be noted that once the caps 102 are separated from the bases 120, a unique cap is able to be reused with any base, whether that be the base the cap originally arrived with in the accessioning platform with or a different base, as the present disclosure is not so limited.

As shown in FIG. 2, the accessioning system includes a second imaging sensor 316. The second imaging sensor is configured to observe the sample vial 200 after the sample vial has been exposed by removal of the cap 102. The second imaging sensor is configured to provide information to a processor that is configured to detect an orientation of the sample vial 200. In particular, the information from the second imaging sensor is employed to determine whether the sample vial is in an upright orientation where a sample vial cap is above a bottom portion of the sample vial, or an inverted orientation where the sample vial cap is below the bottom portion of the sample vial. The accessioning system also includes a second gripper 318 which is configured to grasp and lift the sample vial from the base 120 of the container 100. Depending on the determined orientation of the sample vial, the second gripper is configured to orient the sample vial to the upright orientation. That is, upon detecting the sample vial is in the inverted orientation, the second gripper 318 is configured to flip or rotate the sample vial to the upright orientation. Upon detecting the sample vial is in the upright orientation, the second gripper may simply lift the sample vial from the base of the container without rotating the sample vial.

According to the embodiment of FIG. 2, once the sample vial 200 has been removed from the container by the second gripper 318 and oriented in the upright orientation, the height of the sample vial is measured with a height sensor 321. In some embodiments, the height sensor may be a break-beam sensor configured to detect when the sample vial 200 is positioned at the level of the height sensor. In such an embodiment, the second gripper 318 may lift the sample vial until the beam of the height sensor 321 is broken. In other embodiments, the height sensor may detect a position of the sample vial in two dimensional or three-dimensional space. For example, in some embodiments the height sensor be a 3D or stereoscopic camera or may otherwise employ image processing to determine the position of the sample vial based on the position of the sample vial in the frame of the height sensor. As shown in FIG. 2, the accessioning system includes a third gripper 320 configured to grasp the sample vial and remove the sample vial from the second gripper 318. In embodiments where the sample vial is positioned at a predetermined height by the second gripper, the third gripper may simply grasp the sample vial at the same position for each sample vial. In embodiments where the height sensor detects a position the sample vial in space, the third gripper may be controlled to grasp the sample vial at an appropriate location. The third gripper is configured to move the sample vial to one of a plurality of sample racks 322A, 322B. 322C, 322D. In the depicted embodiment, the sample racks may each be associated with a different type of sample. In some embodiments as shown in FIG. 2, a third imaging sensor 323 may be employed to read a label disposed on the sample vial. In some embodiments as shown in FIG. 2, the third gripper 320 may rotate the sample vial 200 so that any label of the sample vial may be read by the third imaging sensor. A processor may employ information obtained by the third imaging sensor to command the third gripper 320 to place the sample in an assigned sample rack. For example, the label (e.g., a barcode) may include information such as sample type (e.g., blood, stool, saliva, etc.) and/or assay type (e.g., cholesterol, complete blood count, genomic sequencing, etc.) which may be used to sort the sample vials. In other embodiments, there may be no third imaging sensor, and the sample vial may be placed in an assigned sample rack based on information from an identification marker disposed on the container. The identification marker may be indicative of a sender, which may be associated with information regarding the sample (e.g., sample type, assay type, etc.). In some embodiments, a color of a container or sample vial may be employed to assist with sorting, where the color of the container may be associated with information regarding the sample (e.g., sample type, assay type, etc.). Each sample rack may be replaced once filled with sample vials.

As shown in FIG. 2, in some embodiments, the accessioning system may include a fourth gripper 324 configured to remove a base of a container from the conveyor 308. In particular, the fourth gripper is configured to grasp the base and lift the base from the receptacle. The fourth gripper is configured to place the base of each container in an optional base rack 326. The base rack 326 may be configured to temporarily store bases and may also be employed to clean, sanitize, disinfect and/or sterilize the bases for future use. In other embodiments, the base may be stored in a base container, general storage container (e.g., that is shared between bases and caps) or another suitable location. In some embodiments, an automated base processing system may convey the bases to a separate location. In other embodiments, the fourth gripper 324 or another gripper may place the bases in a container or another suitable location. Once the base is removed from the conveyor, the associated receptacle 309 is ready to receive another container form the receiver 304. In this manner, the accessioning system may be configured to reliably extract sample vials from containers according to exemplary embodiments described herein.

In some embodiments, the base 120 of each container 100 in the base rack 326 may be reused. That is, each base may be cleaned (e.g., cleaned, sanitized, disinfected and/or sterilized) before being provided to additional users for shipping a sample vial. In some embodiments, each base of a container may include a manufacture identifier that allows the automated accessioning system to track a unique base. In some embodiments, when the base is moved to the base rack 326, a marking may be etched or laser engraved into a portion of the base, such that the base manufacture identifier is updated each time a base passes through the automated accessioning system. In this manner, a particular base of a container may be tracked throughout its lifecycle. It should also be noted that once the bases 120 are separated from the caps 102, a unique base is able to be reused with any cap, whether that be the cap the base originally arrived with in the accessioning platform with or a different cap, as the present disclosure is not so limited.

In some embodiments as shown in FIG. 2, the accessioning system includes a at least one computing device 301. The at least one computing device 301 contains at least one processor configured to execute software (for example, see FIG. 25). The software may include processor-executable instructions stored on non-volatile memory. In some embodiments, the software includes instructions to process imagery or information obtained by one or more of the imaging sensors 310, 316, 323 to make the determinations described above. For example, the at least one computing device may be configured to determine the state of a hydrochromic indicator and/or an orientation of a sample vial. The at least one computing device may generate and/or provide one or more commands to perform actions in the accessioning system. For example, the at least one computing device may be in electrical communication with the hopper 302, receiver 304, and grippers 312, 318, 320, 324. In some embodiments, the at least one computing device may cause (e.g., instruct or command) the hopper to dispense a container, cause (e.g., instruct or command) a gripper to flip a vial, cause (e.g., instruct or command) a gripper to place the vial into an assigned sample rack, cause (e.g., instruct or command) a gripper to place a cap in a cap rack, cause (e.g., instruct or command) a gripper to place a base in a base rack, discard a sample vial, generate an alert, or perform any other actions of the accessioning system. In some embodiments, the at least one computing device 301 may be in the same room and may be physically integrated with the accessioning system 300. Alternatively, in other embodiments, the at least one computing device 301 may be communicatively coupled to the accessioning system (e.g., using a wired or wireless communication protocol). In some such embodiments, the at least one computing device 301 may not be disposed in the same room as the accessioning system 300 and may be remote.

It should be noted that while an accessioning system including multiple grippers and sub-processes are shown and described with reference to FIG. 2, it should be noted that the sub-processes may be employed alone or in combination. That is, in some embodiments, the various steps including transfer of the containers from hopper to the conveyor, detection of the state of a hydrochromic indicator, de-capping of a container, lifting of a sample vial from a base, re-orienting the sample vial, transferring the sample vial to a sample rack, and removing the base from the receptacle may be employed alone or in any combination. Some embodiments and alternatives of such sub-processes are described further below.

It should also be noted that while in the embodiment of FIG. 2 the accessioning system manipulates a single container during each sub-process, in other embodiments an accessioning system may be configured to manipulate groups of containers simultaneously during a sub-process. For example, in some embodiments a decapper may be configured to de-cap multiple containers simultaneously. As another example, multiple sample vials may be lifted from their respective bases simultaneously. In some embodiments, groups of containers may be arranged in arrays of receptacles on a conveyor. Thus, an accessioning system may manipulate single containers or groups of containers during the various sub-processes described with reference to FIG. 2, as the present disclosure is not so limited. In some embodiments, the accessioning system may be configured to detect a color of a container or a portion of a container (e.g., a container cap). In some such embodiments, the accessioning system may be configured to manipulate groups of containers based on the color of the containers. For example, a first group of containers having the same color may be manipulated simultaneously or in series, before a second group of containers is manipulated simultaneously or in series.

It should also be noted that while in the embodiment of FIG. 2 the accessioning system 300 includes three imaging sensors 310, 316, 323, in other embodiments any number of imaging sensors or other sensors may be employed for use in any sub-process of the accessioning system. For example, in some embodiments a single imaging sensor may be employed that images a container or portions thereof for the various sub-processes described with reference to FIG. 2. In some such embodiments, information from the single imaging sensor may be processed by at least one processor of the accessioning system using techniques such as machine vision, machine learning (e.g., using a trained model), image processing, or other suitable techniques which may allow the at least one processor to identify characteristics relevant to a particular sub-process. In other embodiments, a plurality (e.g., two or more) image sensors may be employed. The image sensors may provide information to at least one processor the accessioning system, which may use techniques such as machine vision, machine learning, image processing, or other suitable techniques which may allow the at least one processor to identify characteristics relevant to a particular sub-process. In some embodiments, multiple threads or multiple processors may be configured to perform separate processes on a single image in parallel.

In some embodiments, an accessioning system like the accessioning system of FIG. 2 may include an automated container assembly system. The automated container assembly system may be configured to prepare a container and related object for shipping or delivery to a user prior to use of the object by the user. An exemplary automated container assembly system is discussed further herein with reference to FIGS. 27A-27D. In some embodiments, an accessioning system like that of FIG. 2 may be employed as a container assembly system. For example, the various sub-processes shown in FIG. 2 may be at least partially performed in reverse such that the system of FIG. 2 may assemble a container according to exemplary embodiments described herein. According to some such embodiments, some sub-processes may not be performed during a container assembly process to simplify the container assembly process. For example, in some embodiments a container assembly system may not include one or more imaging sensors configured to provide information regarding a state of a hydrochromic indicator to a computing device, as no liquid will be present in an unused sample vial. Of course, any sub-processes shown in FIG. 2 may be performed or not performed by a container assembly system in reverse, as the present disclosure is not so limited. In some embodiments, an accessioning system and a container assembly system may be separate and distinct from one another, as the present disclosure is not so limited. For example, in some embodiments, a container assembly may be assembled in a container assembly system and later processed by an accessioning system that is separate and distinct from the container assembly system. The container assembly system and the accessioning system may be in different facilities (e.g., in some embodiments, different towns/states/geographical locations).

Figure 3:
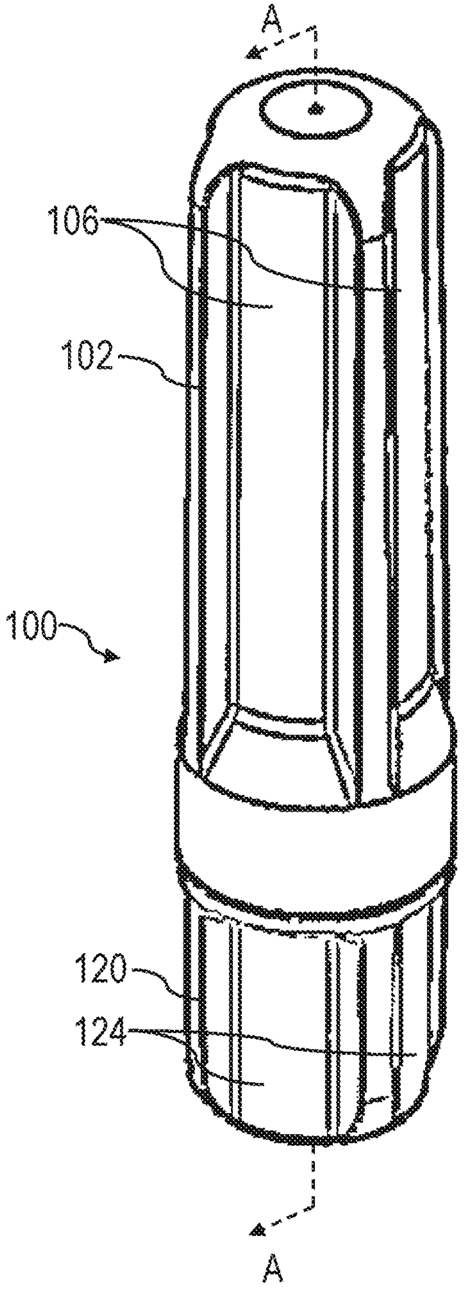
FIG. 3 is a perspective view of another embodiment of a container.

FIG. 3 is a perspective view of another embodiment of a container 100. Similarly to the embodiment of FIGS. 1A-1B, the container of FIG. 3 includes a cap 102 and a base 120. The cap 102 of FIG. 3 includes a plurality of external cap keys 106 which are formed as recesses. Likewise, the base 120 includes a plurality of external base keys 124. Like the embodiment of FIGS. 1A-1B, the cap 102 is configured to receive the base 120.

Figure 4:
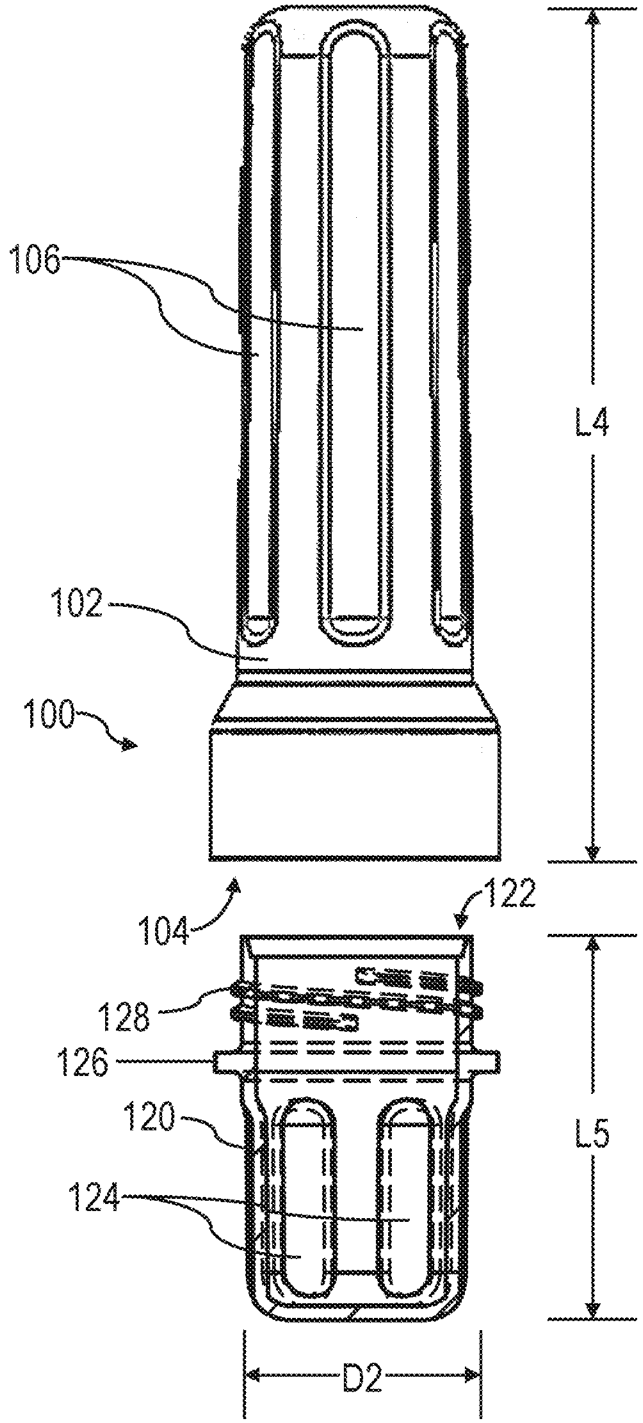
FIG. 4 is an exploded view of the container of FIG. 3.

FIG. 4 is an exploded view of the container 100 of FIG. 3. As discussed previously, the container includes a cap 102 and a base 120 including external cap keys 106 and external base keys 124, respectively. The cap 102 includes a cap internal volume accessible via a cap opening 104, and the base 120 includes a base internal volume accessible via a base opening 122. According to the embodiment of FIG. 4, the cap includes a cap longitudinal length L4 and the base includes a base longitudinal length L5. The cap longitudinal length L4 is greater than the base longitudinal length L5. The cap and the base approximately share a container diameter D2, such that the cap internal volume is greater than the base internal volume.

According to the embodiment of FIG. 4, the base includes a flange 126 and a closure 128 configured to removably couple the base 120 to the cap 102. In the embodiment of FIG. 4, the closure 128 is configured as threads. The cap 102 includes internal threads corresponding to the external threads disposed on the base 120. Accordingly, relative rotation of the base and the cap may selectively open or close the container 100. The internal threads and internal threads are designed such that the container 100 is easy to open and close. In some embodiments, an application torque to close a container may be between 6 and 10 lbs/in. In some embodiments, a removal torque to open a container may be between 3 and 8 lbs/in. In some embodiments, application and/or removal torques outside of these ranges may be employed, as the present disclosure is not so limited. In some embodiments, the application torque and removal torque are selected such that a person can open and close the container with minimal effort, while ensuring that the container is completely sealed when closed and easy for anyone, including those with arthritis, weak hands, etc. As will be discussed further with reference to FIG. 8, the container 100 may include a watertight seal configured to seal the container when the cap and base mate together. The flange 126 functions as a stop to inhibit further insertion of the base into the cap.

Figure 5:
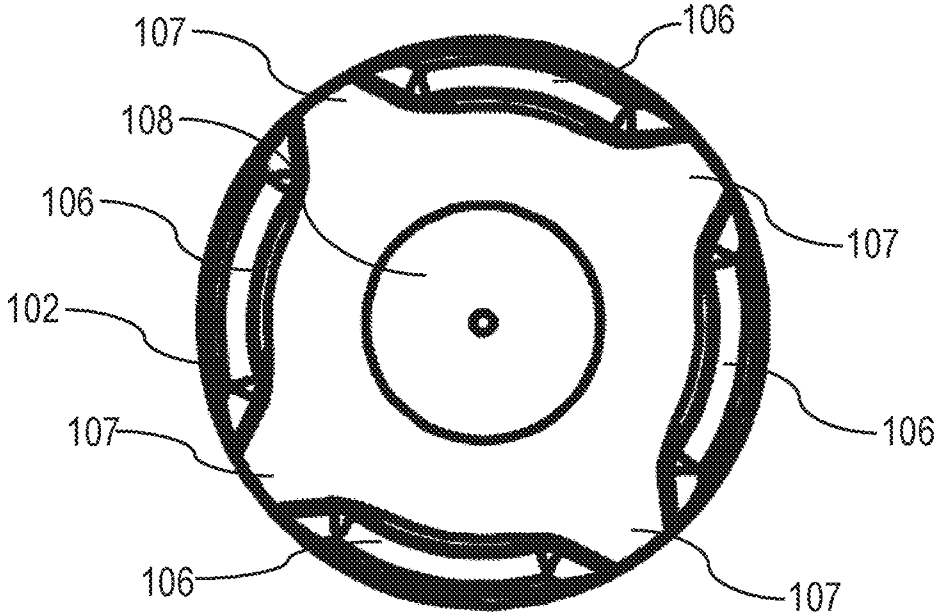
FIG. 5 is a top plan view of the container of FIG. 3.

FIG. 5 is a top plan view of the container of FIG. 3 showing the cap 102. As shown in FIG. 5, the cap includes a plurality of external cap keys 106 formed as recesses. Correspondingly, the cap includes a plurality of ridges 107 extending between the recesses. In the specific embodiment of FIG. 5, the cap includes four external cap keys 106 and four ridges 107. Of course, any suitable number of cap keys may be employed, including a single external cap key, as the present disclosure is not so limited. As shown in FIG. 5, the cap includes a flat top 108. Of course, in other embodiments, a top of the cap may have any suitable shape, as the present disclosure is not so limited.

Figure 6:
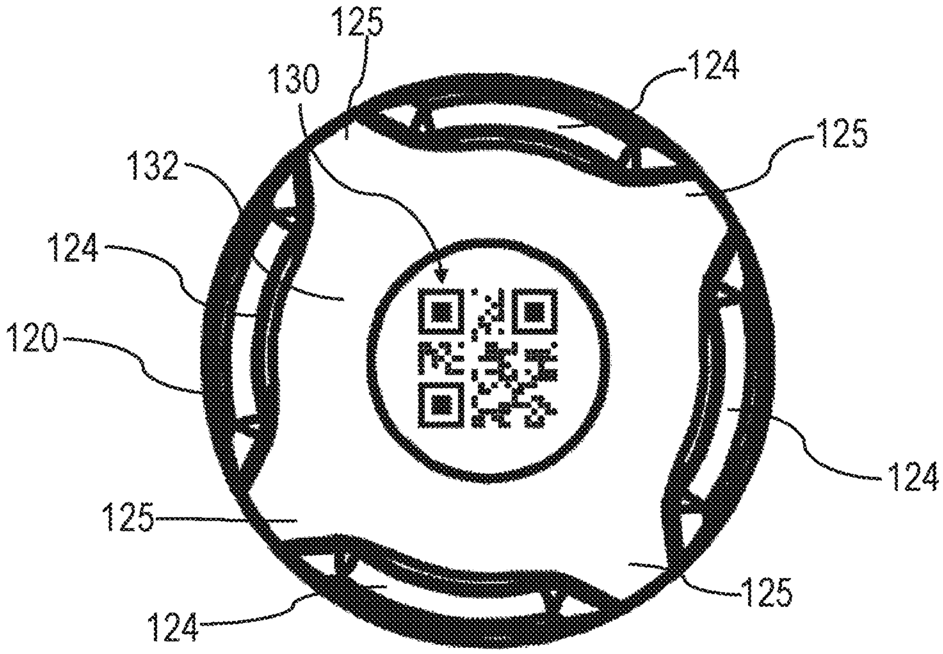
FIG. 6 is a bottom plan view of the container of FIG. 3.

FIG. 6 is a bottom plan view of the container of FIG. 3 showing the base 120. As shown in FIG. 6, the base includes a plurality of external base keys 124 formed as recesses. Correspondingly, the base includes a plurality of ridges 125 extending between the recesses. In the specific embodiment of FIG. 6, the base includes four external base keys 124 and four ridges 125. Of course, any suitable number of base keys may be employed, including a single external base key, as the present disclosure is not so limited. As shown in FIG. 6, the cap includes a flat bottom 132. Of course, in other embodiments, a bottom of the base may have any suitable shape, as the present disclosure is not so limited.

As shown in FIG. 6, the bottom 132 of the base 120 includes an identification marker 130 configured as a QR code. In some embodiments, the identification marker 130 may convey information including one or more selected from the group of type of sample, age of sample (e.g., collection date, shipping date, etc.), and manufacturing information. Of course, any suitable identification marker may be employed, including a bar code or other identification mechanism, as the present disclosure is not so limited.

Figure 7:
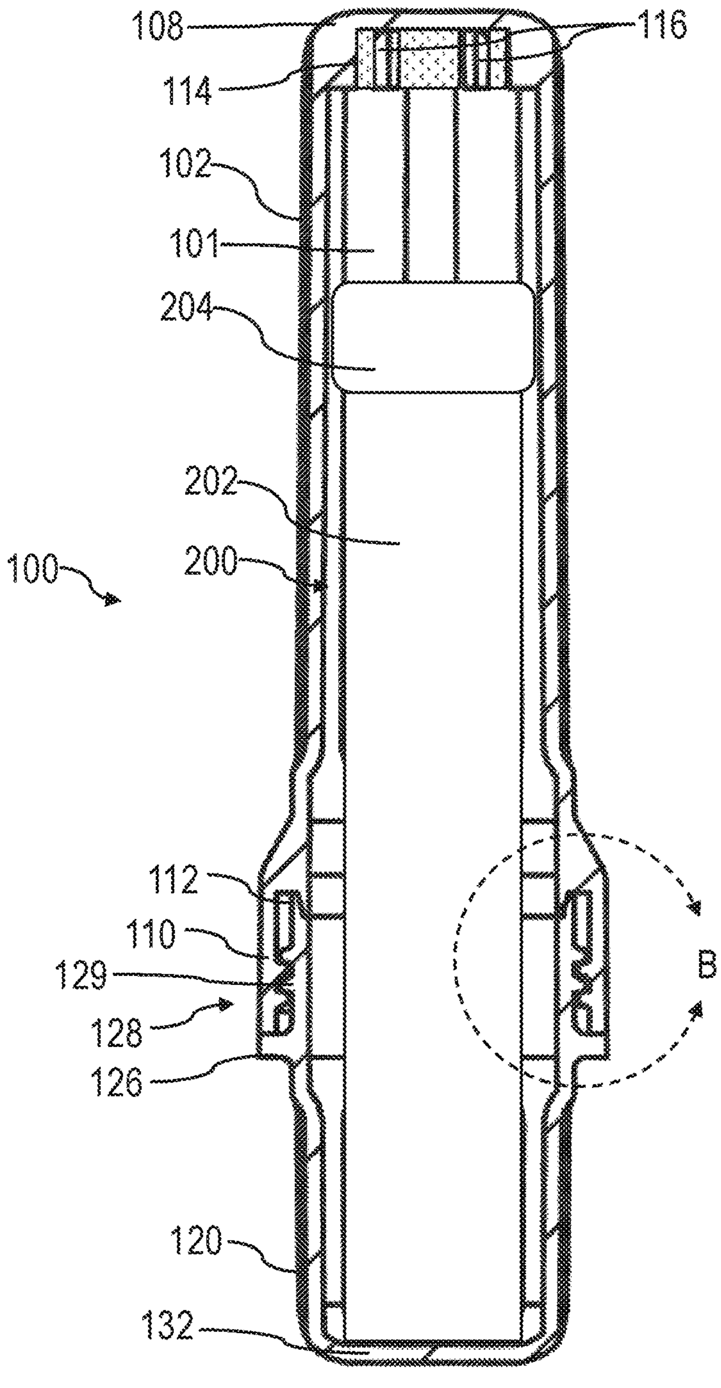
FIG. 7 is a cross-sectional view of the container of FIG. 3 taken along line A-A.

FIG. 7 is a cross-sectional view of the container 100 of FIG. 3 taken along line A-A. As shown in FIG. 7, when the container 100 is closed, the cap 102 and the base 120 form a combined internal volume 101. Inside the internal volume is a sample vial 200 including a sample vial body 202 and a sample vial cap 204. The sample vial 200 is supported by the base 120. As shown in FIG. 7, the container includes a closure 128 configured as external threads 129 on the base and internal threads 110 on the cap configured to threadedly engage the external threads of the base. Accordingly, relative rotation of the base and the cap may close or open the container 100. In the embodiment of FIG. 7, the container includes a watertight seal 112. In some embodiments, the watertight seal may be a gasket. When the base is coupled to the cap via the threads, the watertight seal 112 seals the internal volume. Accordingly, if liquid, a solution, or other substance were to escape the sample vial 200, the liquid would be retained inside of the container.

According to the embodiment of FIG. 7, the container includes a desiccant 114 configured to absorb liquid, a solution, or other substance disposed inside of the internal volume 101. In some embodiments, the desiccant 114 may include a hydrochromic indicator that changes color when exposed to liquid, a solution, or other substance disposed inside of the internal volume 101. The desiccant is retained inside of the internal volume by tabs 116. In the embodiment of FIG. 7, the desiccant is retained in the cap 102 of the container 100. Other arrangements are also contemplated, and the desiccant may be retained in any portion of the internal volume, including in the base 120, as the present disclosure is not so limited.

Figure 8:
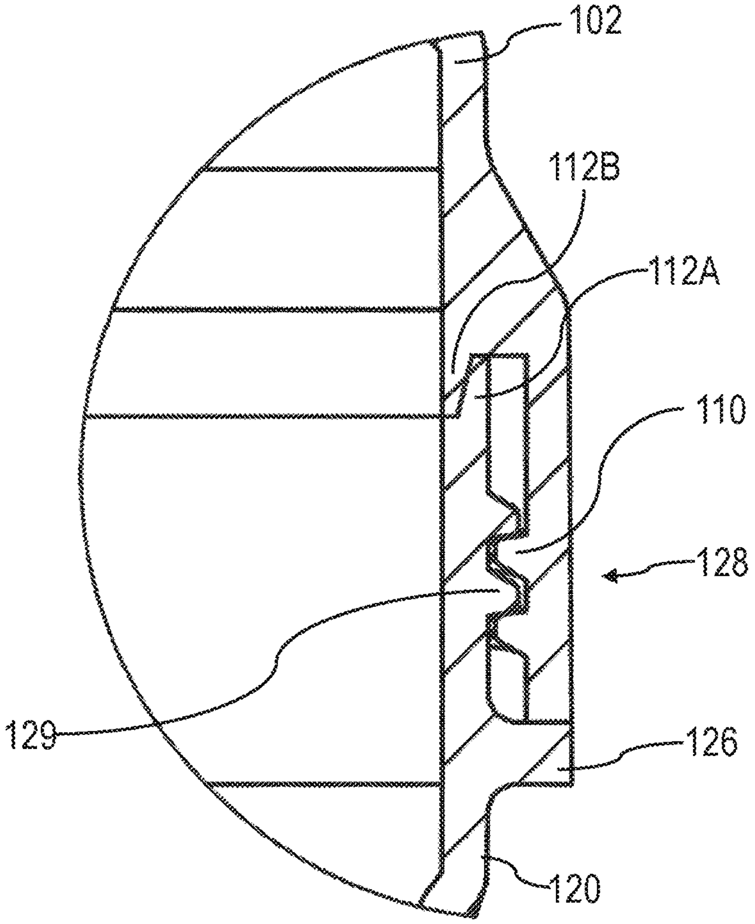
FIG. 8 is an enlarged view of section B-B of the container of FIG. 7.

FIG. 8 is an enlarged view of section B-B of the container of FIG. 7, showing the arrangement of the closure 128 and the watertight seal 112. As shown in FIG. 8, the base 120 includes external threads 129. The cap 102 includes internal threads 110 which are configured to engage the external threads 129. Accordingly, the threaded engagement between the external and internal threads allows relative rotation of the base and the cap to open or close the container. In particular, rotating the cap relative to the base in a first direction moves the base further into the cap 102 until the flange 126 abuts the cap 102. Correspondingly, rotating the cap relative to the base in a second opposite direction moves the base away from and out of the cap 102 until the threads disengage and the base is fully removed from the cap. In other embodiments, the base may receive the cap in a similar manner (e.g., the cap may include external threads, and the base may include internal threads), and the present disclosure is not so limited in this regard. As shown in FIG. 8, the watertight seal has a cap portion 112B and a base portion 112A, which mesh when the base and cap are coupled together. The threaded engagement of the closure 128 may apply force between the cap portion 112B and base portion 112A of the watertight seal to maintain the seal when the container is closed. In some embodiments, the cap portion 112B and the base portion 112A may be formed of a compliant material. Of course, any suitable arrangement for a watertight seal may be employed, as the present disclosure is not so limited.

Figure 9:
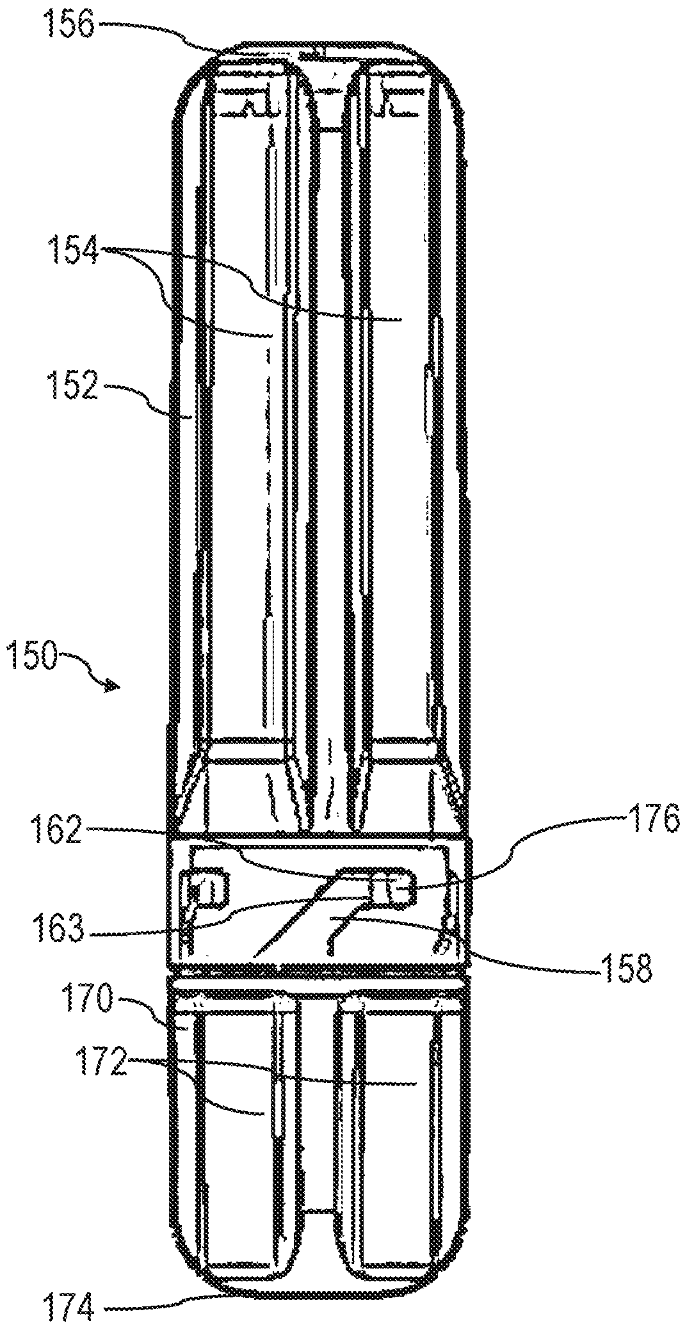
FIG. 9 is a side elevation view of yet another embodiment of a container.

FIG. 9 is a side elevation view of yet another embodiment of a container 150. As shown in FIG. 9, the container includes a cap 152 and a base 170. The cap 152 includes a plurality of external cap keys 154 and a flat top 156. The base 170 includes a plurality of external base keys 172 and a flat bottom 174. In contrast to previously discussed embodiments, the container includes a closure includes a radial projection 176 on the base, and a channel 158, a recess 162, and a protrusion 163 on the cap. The protrusion 163 is configured to produce a click when the projection 176 moves over the protrusion toward the recess 162. The specific arrangement of the channel 158 is shown in FIG. 10B. The specific functionality of the closure will be discussed further with reference to FIGS. 11A-11C.

Figure 10A:
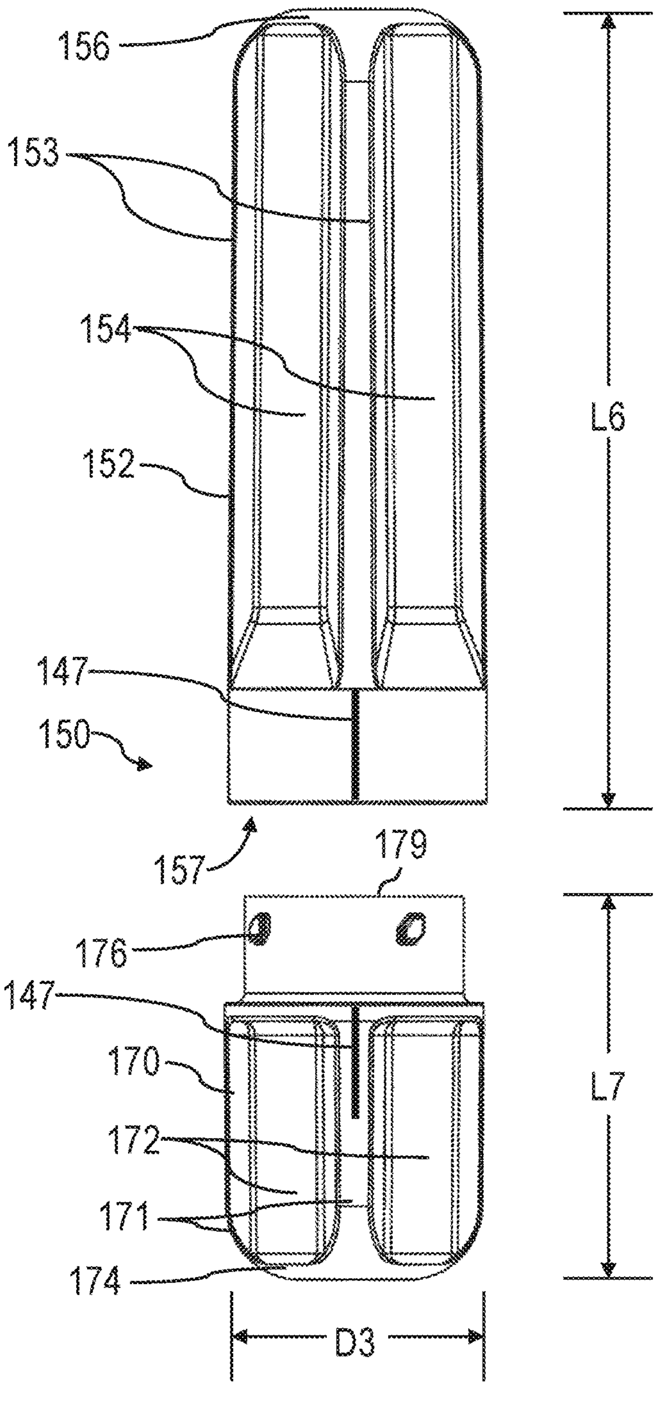
FIG. 10A is an exploded side view of the container of FIG. 9.
Figure 10B:
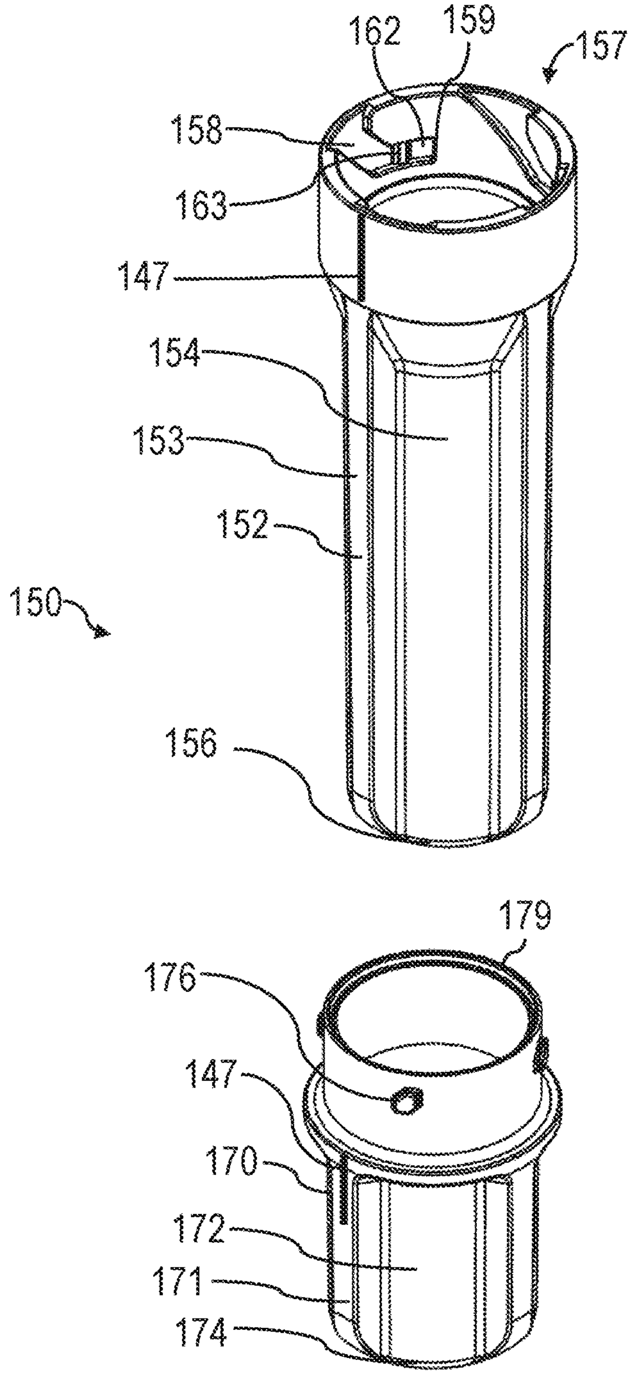
FIG. 10B is an explode perspective view of the container of FIG. 9.

FIG. 10A is an exploded side view of the container 150 of FIG. 9 showing the relative dimensions of the cap 152 and the base 170. As shown in FIG. 10A, the cap includes a cap longitudinal length L6, and the base includes a base longitudinal length L7. The cap longitudinal length is greater than the base longitudinal length. Similar to previously discussed embodiments, the base and cap approximately share a container diameter D3, though in other embodiments the cap and the base may have different diameters.

As shown in FIG. 10A, the cap 152 is configured to receive the base 170 through a cap opening 157. The base includes the radial projection 176, and in the specific embodiment includes four radial projections arranged circumferentially around the base 170. The cap 152 includes the channel, and in the specific embodiment includes four channels each configured to receive one of the projections 176. In other embodiments, any suitable number of channels and projections may be employed, including a single projection and a single channel, as the present disclosure is not so limited. In some embodiments, the container 150 may include a watertight seal which is made when the base 170 is removably coupled to the cap 152. The functionality of coupling the base to the cap via the projections and channels is discussed further below with reference to the exemplary embodiment of FIGS. 11A-11C.

In some embodiments as shown in FIG. 10A, the container 150 may also include lines 147 that function as alignment markings. The lines 147 are configured to visually indicate when the container is closed. That is, when the cap 152 is fully secured to the base 170, the lines 147 are aligned and form a stripe. When the cap is not fully secured to the base 170, or is improperly secured to the base (e.g., misaligned, cross-threaded in containers having threads, etc.), the lines 147 may not be aligned or otherwise spaced from one another. The alignment of the lines as a stripe may function as a visual marker that is detectable by one or more imaging sensors. For example, an imaging sensor may image the container 150 and provide information to at least one processor, which may determine whether the container is closed based on the image of the lines 147. While lines are shown in FIG. 10A, any suitable marking may be employed on a cap and base in any orientation (e.g., diagonal, nonlinear, curved, patterns, etc.), as the present disclosure is not so limited. In some embodiments, physical features of the container itself may be employed to visually indicate closure. For example, in some embodiments, alignment of the ribs 153 of the cap 152 with the ribs 171 of the base 170 may indicate closure of the container in addition to or instead of the lines 147. Any marking and/or physical feature may be employed to visually indicate closure of a container according to exemplary embodiments described herein, as the present disclosure is not so limited. Additionally, alignment markings and/or physical features may be employed on any type of closure, including rotating closures (e.g., threads, projections and receptacles) and linear closures (e.g., protrusions), as the present disclosure is not so limited.

FIG. 10B depicts an exploded perspective view of the container 150 of FIG. 9 with the cap 152 inverted to show the channel 158, which is accessible through the cap opening 157. As shown in FIG. 10B, the channel 158 terminates in a closed end 159. The channel also includes a recess 162 and a protrusion 163 disposed in the channel. According to the embodiment of FIG. 10B, the protrusion 163 and the closed end 159 define the recess 162. The protrusion is configured to generate an audible and/or tactile click when the projection 176 of the base 170 slides over the protrusion. Such a click may provide feedback to a user that the container is closed. The recess 162 is configured to releasably retain the projection 176 such that the base may be removably coupled to the cap. The specific motion of the projection 176 within the channel 158 is discussed further with reference to FIGS. 11A-11C.

Figure 11A:
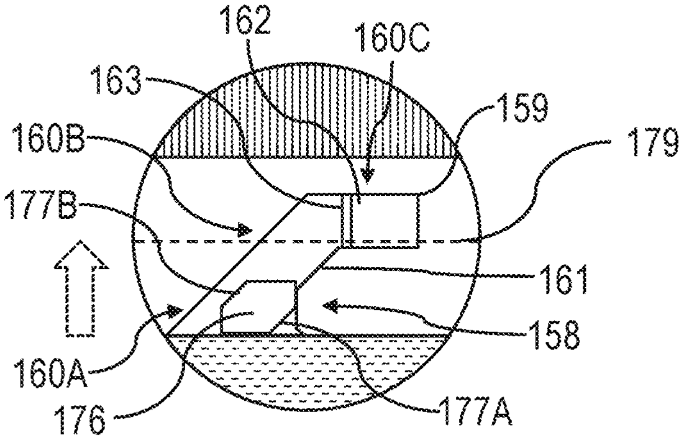
FIG. 11A depicts a schematic of one embodiment of closure in a first state.

FIG. 11A depicts a schematic of one embodiment of a closure in a first state. The schematic of FIG. 11A is equivalent to the closure shown in FIGS. 9-10B and is shown in a simplified schematic for clarity. As shown in FIG. 11A, the closure includes a channel 158 and a projection 176. In the schematic shown in FIGS. 11A-11C, the projection 176 may be disposed on a cap or a base of a container, with the channel 158 disposed on the opposite portion of the container as the projection. For example, the projection 176 may be disposed on the base, and the channel 158 may be disposed on the cap. As another example, the projection may be disposed on the cap, and the channel may be disposed on the base. Accordingly, the present disclosure is not so limited in this regard. In the schematic of FIG. 11A, an upper portion 179 of the base is shown in dashed to represent the relative longitudinal movement of the cap and the base.

As shown in FIG. 11A, the channel 158 includes a protrusion 163 and terminates in a closed end 159 and a recess 162. The protrusion 163 is configured to contact the projection 176 as the projection moves toward the closed end 159 of the channel. As the protrusion moves past the protrusion, the protrusion and projection may produce a click, which may provide auditory and/or tactile feedback for a user to relay that the projection 176 is past the protrusion 163. The recess 162 is configured to releasably retain the projection 176 at the closed end 159 of the channel. When the projection drops into the recess 162, the projection and channel may also produce a click, which may provide auditory and/or tactile feedback for a user to relay that the container is closed. In some embodiments, the click produced by the protrusion 163 and the recess 162 may occur nearly simultaneously, such that the user perceives a single click. In some such embodiments, the protrusion 163 and the closed end 159 may define the recess 162 configured to retain the projection 176 in the channel 158. In other embodiments, the clicks produced by the protrusion and the recess may occur in sequence, such that a user perceives two distinct clicks. In such an embodiment, the protrusion 163 may be spaced from the recess 162. In some embodiments, the channel 158 may include either the protrusion 163 or the recess 162. That is, the protrusion 163 and recess 162 may be employed in a closure independently or may be employed in combination, as the present disclosure is not so limited.

As shown in FIG. 11A, the channel also includes a first portion 160A, a second portion 160B, and a third portion 160C. The first portion 160A allows longitudinal movement of the projection 176 into the channel 158. The second portion 160B allows a combination of longitudinal movement and circumferential movement of the projection in the channel. The second portion of the channel includes an inclined surface 161 that is configured to slidingly cam the projection 176 to bring the base closer to the cap and torque is applied to the cap and/or base. The projection includes a first camming surface 177A and a second camming surface 177B which facilitate the movement of the projection through the second portion of the channel and allow sliding of the projection on the walls of the channel 158. In some embodiments as shown in FIG. 11A, the first camming surface 177A, second camming surface 177B, and inclined surface 161 are parallel to one another to facilitate sliding. The third portion 160C allows circumferential movement of the projection in the channel toward the closed end.

In the first state of the closure as shown in FIG. 11A, the projection 176 is disposed at the first portion 160A of the channel 158. The first portion of the channel allows longitudinal movement of the projection into the channel as shown by the dashed arrow. That is the projection may enter the first portion of the channel by moving the base toward the cap or vice versa. As the projection is moved into the channel 158, the second camming surface 177B is configured to contact a wall of the channel. The angle of the second camming surface is such that the normal force between the projection and the channel urges the projection in a circumferential direction, as will be discussed further with reference to FIG. 11B.

Figure 11B:
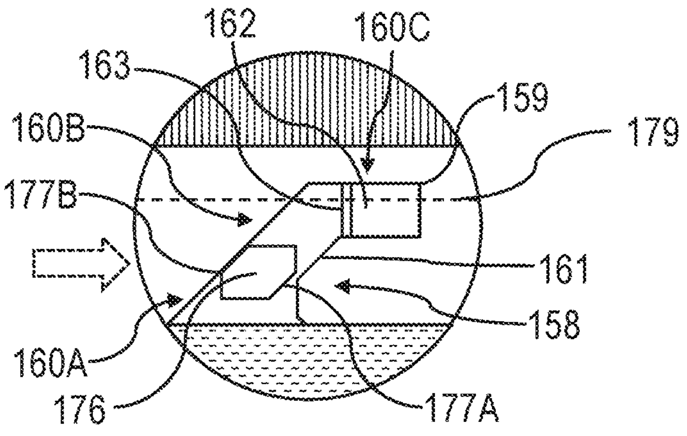
FIG. 11B depicts the closure of FIG. 11A in a second state.

FIG. 11B depicts the closure of FIG. 11A in a second state. In the second state, the second camming surface 177B is abutting the second portion 160B of the channel 158. The inclination of the second portion of the channel and the second camming surface generates a normal force that urges the projection in a circumferential direction as shown by the dashed arrow. However, this force may not be enough alone to move the projection along the channel due to friction. Accordingly, rotating the cap or base including the projection so that the first camming surface 177A engages the inclined surface 161 may assist in moving the projection along the channel 158. That is, as rotational force is applied to the projection in the direction of the dashed arrow, the inclined surface 161 may generate a normal force urging the projection a longitudinal direction further into the channel 158. Accordingly, the projection may move diagonally along the channel 158 through the second portion 160B, as the base and cap are brought closer to one another via the application of rotational force to the cap and/or base.

Figure 11C:
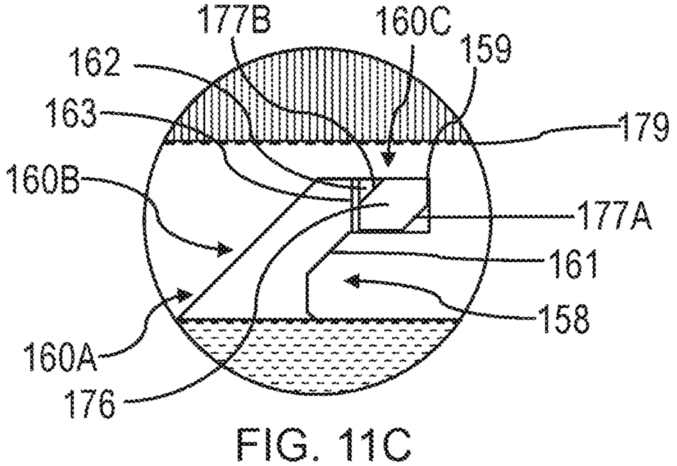
FIG. 11C depicts the closure of FIG. 11A in a third state.

FIG. 11C depicts the closure of FIG. 11A in a third state. In the third state, the projection is disposed in the recess 162 adjacent the closed end 159. As rotational force is applied to the projection 176 and the projection moves along the second portion 160B, the projection will eventually align with a third portion 160C that extends in a circumferential direction. Once aligned with the third portion, the rotational force may force the projection toward the closed end 159. When the projection reaches the closed end, a watertight seal may be formed between the cap and the base. The recess 162 may generate a tactile and/or audible click to provide feedback to the user that the container is properly closed.

To reverse the process of FIGS. 11A-11C and open the container, opposite forces may be applied to those described above. The recess may be configured to retain the projection until a threshold rotational force is applied to the cap and/or base in a second direction opposite the direction employed to move the projection into the recess. Once removed from the recess, the projection may be moved along the channel by applying continued force in the second direction to move the projection along the second portion 160B. Once the projection is disposed in the first portion 160A, longitudinal force urging the cap away from the base may be applied to remove the projection from the channel 158 entirely. Thus, in this manner, the closure of FIGS. 11A-11C may provide a reliable manner of opening and closing a container according to exemplary embodiments herein.

Figure 12:
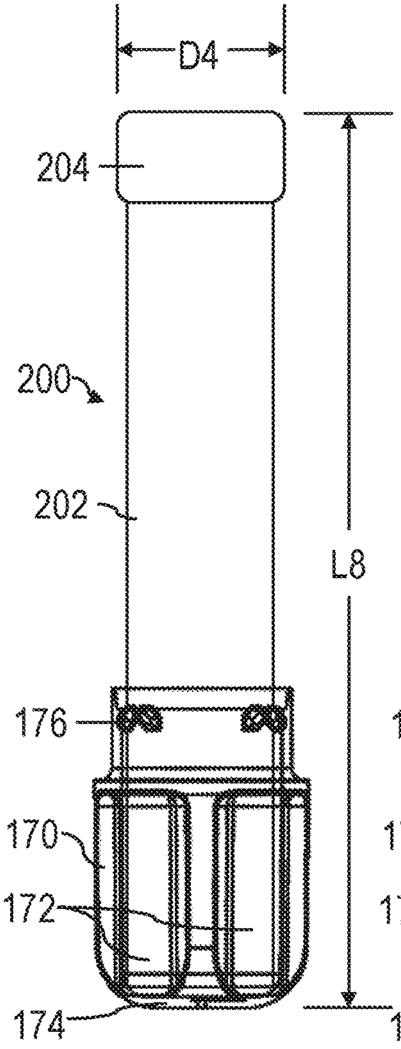
FIG. 12 depicts a side elevation view of one embodiment of a base of a container and a sample vial.
Figure 13:
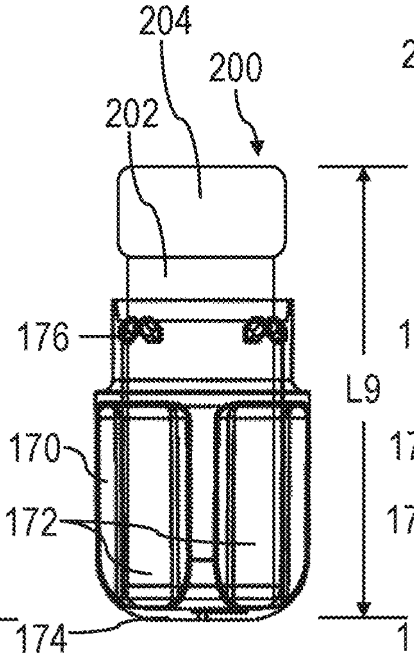
FIG. 13 depicts a side elevation view of another embodiment of a base of a container and a sample vial.
Figure 14:
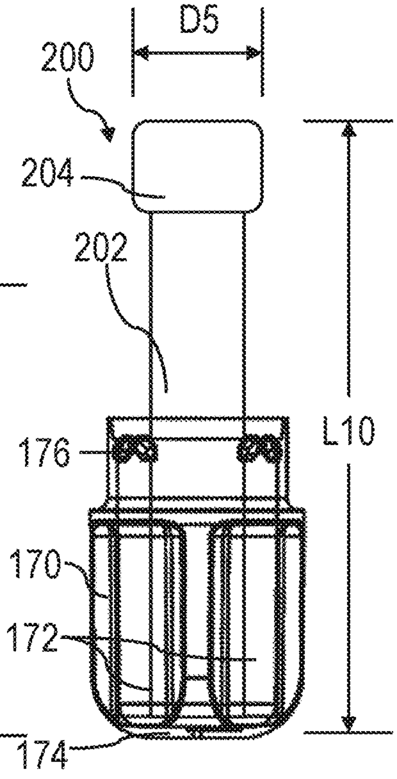
FIG. 14 depicts a side elevation view of yet another embodiment of a base of a container and a sample vial.

FIGS. 12-14 depict side elevation views of various embodiment of a base 170 of a container and a sample vial 200. According to the embodiments of FIGS. 12-14, the bases 170 are the same whereas the sample vials 200 are different from one another. FIGS. 12-14 depict the ability of a container according to exemplary embodiments described herein to accommodate many sample vials of different lengths and diameters. As shown in FIG. 12, the base 170 contains a sample vial 200 having a first sample vial length L8 and a first sample vial diameter D4. As shown in FIG. 13, the base contains a sample vial 200 having a second sample vial length L9 and the same sample vial diameter as the embodiment of FIG. 12. As shown in FIG. 14, the base contains a sample vial 200 having a third sample vial length L10 and a second sample vial diameter D5. The first, second, and third sample vial lengths are all different from one another. Additionally, the first and second sample vial diameters are different from one another. The cap associated with the base 170 of the container may be long enough to accommodate each of the sample vials shown in FIGS. 12-14. The length of the cap permits the base 170 to have a suitably small length such that each of the sample vials protrudes out of the base when the cap is removed as shown in FIGS. 12-14. Accordingly, many sample vials having different dimensions, shapes, or configurations may be employed with containers described herein, as the present disclosure is not so limited. In some embodiments, a sample vial may not protrude out of a base of a container (e.g., a length of the sample vial may be less than a base longitudinal length), as the present disclosure is not so limited.

Figure 15A:
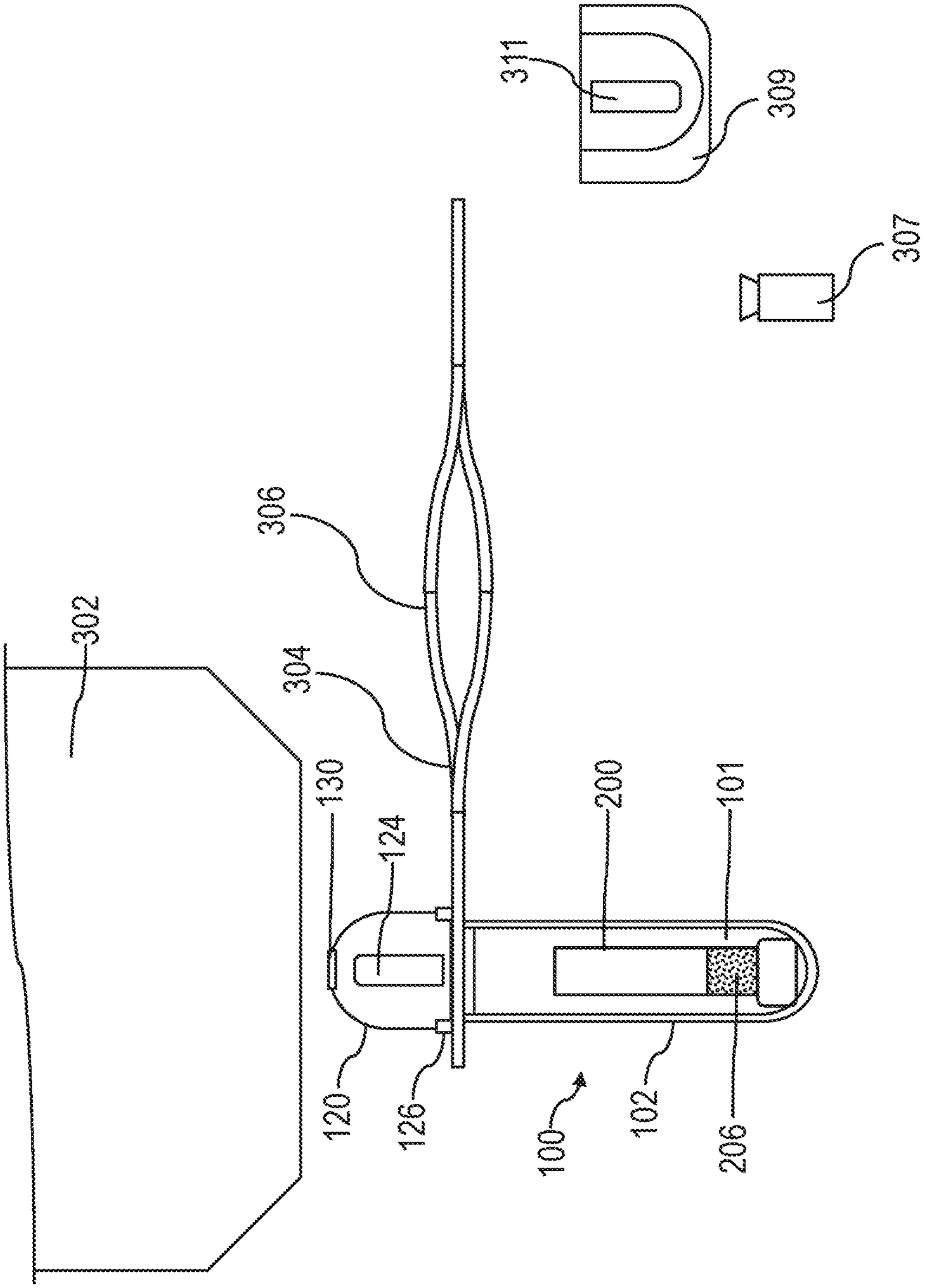
FIG. 15A depicts a schematic of one embodiment of a hopper, receiver, conveyor, imaging sensor, and container in a first state.
Figure 15B:
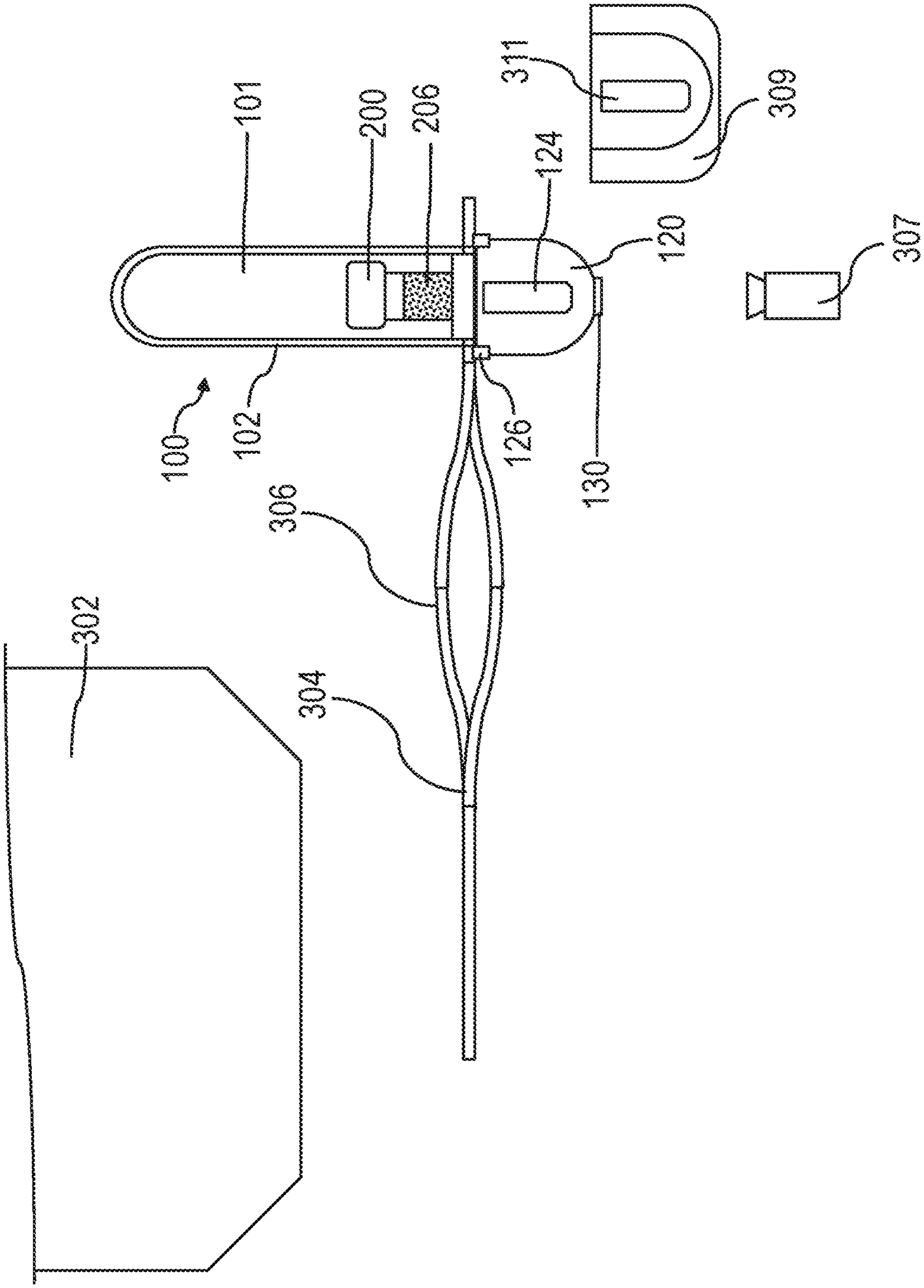
FIG. 15B depicts the hopper, receiver, conveyor, imaging sensor, and container of FIG. 15A in a second state.
Figure 15C:
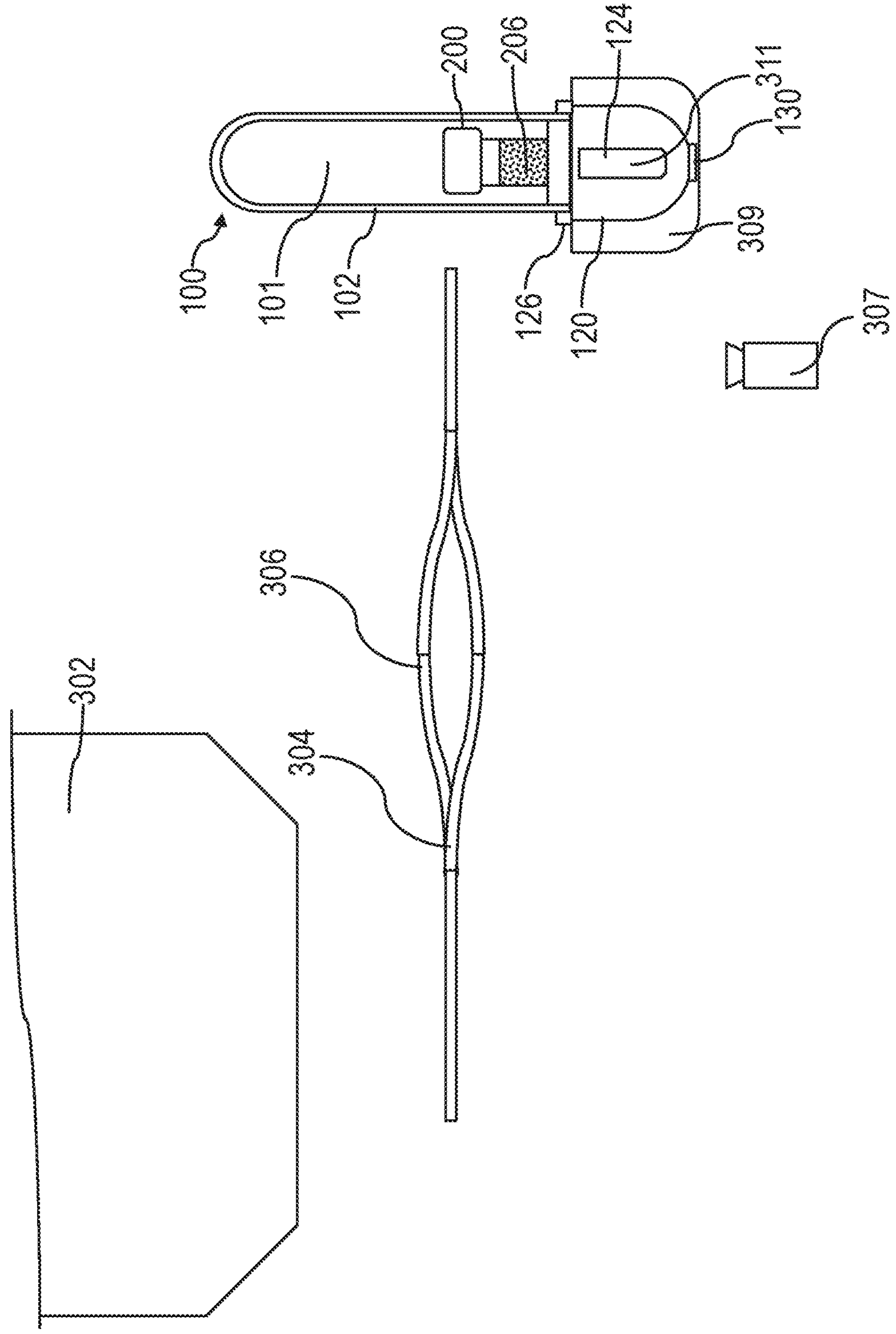
FIG. 15C depicts the hopper, receiver, conveyor, imaging sensor, and container of FIG. 15A in a third state.

The following figures and description relate to various systems and processes that may form a part of an accessioning system, according to some embodiments. FIGS. 15A-15C depict a schematic of one embodiment of a hopper 302, receiver 304, conveyor receptacle 309, imaging sensor 307, and container 100 through three states of transferring the container from the hopper to the conveyor receptacle 309. As shown in FIG. 15A, the hopper 302 is configured to receive a plurality of the containers 100, where the container each include a sample vial 200 having a sample 206. The hopper sequentially delivers the containers to the receiver 304. In some embodiments as shown in FIG. 15A, the receiver may be configured as a transporter track. In some embodiments, the receiver is configured to engage a flange 126 of a base 120 of the container to support the container 100. In the embodiment of FIG. 15A, the hopper is configured to provide the containers to the receiver in an inverted orientation, with the base 120 above a cap 102 of the container. Accordingly, the receiver 304 includes an orienting portion 306 which is configured to reorient the container in an upright orientation. The conveyor receptacle 309 is configured to receive the base 120, so the orienting portion 306 ensures the container is in an appropriate orientation such that the base may be received by the receptacle 309.

In the second state shown in FIG. 15B, the container 100 has passed through the orienting portion 306 and is now in an upright orientation, with the base 120 positioned below the cap 102. Accordingly, the base 120 is in an appropriate upright orientation to be received and retained in a receptacle 309 by gravity. As shown in FIG. 15B, the imaging sensor 307 is directed toward the base 120. In particular, the imaging sensor is directed toward an identification marker 130 disposed on the base 120. The imaging sensor may be configured to read the identification marker 130 and may obtain information about the container 100 and/or sample 206. Reading the identification marker may also ensure that the base 120 is in an appropriate orientation to be received by the receptacle. In some embodiments, the imaging sensor may communicate information from the identification marker to a processor.

In some embodiments, the imaging sensor 307 may be configured to detect a color of a container cap 102 or container base 120 that corresponds to a sample vial type. In some embodiments, depending on the color of the portion of the container 100, a processor of the accessioning system may flag the container 100 for prioritized accession. In some embodiments, the processor may employ the information obtained by the imaging sensor 307 to index a particular container on a conveyor (e.g., a position of the receptacle 309). In some embodiments, the accessioning system may store containers having a particular color for accession at a certain point in time. In some such embodiments, the accessioning system may be configured to process containers having a particular color in series. While in the embodiment of FIGS. 15A-15C the imaging sensor 307 is positioned between a hopper 302 and a receptacle 309, in other embodiments a color of the container may be detected by an imaging sensor at any point in an automated accessioning system, as the present disclosure is not so limited.

According to the embodiment of FIGS. 15A-15C, the base 120 includes an external base key 124. The receptacle 309 includes a corresponding receptacle key 311 configured to engage the external base key. Additionally, the receptacle 309 has a shape matching that of the base, such that the base may be received and supported inside of the receptacle 309. The engagement between the external base key and the receptacle key may allow torque transmission between the base and the receptacle.

In the third state of FIG. 15C, the base 120 is disposed inside of the receptacle 309. In some embodiments, the base may drop from the receiver 304 into the receptacle by gravity. In other embodiments, a gripper may grasp and place the base into the receptacle from the receiver. Once the base is received in the receptacle, a conveyor may move the container 100 through the remainder of an accessioning process. In some embodiments, once the base is disposed in the receptacle, the cap 102 of the container may be removed (e.g., by a decapper).

Figure 16:
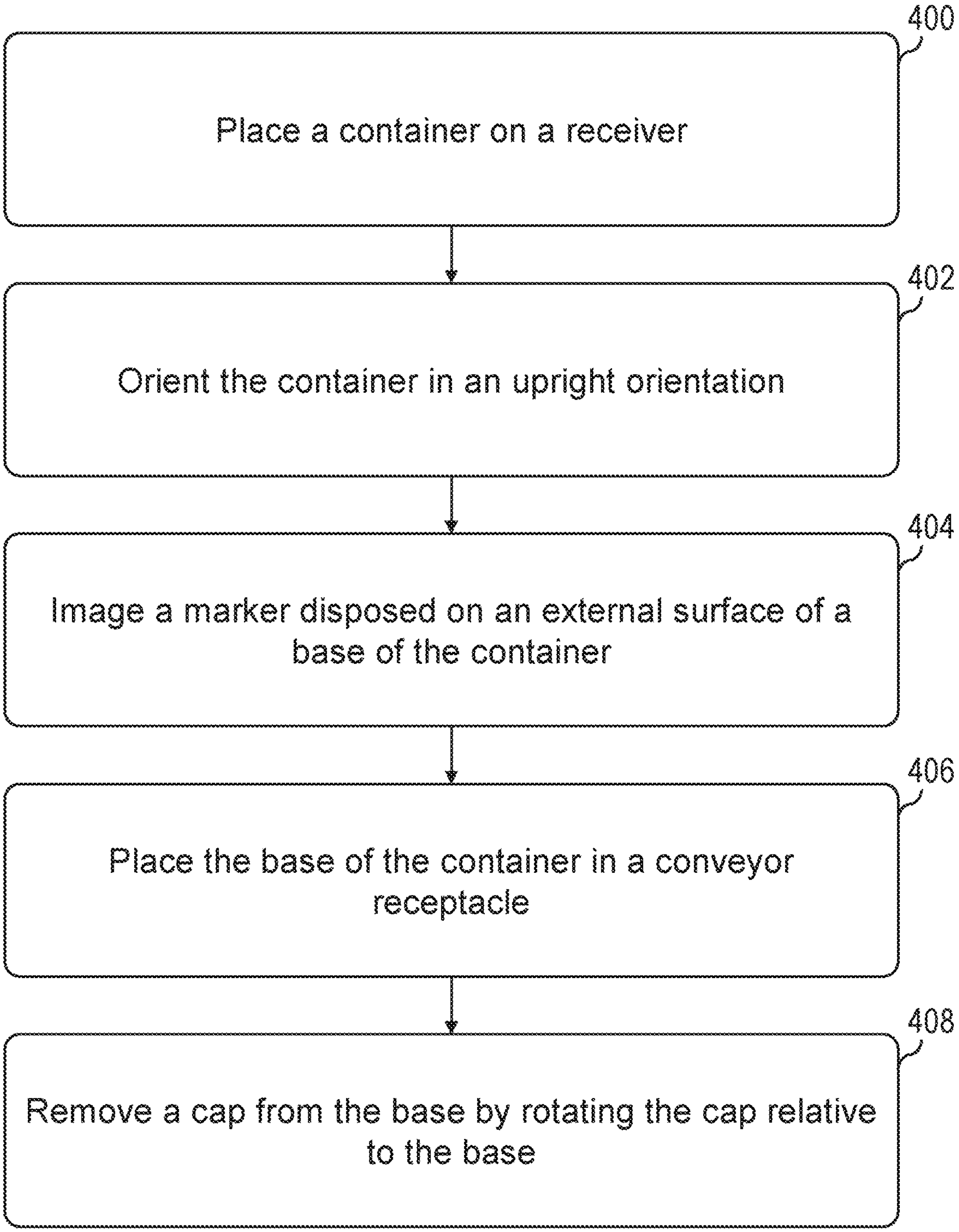
FIG. 16 is a flow chart for one embodiment of a method of operating a container accessioning system.

FIG. 16 is a flow chart for one embodiment of a method of operating a container accessioning system. In block 400, a container is placed on a receiver. In some embodiments, a hopper may place a container directly onto a receiver. In other embodiments, a user may place a container onto the receiver. In some embodiments the receiver may be a transporter track, gripper, or other suitable arrangement which moves the container. In block 402, the container is oriented in an upright orientation. In the upright orientation, the base of the container may be positioned below a cap of the container. In some embodiments, orienting the container may include flipping or rotating the container. In block 404, a marker disposed on a base of the container is imaged. The imaging of the marker may provide information to a processor controlling an accessioning process. In some embodiments, imaging the marker may function as a check that the container is in the appropriate upright position, as the marker may be unreadable if the sample vial is not in the upright orientation. In block 406, the base of the container is placed in a conveyor receptacle. In block 408, a cap is removed from the base by rotating the cap relative to the base. In some embodiments, such a rotation may be performed by a gripper.

Figure 17A:
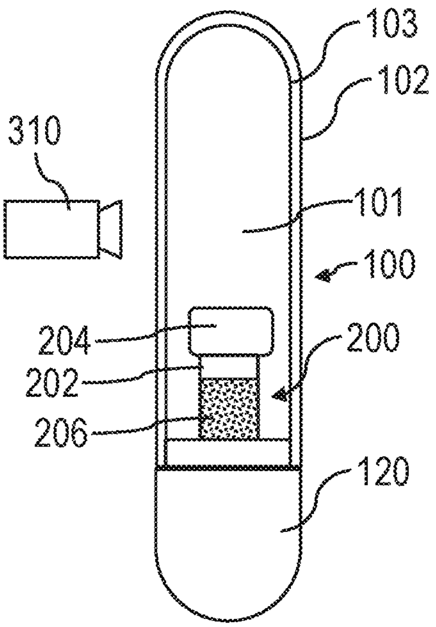
FIG. 17A is a side schematic of one embodiment of a container, sample vial, and imaging sensor in a first state.
Figure 17B:
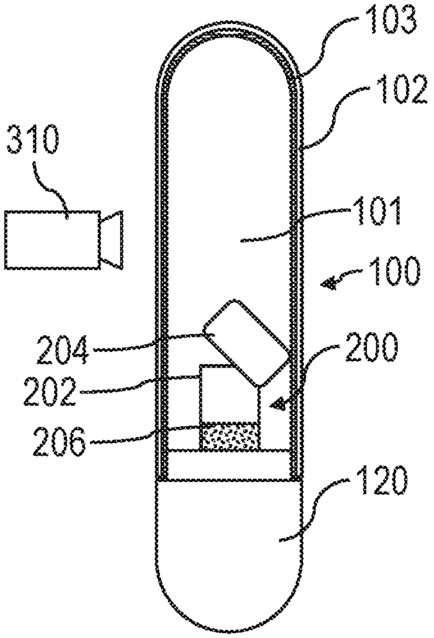
FIG. 17B is a side schematic of the container, sample vial, and imaging sensor of FIG. 17A in a second state.

FIG. 17A is a side schematic of one embodiment of a container 100, sample vial 200, and imaging sensor 310 (e.g., a camera) in a first state, and FIG. 17B is a schematic of the same in a second state. In the embodiment of FIGS. 17A-17B, the container 100 includes a hydrochromic indicator 103 disposed in an internal volume 101 of the container. The hydrochromic indicator is configured to irreversibly change color when exposed to liquid, such that the past or current presence of a liquid, solution, or other substance in the container 100 may be detected. In some embodiments, the hydrochromic indicator includes a desiccant (not shown) configured to absorb the liquid, solution, or other substance in the container 100. As shown in FIG. 17A, the imaging sensor is directed at a cap 102 of the container. In the embodiment of FIGS. 17A-17B, the hydrochromic indicator is disposed in the cap 102, such that exposure of the internal volume 101 to liquid may change the color of at least an interior wall of the cap.

In the state of FIG. 17A, the hydrochromic indicator 103 is in a first state, where these is no liquid disposed in the internal volume 101. A sample vial cap 204 is secured to sample vial body 202, such that a liquid sample 206 is retained in the sample vial 200. Accordingly, when imaged by the imaging sensor 310, the cap is translucent and the internal volume 101 may be observed. The imaging sensor may pass information to a processor, which may determine that the hydrochromic indicator is in a first state and no leak or spill of the sample 206 has occurred (e.g., by software executing on one or more computing devices, such as a computer having the processor configured to execute the software) based on the information (e.g., one or more images) from the imaging sensor. Accordingly, the processor may allow and/or cause the cap 102 of the container to be removed and for the sample vial to continue through an accessioning process.

In the state of FIG. 17B, the hydrochromic indicator 103 is in a second state, where there is liquid freely disposed in the internal volume 101. The sample vial cap 204 has released from the sample vial body 202, allowing the sample 206 to spill into the internal volume 101. Accordingly, the hydrochromic indicator has changed color in response to the exposure to liquid. As a result, the cap effectively turns opaque at least on an interior wall of the cap. Accordingly, when imaged by the imaging sensor, the imaging sensor may not be able to image the internal volume, but may see the color or presence of the hydrochromic indicator. This information may be provided to a processor and may be employed to determine that the hydrochromic indicator is in the second state. Accordingly, the processor may flag the container for removal from the accessioning system, and may prevent removal of the cap 102 of the container to avoid any spills or contamination in the accessioning system. In some embodiments, a container including a hydrochromic indicator in a second state may be removed to a quarantine location for cleaning and/or further processing, thereby allowing other containers without leakage to continue through the accessioning system.

Figure 18A:
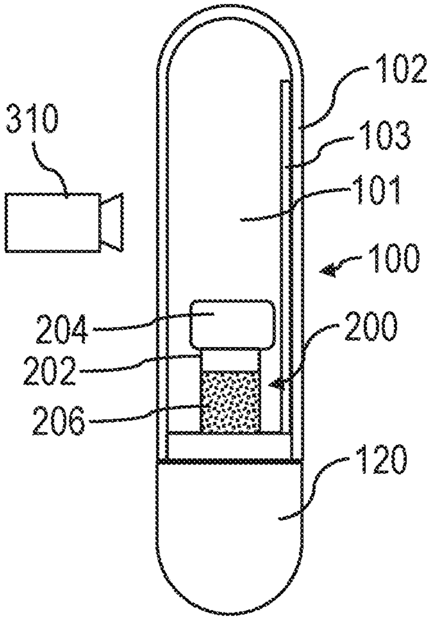
FIG. 18A is a side schematic of another embodiment of a container, sample vial, and imaging sensor in a first state.
Figure 18B:
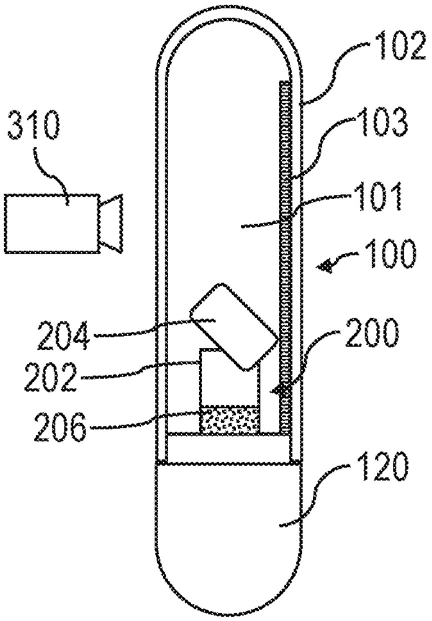
FIG. 18B is a side schematic of the container, sample vial, and imaging sensor of FIG. 18A in a second state.

FIG. 18A is a side schematic of another embodiment of a container 100, sample vial 200, and imaging sensor 310 (e.g., camera) in a first state, and FIG. 18B is a schematic of the same in a second state. The embodiment of FIGS. 18A-18B is similar to that of FIGS. 17A-17B. However, the difference lies in the arrangement of the hydrochromic indicator 103. Whereas the hydrochromic indicator was disposed throughout the cap in the embodiment of FIGS. 17A-17B, the hydrochromic indicator of FIGS. 18A-18B is disposed in only a portion of the cap 102. Accordingly, regardless of the state of the hydrochromic indicator, at least a portion of the cap may remain translucent so that the internal volume of the container may be observed by a user or by the imaging sensor 310.

In the state of FIG. 18A, the hydrochromic indicator 103 is in a first state, where there is no liquid disposed in the internal volume 101. A sample vial cap 204 is secured to sample vial body 202, such that a liquid sample 206 is retained in the sample vial 200. Accordingly, when imaged by the imaging sensor 310, hydrochromic indicator 103 disposed in the internal volume 101 may be observed. The imaging sensor may pass information to a processor, which may determine that the hydrochromic indicator is in a first state and no leak or spill of the sample 206 has occurred (e.g., by software executing on one or more computing devices, such as a computer having the processor configured to execute the software) based on the information (e.g., one or more images) from the imaging sensor. Accordingly, the processor may allow and/or cause the cap 102 of the container to be removed and for the sample vial to continue through an accessioning process.

In the state of FIG. 18B, the hydrochromic indicator 103 is in a second state, where there is liquid freely disposed in the internal volume 101. The sample vial cap 204 has released from the sample vial body 202, allowing the sample 206 to spill into the internal volume 101. Accordingly, the hydrochromic indicator has changed color in response to the exposure to liquid. When imaged by the imaging sensor, the imaging sensor may see the color or presence of the hydrochromic indicator in the second state. This information may be provided to a processor and may be employed to determine that the hydrochromic indicator is in the second state. Accordingly, the processor may flag the container for removal from the accessioning system, and may prevent removal of the cap 102 of the container to avoid any spills or contamination in the accessioning system.

While in the embodiments of FIGS. 17A-18B the cap is configured to be translucent and the hydrochromic indicator is disposed in the cap, other arrangements are contemplated. In other embodiments, the base may be translucent and include the hydrochromic indicator. In some embodiments, both the base and the cap may be translucent and include the hydrochromic indicator. In some embodiments, the container may include a transparent window, such that neither the cap nor the base is fully translucent. In some embodiments, the cap and base may be opaque. In such an embodiment, at least a portion of the container may include a hydrochromic indicator formed in a wall of the container, such that the wall of the container irreversibly changes color or otherwise indicates when an internal volume of the container is exposed to liquid. Of course, a hydrochromic indicator may be included in a container in any suitable manner detectable by an imaging sensor, as the present disclosure is not so limited.

In some embodiments, an imaging sensor may be configured to image a sample vial disposed within a container. For example, the container may be translucent or transparent such that the sample vial is visually accessible through a wall of the container. The imaging sensor may provide information regarding the sample vial, and a sample contained within the sample vial, to at least one processor of an accessioning system. In some embodiments, the at least one processor may determine an expected outcome of the sample vial based on the appearance of the sample vial. For example, using a suitable technique such as image processing, machine learning, or machine vision, the at least one processor may make a determination regarding a characteristic of the sample vial which may affect the handling of that sample vial. For example, the at least one processor may determine a color of the sample within the sample vial. If the color of the sample vial does not meet a predetermined standard (e.g., within a threshold of a desired color for the sample type), the sample vial may be flagged (e.g., within a database) for removal from the accessioning system. In some embodiments, such a flagging may include moving a container holding the sample vial to a quarantine location. As another example, the at least one processor may determine a viscosity of a sample within the sample vial (e.g., based on a movement of the fluid sample within the sample vial). As still another example, the at least one processor may determine a consistency of a sample within the sample vial. According to one such example, the at least one processor may determine if the sample is fully liquid or if the sample has one or more solids or clots (e.g., blood clots in a blood sample). According to another such example, the at least one processor may determine if the sample is uniform or if the sample is stratified into layers or is otherwise non-uniform. As still another example the at least one processor may determine a fill (e.g., quantity of liquid) within the sample vial. Like the example provided with respect to color, if these characteristics fall outside of an expected range, the sample vial may be flagged (e.g., within a database) for removal or separate processing. In some embodiments, the flagging of a sample may include updating a laboratory information management system (LIMS) with information regarding the determined issue with the sample (e.g., based on one or more standards for the sample). In some cases, such information may be provided to the submitter of the sample to provide feedback on why a sample was not accessioned or used. In some embodiments, if at least one processor does not determine any characteristics of the sample falling outside of an expected range, the at least one processor may flag the container as passing or otherwise proceeding in an accessioning process.

Figure 19:
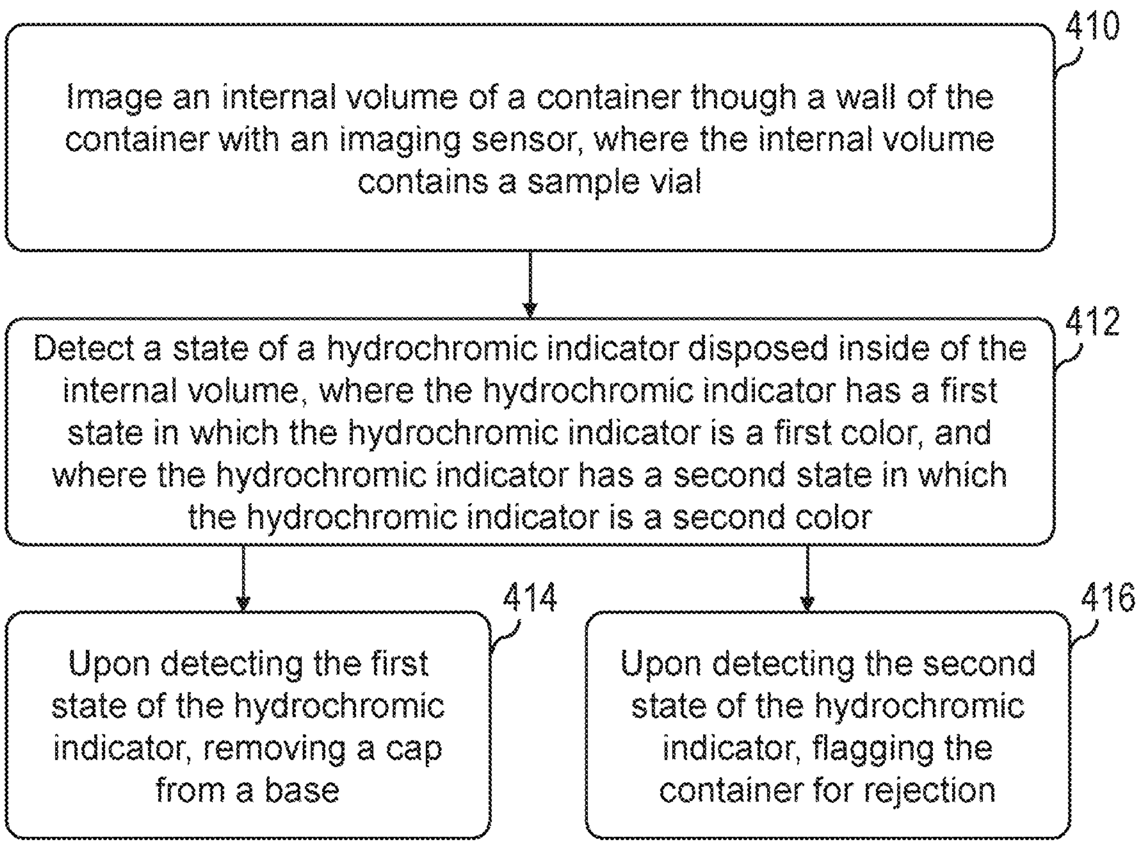
FIG. 19 is a flow chart for another embodiment of a method of operating a container accessioning system.

FIG. 19 is a flow chart for another embodiment of a method of operating a container accessioning system. In block 410, an internal volume of a container is imaged through a wall of the container with an imaging sensor. In block 412, the state of a hydrochromic indicator is detected (e.g., by a processor). The hydrochromic indicator has a first state in which the hydrochromic indicator is a first color, and the hydrochromic indicator has a second state in which the hydrochromic indicator is a second color. In some embodiments, the hydrochromic indicator may form a distinct pattern or symbol in the second state. Two options follow block 410. In block 414, if the first state is detected, a cap of the container may be removed from a base of the container. In block 416, if the second state of the hydrochromic indicator is detected, the container may be flagged for rejection. In some embodiments, if the second state of the hydrochromic indicator is detected, the container may be physically removed from the accessioning system and placed in a quarantine location.

Figure 20A:
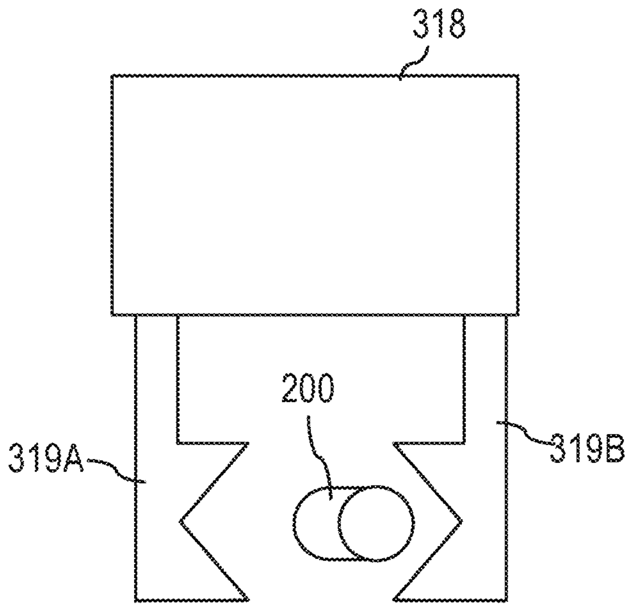
FIG. 20A is a plan schematic of one embodiment of a gripper and a sample vial in a first state.
Figure 20B:
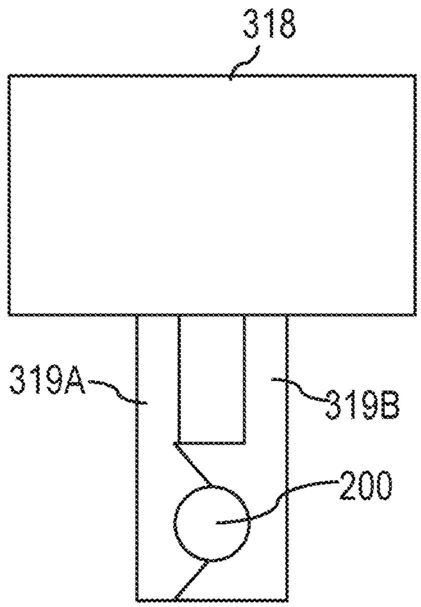
FIG. 20B is a plan schematic of the gripper and sample vial of FIG. 20A in a second state.

FIG. 20A is a plan schematic of one embodiment of a gripper 318 and a sample vial 200 in a first state, and FIG. 20B depicts the same in a second state. As shown in FIGS. 20A-20B, the gripper 318 may include a first arm 319A and a second arm 319B. The first arm and second arm may be configured to move toward one another to grasp the sample vial 200. In some embodiments as shown in FIGS. 20A-20B, the first arm and second arm are shaped such that the gripper centers the sample vial between the arms. For example, as shown in FIGS. 20A-20B, the first arm and second arm include inclined notches that urge a sample vial of any size toward a central axis between the first and second arms. That is, when force is applied to grasp a sample vial, the inclined notches generate normal forces centering the sample vial between the arms, as shown in FIG. 20B. In this manner, the gripper 318 can accommodate a variety of sample vials having different diameters. Of course, a gripper may have any suitable configuration to center sample vials of different diameters, as the present disclosure is not so limited. In addition to centering the sample vials based on diameter, the gripper 318 may also align a sample vial with a vertical axis, as described further with reference to FIGS. 21A-21B.

Figure 21A:
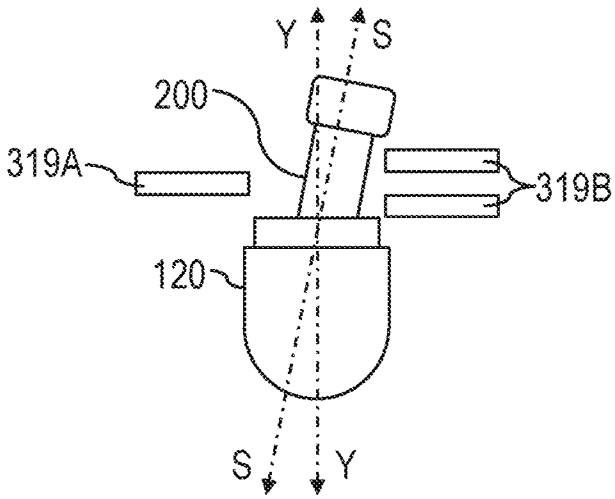
FIG. 21A is a side schematic the gripper and sample vial of FIG. 20A.
Figure 21B:
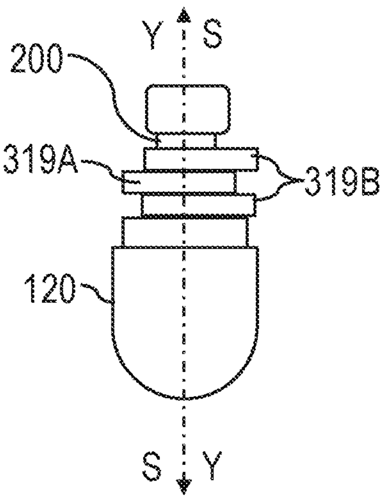
FIG. 21B is a side schematic of the gripper and sample vial of FIG. 20B.

FIG. 21A is a side schematic the gripper 318 and sample vial of FIG. 20A, and FIG. 21B is a side schematic of the gripper 318 and sample vial of FIG. 20B. As shown in FIG. 21A, in some cases the sample vial 200 may be inclined along an axis S compared with a vertical axis Y. This may be due to the length of the sample vial being greater than the length of a base 120 of a container, as well as a diameter of the sample vial being less than an internal diameter of the base. Accordingly, it may be desirable to appropriately orient the sample vial such that it can be appropriately placed in a sample rack. In some embodiments as shown in FIGS. 21A-21B, a gripper may include a first arm 319A and second arm 319B configured to align a longitudinal axis of the sample vial with a vertical axis Y. That is, as shown in FIG. 21B, the grasping of the sample vial may move the sample vial to a vertically aligned orientation, whether that be upright in the case of FIG. 21B or inverted.

Figure 22A:
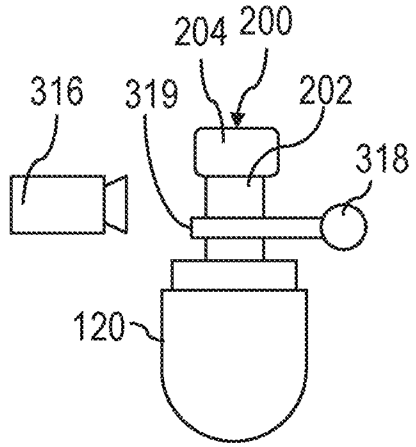
FIG. 22A is a side schematic of one embodiment of a container, sample vial, gripper, and imaging sensor in a first state.
Figure 22B:
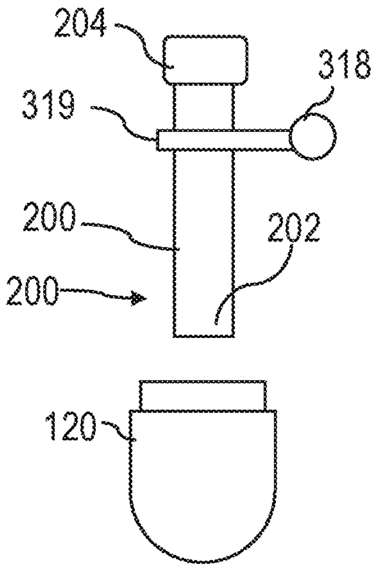
FIG. 22B is a side schematic of the container, sample vial, gripper, and imaging sensor of FIG. 22A in a second state.
Figure 23A:
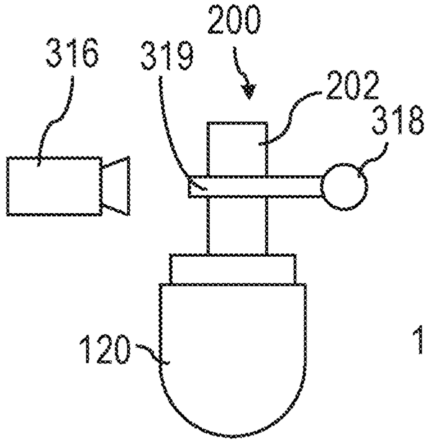
FIG. 23A is a side schematic of another embodiment of a container, sample vial, gripper, and imaging sensor in a first state.
Figure 23B:
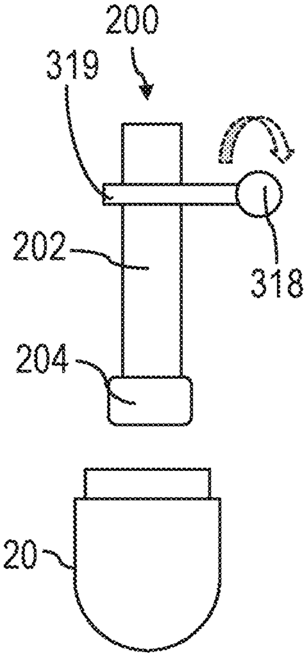
FIG. 23B is a side schematic of the container, sample vial, gripper, and imaging sensor of FIG. 23A in a second state.
Figure 23C:
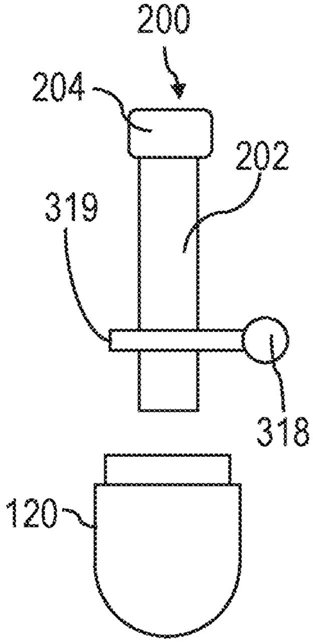
FIG. 23C is a side schematic of the container, sample vial, gripper, and imaging sensor of FIG. 23A in a third state.

FIGS. 22A-23C depict two processes for extracting a sample vial 200 out of a base 120 of a container according to exemplary embodiments herein. The process shown in FIGS. 22A-22B is for sample vials in an upright orientation, where a sample vial cap 204 is positioned above a sample vial body 202. The process shown in FIGS. 23A-23C is for sample vials in an inverted orientation, where a sample vial cap 204 is positioned below a sample vial body 202. As shown in FIGS. 22A-23C, an accessioning system includes a gripper 318 including arms 319, as well as an imaging sensor 316. The imaging sensor is configured to observe the sample vial 200. The imaging sensor 316 may provide information to a processor which is configured to detect the orientation of the sample vial. The processor may then command the gripper to operate differently depending on the orientation of the sample vial.

In the state shown in FIG. 22A, the sample vial 200 is disposed in the base 120 in an upright orientation. Accordingly, the sample vial cap 204 is visible to the imaging sensor 316. A processor may use the visibility of the sample vial cap determine that the sample vial is in an upright orientation based on the information provided by the imaging sensor. As a result, as shown in FIG. 22B, the processor may command the gripper 318 to grasp the sample vial 200 and lift the sample vial out of the base 120. The gripper 318 in FIG. 22B does not reorient the sample vial, as the sample vial is in the desired upright orientation.

In the state shown in FIG. 23A, the sample vial 200 is disposed in the base 120 in an inverted orientation. Accordingly, the sample vial cap 204 is not visible to the imaging sensor 316. A processor may use the absence of the sample vial cap to determine that the sample vial is in the inverted orientation based on the information provided by the imaging sensor. As a result, as shown in FIG. 23B, the processor may command the gripper 318 to grasp the sample vial 200 and lift the sample vial out of the base 120. The gripper 318 in FIG. 23B also reorients the sample vial to the desired upright orientation, as shown by the dashed arrow. FIG. 23C depicts the results of the reorientation by the gripper, which flips the sample vial to the upright orientation. Accordingly, once the sample vial is in the upright orientation as shown in FIG. 23C, the sample vial may be transported to an appropriate sample rack. In this manner, a sample vial may be extracted and reoriented regardless of the orientation of the sample vial inside of a container.

While in the embodiments of FIGS. 22A-23C an upright orientation of the sample vial is desired, any desired orientation may be employed. Accordingly, a gripper may be commanded to rotate a sample vial to any desired angle based on the determination of an initial orientation by a processor using information from an imaging sensor, as the present disclosure is not so limited.

Figure 24:
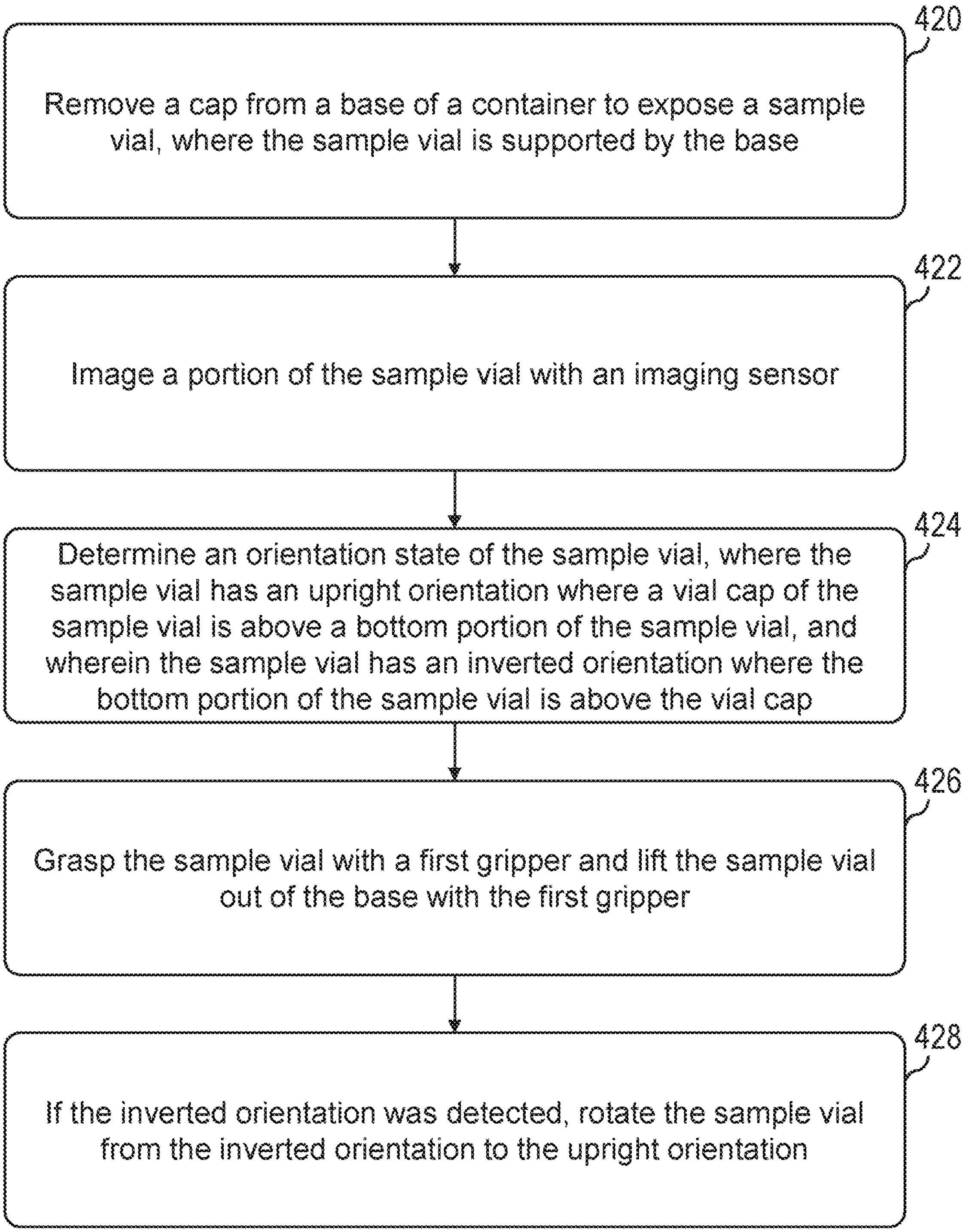
FIG. 24 is a flow chart of yet another embodiment of operating a container accessioning system.

FIG. 24 is a flow chart of yet another embodiment of operating a container accessioning system. In block 420, a cap is removed from a base of a container to expose a sample vial, where the sample vial is supported by the base. In block 422, a portion of the sample vial may be imaged by an imaging sensor. In some embodiments, a portion of the sample vial protruding out of the base may be imaged. In some other embodiments, a portion of the sample vial may be imaged through the base. In such an embodiment, the base may be transparent such that the sample vial may be imaged. In some such embodiments, the sample vial may not protrude out of the base. In block 424, an orientation state of the sample vial is determined (e.g., by software executing on one or more computing devices, such as a computer having at least one processor configured to execute the software) based on the information (e.g., one or more images) from the imaging sensor. The sample vial may be in an inverted orientation where a sample vial cap is below a sample vial body (e.g., a bottom portion of a sample vial) or in an upright orientation where a sample vial cap is above a sample vial body. In some embodiments, determining the orientation of the sample vial may be based on the detection of a sample vial cap protruding out of the base. In block 426, the sample vial is grasped with a first gripper and is lifted out of the base. In block 428, if the inverted orientation of the sample vial is detected, the sample vial is rotated from the inverted orientation to the upright orientation.

Figure 25:
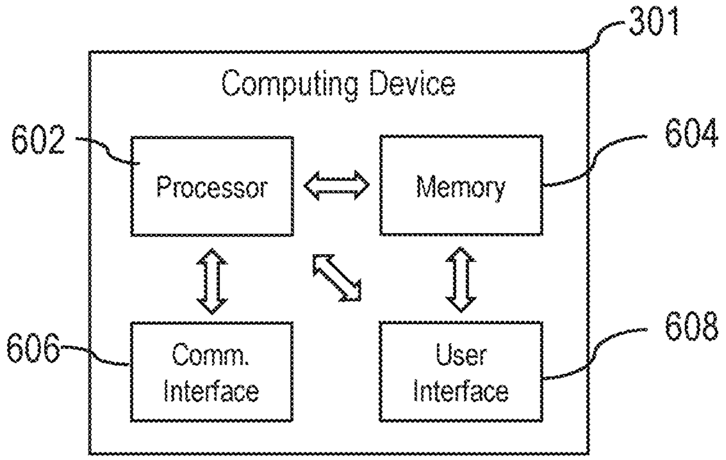
FIG. 25 is a schematic of one embodiment of a computing device.

FIG. 25 is a computer processor and memory diagram for a computing device 301 according to exemplary embodiments described herein. As shown in FIG. 25, the computing device includes a processor 602, memory 604, a communications interface 606, and an optional user interface 608. The processor 602 is configured to execute instructions that may be implemented in processor-executable software stored on the memory 604. The memory may be non-volatile and store software for execution by the processor. The communications interface may allow the processor to receive information and/or transmit commands to various components of an accessioning system. In some embodiments, the communications interface may implement a wired or wireless communications protocol. In some embodiments, the computing device includes a user interface 608, which may allow a user to input commands to the processor 602, update software stored on the memory 604, and/or receive alerts or information from the processor.

Figure 26:
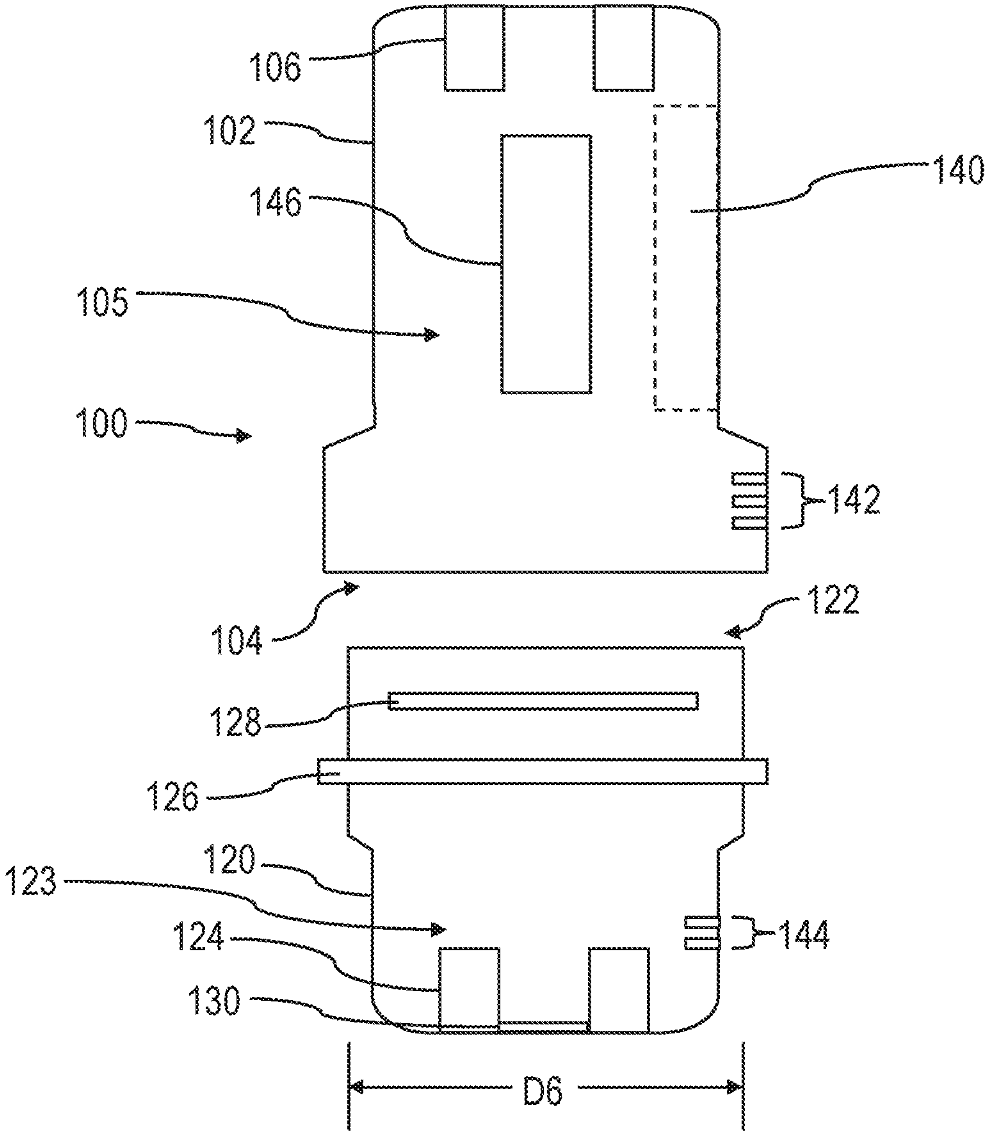
FIG. 26 is a side schematic of another embodiment of a container in an empty state.

FIG. 26 is a side schematic of another embodiment of a container 100 in an empty state. As shown in FIG. 26, the container 100 includes a cap 102 and a base 120. The cap is configured to be removably coupled to the base to create an internal volume. According to the embodiment of FIG. 26, the cap 102 includes a cap internal volume 105 accessible via a cap opening 104. Similarly, the base 120 includes a base internal volume 123 accessible via a base opening 122. The cap 102 also includes an external cap key 106, which is configured to engage a decapper to allow the decapper to apply torque to the cap. Similarly, the base 120 includes an external base key 124 configured to engage a conveyor to allow the conveyor to apply torque to the base (or alternatively, resist torque applied to the conveyor by the base). Like previously discussed embodiments, the external cap key and external base key are configured as notches formed in the cap and base, respectively.

According to the embodiment of FIG. 26, the cap 102 of the container 100 is configured to receive the base 120 such that an inner diameter of the cap is greater than an outer diameter of the base. As shown in FIG. 26, the base includes a closure 128 and a flange 126. The closure 128 of the depicted embodiment is a protrusion which is configured to engage the cap 102 to removably couple the cap to the base. In particular, the cap 102 may include a receptacle configured to receive the protrusion such that the base is coupled to the cap. To remove the base from the cap, a threshold force may be applied to the cap 102 in a direction away from the base 120. Accordingly, the closure of FIG. 26 may be a longitudinal closure, where force applied along a longitudinal axis of the container may be employed to open or close the container 100.

In some embodiments as shown in FIG. 26, the container 100 includes an environmental control 140. The environmental control 140 is configured to maintain an environmental condition of the internal volume of the container 100. In the particular embodiment of FIG. 26, the environmental control is configured as a cold pack configured to maintain the temperature of the internal volume below a predetermined temperature. In some embodiments, the environmental control may be configured to be frozen before use, and the environmental control may be reused in this manner multiple times. In some embodiments, the environmental control may be chemically activated when the base 120 is coupled to the cap 102. For example, the base may apply pressure to a portion of the environmental control to initiate a chemical reaction. In such an embodiment, the environmental control may be removable after the container is used. While in the embodiment of FIG. 26 the environmental control is located in the cap 102, in other embodiments the environmental control may be located in the base 120, as the present disclosure is not so limited.

In the embodiment of FIG. 26, the cap 102 and the base 120 approximately share a container diameter of D6. Compared with previously discussed embodiments, the diameter D6 is a greater proportion of the overall length of the container 100. Such an arrangement may be appropriate to accommodate wider types of sample vials (e.g., urine sample vials such as urine cups, stool sample vials such as stool sample containers, etc.). In some embodiments, the container diameter D6 is between 40 and 100 mm (e.g., 50 mm, 60 mm, 70 mm, etc.). Of course, any suitable diameter for a container may be employed, as the present disclosure is not so limited.

In the embodiment of FIG. 26, the base 120 includes an identification marker 130. The identification marker 130 is configured to convey information to an imaging sensor (e.g., a camera). The identification marker may convey information to a processor. As shown in FIG. 26, the identification marker is disposed on a bottom exterior surface of the base 120. As shown in FIG. 26, the container also includes a cap manufacture identifier 142 and a base manufacture identifier 144. According to the embodiment of FIG. 26, the cap manufacture identifier and base manufacture identifier are engraved into the cap and base, respectively. As shown in FIG. 26, the cap manufacture identifier includes three marks, whereas the base manufacture identifier only includes two marks. The number of marks may indicate the number of times the cap or base has been used individually. According to the depicted embodiment, the cap has been employed in an accessioning system, such as automated accessioning system 300, three times, whereas the base has been employed in an accessioning system, such as automated accessioning system 300, twice. Each time through an accessioning system, an additional mark may be added to track the total number of uses of the cap and the base. In some embodiments, the manufacture identifier and base manufacture identifier may also convey information to a sensor (e.g., an imaging sensor) regarding the cap or base, respectively, including, but not limited to, date of manufacture, location of manufacture, and dimensions.

According to some embodiments as shown in FIG. 26, the container may also include a shipping identifier 146. The shipping identifier is configured as a label and is configured to convey shipping information regarding the container, including, but not limited to, origin, destination, sender identity, recipient identity, time in transit, and weight. In some embodiments, the shipping identifier may be read by an imaging sensor of an automated accessioning system. While in the embodiment of FIG. 26 the container 100 includes an identification marker 130, cap manufacture identifier 142, base manufacture identifier 144, and shipping identifier 146, in other embodiments any suitable number of markers and/or identifiers may be employed to convey information to a user or automated accessioning system, as the present disclosure is not so limited.

FIGS. 27A-27D depict a process for assembling a container including a sample vial 200 according to exemplary embodiments herein. In some cases, the process shown in FIGS. 27A-27D may be performed in an automated manner to send an unused sample vial to an end user. In some embodiments, the process may allow the sample vial and container to be shipped without any additional packaging (e.g., boxes, bags, wrapping, etc.). However, in other embodiments, the sample vial and container may be shipped within packaging (e.g., a box, bag, wrapping, etc.).

As shown in FIGS. 27A-27D, a container assembly system may include a first gripper 350 including arms 351. The container assembly system of FIGS. 27A-27D may also include a second gripper 352. Of course, in other embodiments, a container assembly system may include any suitable number of grippers, as the present disclosure is not so limited. In some embodiments, as shown in FIGS. 27A-27D, the container assembly system may include an imaging sensor 356. The imaging sensor is configured to observe the container 100. The imaging sensor 356 may provide information to a processor which is configured to detect a closed or open state of the container. The processor may then determine whether or not the container is ready to be shipped based on the open or closed state detected by the processor. In some embodiments, the processor may flag in memory a container that is in the closed state as ready for shipment.

Figure 27A:
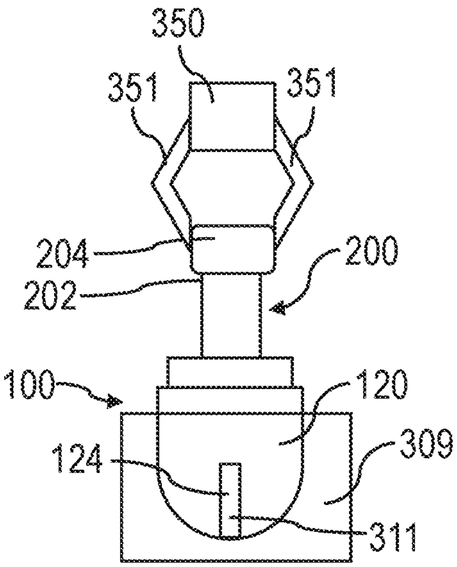
FIG. 27A is a side schematic of another embodiment of a container and sample vial in a first state.

In the state shown in FIG. 27A, the start of a process of assembling a container 100 is shown according to exemplary embodiments described herein. As shown in FIG. 27A, the first gripper 350 is holding a sample vial 200. The first gripper 350 is configured to place the sample vial 200 in the base 120. According to the embodiment of FIG. 27A, the first gripper 350 places the sample vial in the base in an upright orientation (e.g., with a sample vial cap 204 positioned above a bottom portion of the sample vial 200). Of course, the first gripper 350 may place the sample vial in the base 120 in any desired orientation, as the present disclosure is not so limited. Once the sample vial 200 is placed in the base 120, the base 120 supports the sample vial.

As shown in FIG. 27A, the base 120 is placed in a receptacle 309. The receptacle 309 may be configured to support the base and inhibit rotation of the base while held by the receptacle. In some embodiments, the receptacle 309 has a shape matching that of the base, such that the base may be received and supported inside of the receptacle 309. The base 120 may be held in the receptacle 309 by gravity. As shown in FIG. 27A, the base 120 may include an external base key 124. The receptacle 309 may include a corresponding receptacle key 311 configured to engage the external base key. The engagement between the external base key and the receptacle key may allow torque transmission between the base and the receptacle. In some embodiments, the receptacle 309 may be positioned on a conveyor track, such that the base 120 may be moved along the conveyor track.

In some embodiments, additional objects or devices may be placed in the base 120 prior to the container 100 being closed. For example, in some embodiments, paperwork (e.g., instructions), one or more labels, one or more desiccants, one or more environmental controls, and/or one or more indicators (e.g., hydrochromic indicators) may be placed in the base 120 along with the sample vial by the first gripper 350 or another gripper. In the particular embodiment of FIGS. 27A-27D, a hydrochromic indicator 103 is placed in the base 120 along with the sample vial 200. However, in other embodiments, any desired object or combination of objects may be placed in the base 120 before the container 100 is closed, as the present disclosure is not so limited. In some embodiments, an inactivated environmental control may be placed in the base. For example, a chemically activated cold pack may be placed in the base which is configured to be activated by a user prior to the user closing the container for return shipping or other delivery of a sample in the container.

Figure 27B:
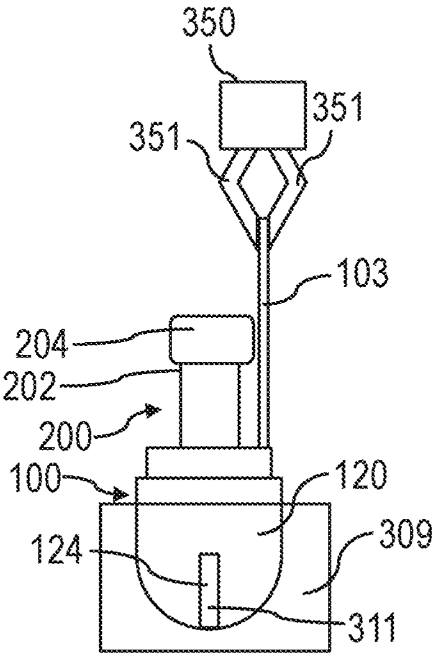
FIG. 27B is a side schematic of the container and sample vial of FIG. 27A in a second state.

In the state shown in FIG. 27B, the first gripper 350 is grasping a hydrochromic indicator 103. In the state of FIG. 27B, the first gripper 350 has placed the hydrochromic indicator 103 in the base 120. The hydrochromic indicator is configured to irreversibly change color when exposed to liquid, such that the past or current presence of a liquid, solution, or other substance in the container 100 may be detected. In some embodiments, the hydrochromic indicator includes a desiccant, such that the hydrochromic indicator including the desiccant is capable of absorbing a liquid, solution, or other substance and changing color when coming into contact with the liquid, solution, or other substance. When the container is assembled in the process of FIGS. 27A-27D, the sample vial 200 may not contain any liquid. Accordingly, the hydrochromic indicator may be configured to be replaced or left in the base 120 by an end user when the sample is placed in the sample vial 200. In other embodiments, a hydrochromic indicator may be formed as a part of the container, in which case no hydrochromic indicator may be placed in the base 120.

Figure 27C:
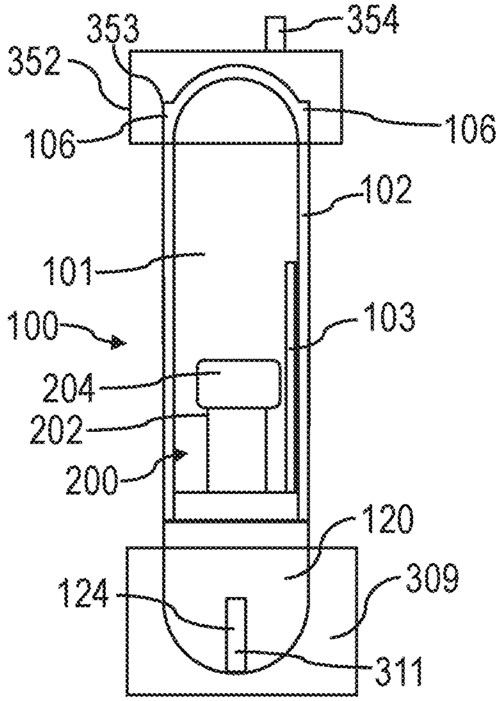
FIG. 27C is a side schematic of the container and sample vial of FIG. 27A in a third state.

In the state shown in FIG. 27C, the first gripper 350 has been moved away from the container 100. A cap 102 is coupled to the base by a second gripper 352. According to the embodiment of FIG. 27C, the second gripper may be formed as a vacuum gripper configured to grasp the cap by forming a vacuum through a vacuum port 354. According to such an embodiment, the cap may be supported in the second gripper 352 by the vacuum against the force of gravity while the cap is moved into position. As shown in FIG. 27C, the cap includes an external cap key 106. The second gripper 352 has a receptacle key 353 with a corresponding shape that is configured to engage the external cap key. Accordingly, torque may be transmitted between the second gripper 352 and the cap 102. In the embodiment of FIGS. 27A-27D, the second gripper 352 is configured to rotate the cap 102 relative to the base 120 to couple the cap 102 to the base 120. In some embodiments, a closure between the cap 102 and the base 120 may include threads, projection(s) and receptacle(s), or another rotary closure. Of course, in other embodiments, the closure may be a longitudinal closure, as the present disclosure is not so limited. In such embodiments, the second gripper 352 may be configured to apply a longitudinal force to the cap 102 in a direction of the base 120. In some embodiments, coupling the cap 102 to the base 120 may form a watertight seal. While in the embodiment of FIGS. 27A-27D the second gripper is configured as a vacuum gripper, in other embodiments the second gripper may be configured an any suitable type of gripper, as the present disclosure is not so limited. For example, in some embodiments, the second gripper may include arms configured to grasp the cap 102.

Figure 27D:
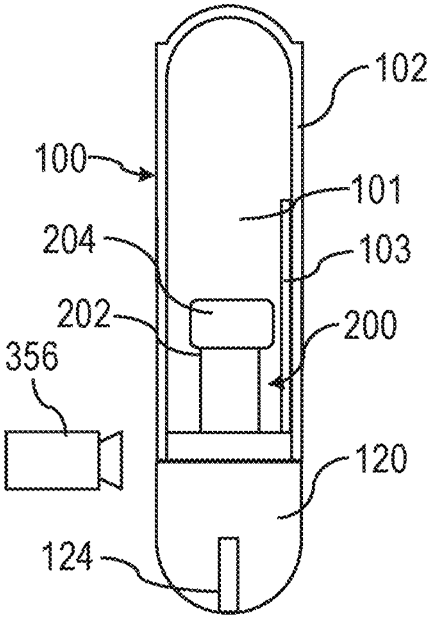
FIG. 27D is a side schematic of the container and sample vial of FIG. 27A in a fourth state.

In the state shown in FIG. 27D, the container 100 is closed with the cap 102 coupled to the base 120. Accordingly, the sample vial 200 and hydrochromic indicator 103 are captured in an internal volume 101 of the container. In some embodiments, a container assembly system may be configured to verify that a container 100 is properly closed before releasing the container to be shipped. In the embodiment of FIGS. 27A-27D, the container assembly system includes an imaging sensor 356 configured to image the container 100. The imaging sensor 356 may provide information to a processor which may be configured to determine if the container is closed. In some embodiments, the processor may determine if the container is closed based on an alignment between markers formed on an exterior of the container 100. In other embodiments, the processor may employ image processing and/or machine learning to determine if a container is closed. In one such embodiment, the container 100 may include a line on each of the cap 102 and the base 120 (for example, see FIGS. 10A-10B). When the container is properly closed, the lines align on the exterior of the container 100 to create a stripe. The line on each of the cap 102 and the base 120 may be of a same or different color. In some embodiments, the image processing and/or machine learning looks for the stripe on the container 100 to make sure that the container 100 is closed. Moreover, in some embodiments, a container 100 which is determined to be closed properly is released to be shipped and a container 100 which is determined to not be closed properly is not released to be shipped. Of course, any suitable technique may be employed, as the present disclosure is not so limited. If the processor determines that the container 100 is closed, the container may be allowed to be moved out of the container assembly system (e.g., to be shipped or delivered). In some embodiments, if the processor determines that the container is not closed, the container may be moved to a separate area for further processing. In some embodiments, detecting the container is open (e.g., not closed) may cause the processor to command a gripper to remove a cap of the container and recouple the cap to the base. In some embodiments, detecting the container is open may cause the processor to command a gripper to remove the container from a conveyor track (e.g., by lifting the container out of the receptacle 309). In some embodiments, detecting the container is closed may cause the processor to allow the container to remain in the receptacle on a conveyor track.

It should be noted that while in the process shown in FIGS. 27A-27D a sample vial is placed in a container, in other embodiments other objects may be placed in the base

120, and the present disclosure is not so limited in this regard. For example, in some embodiments, the container may be configured to receive sanitary products, documents, medicines, or other objects.

Figure 28:
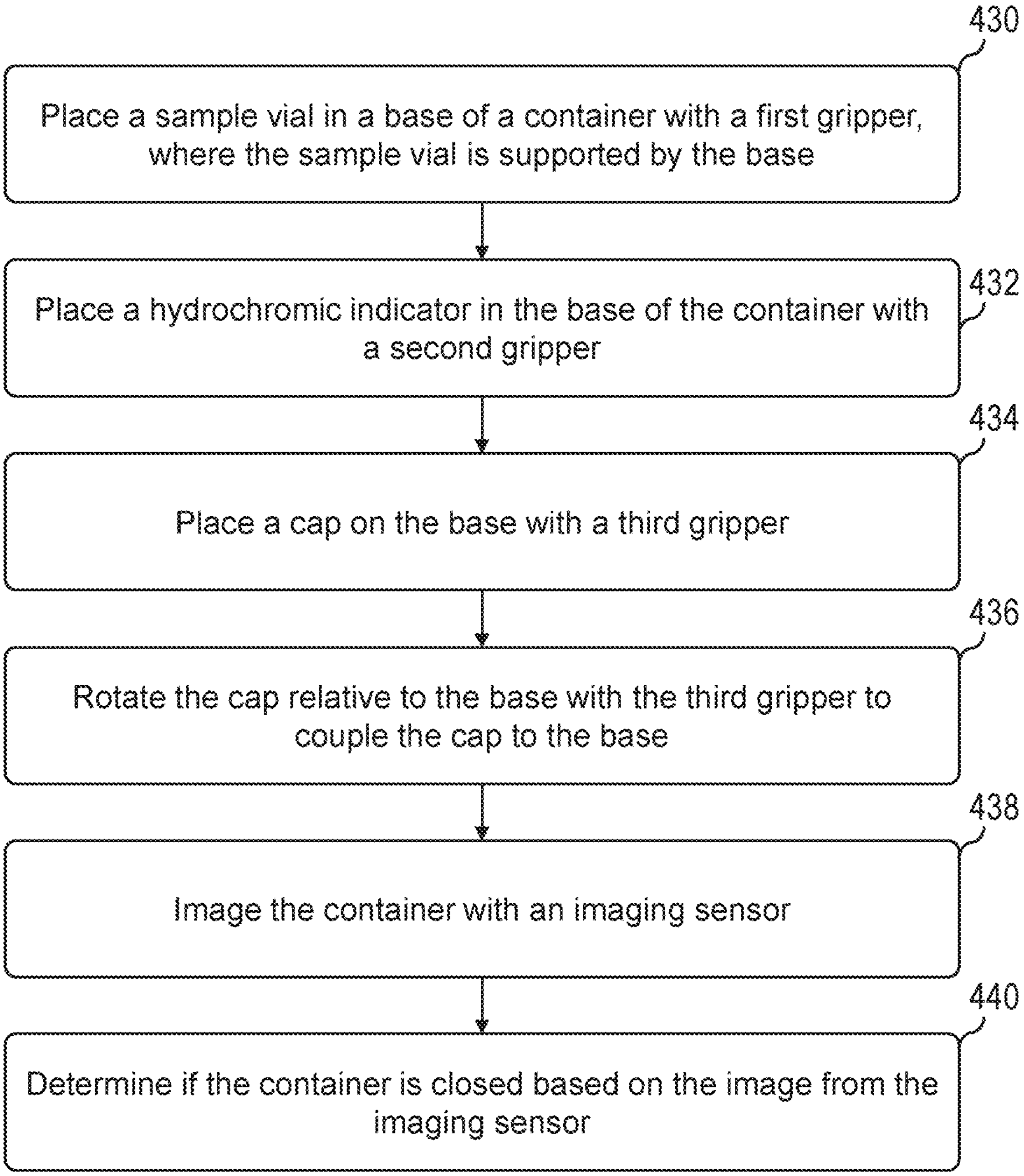
FIG. 28 is a flow chart for one embodiment of a method of assembling a container.

FIG. 28 is a flow chart for one embodiment of a method of assembling a container. In block 430, a sample vial is placed in a base of a container with a first gripper. The sample vial may be supported by the base once the base receives the sample vial. In block 432, a hydrochromic indicator is placed in the base of the container with a second gripper. In some embodiments, the hydrochromic indicator may be placed in the base by the first gripper. In some embodiments, no hydrochromic indicator may be placed in the base. In some embodiments, an additional object (e.g., documentation) may be placed in the base instead of or in addition to the hydrochromic indicator. In block 434, a cap is placed on the base with a third gripper. In some embodiments, the cap may be placed on the base with the first gripper or the second gripper, as the present disclosure is not so limited in this regard. In block 436, the cap is rotated relative to the base with the third gripper to couple the cap to the base. In some embodiments, coupling the cap to the base may form a watertight seal. In some alternative embodiments, the third gripper may not rotate the cap, but may apply a longitudinal force to the cap in a direction of the base. In block 438, the container is imaged with an imaging sensor (e.g., a camera). In block 440, it may be determined whether the container is closed based on the image from the imaging sensor. For example, a processor may employ image processing to determine whether the container is closed. In some embodiments, the method may further include, upon detecting the open state of the container, moving the container off of a conveyor track, and, upon detecting the closed state of the container, allowing the container to remain on the conveyor track.

While in the embodiment of FIG. 28 the method includes imaging the container in block 438 and determining whether the container is closed based on the image in block 440, in other embodiments, these steps may be optional. In some embodiments, the system may determine container closure using a different approach. For example, in some embodiments, the method may include determining a torque applied to the cap during the rotation of the cap in block 436 (e.g., with a torque sensor). According to some embodiments, the method may include determining an open or closed state of the container based on the torque applied to the cap exceeding a threshold torque. In some such embodiments, no imaging sensor may be employed to assist in determining the container is in a closed state or open state. In some embodiments, the steps of blocks 438 and 440 may be employed in addition to determining if the torque applied to cap exceeds a threshold torque. Of course, in other embodiments, any suitable process may be employed to determine an open or closed state of a container using any number of sensors during a container assembly method, as the present disclosure is not so limited.

Figure 29:
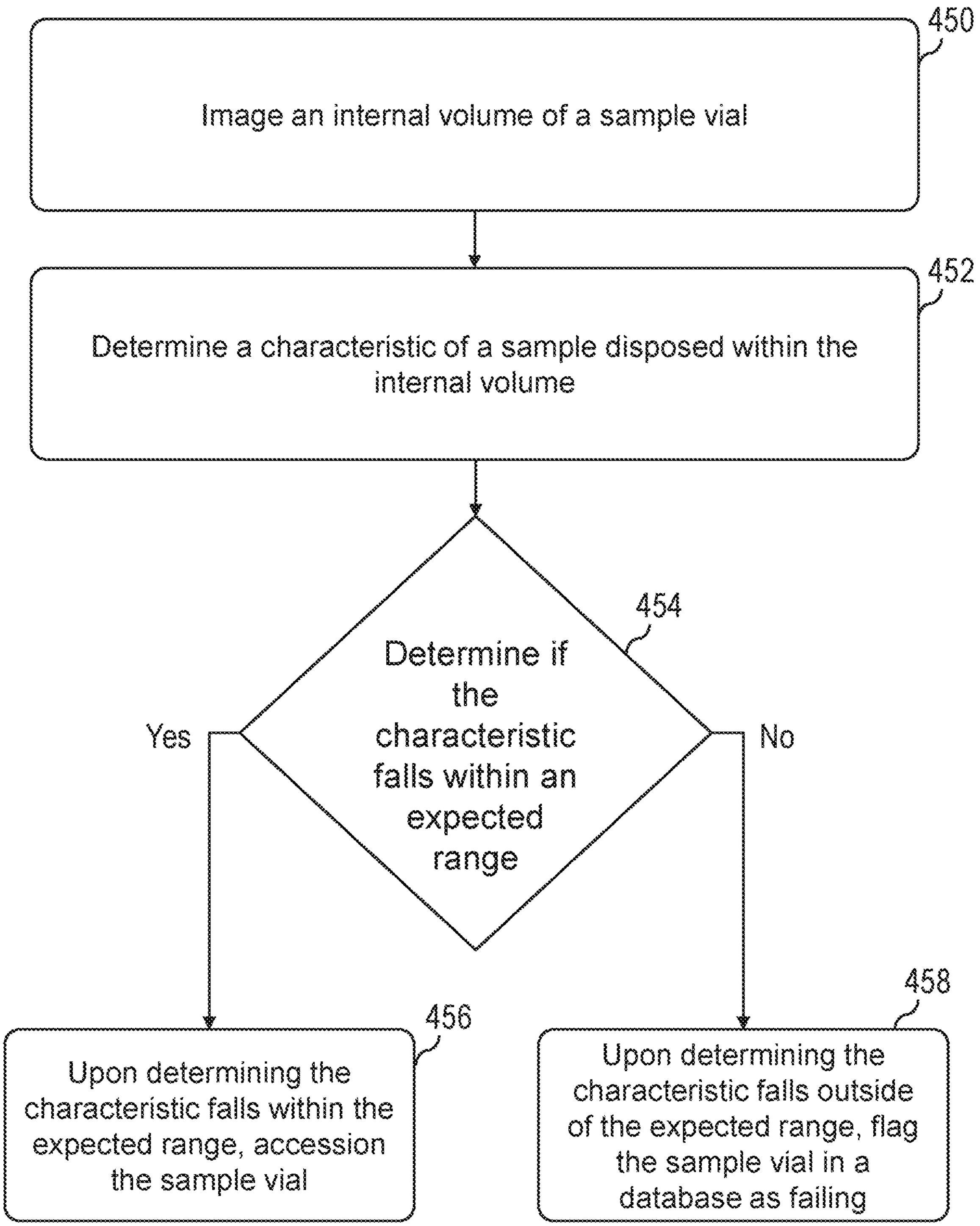
FIG. 29 is a flow chart for an embodiment of operating a container accessioning system.

FIG. 29 is a flow chart for an embodiment of operating a container accessioning system. In block 450, an internal volume of a sample vial is imaged. The internal volume may be imaged with an imaging sensor, which may provide the image to at least one processor. In some embodiments, a wall of the sample vial may be translucent or transparent such that the internal volume of the sample may be imaged externally. In some embodiments, a cap of the sample vial may be removed to image the internal volume. In some embodiments, the sample vial may be removed (e.g., by a gripper, etc.) from the container to be imaged, and optionally replaced in the container once the imaging is complete. In some embodiments, the sample vial may be imaged through a translucent or transparent wall of a container holding the sample vial. In block 452, a characteristic of a sample disposed within the internal volume may be determined. For example, using a suitable technique such as image processing, machine learning, or machine vision, at least one processor may make a determination regarding a characteristic of the sample. The characteristic of the sample may include color, volume (e.g., fill level), and viscosity, though any visually identifiable characteristic may be employed. In block 454, it is determined if the characteristic falls within an expected range. For example, in block 452, a color of the sample within the sample vial may be determined. In block 454, it may be determined if the color of the sample vial does not meet a predetermined standard (e.g., within the expected range of a desired color for the sample type). The expected range may be determined based on a particular sample type, and/or a trained model using training data from successful and failed samples. Depending on the outcome of the determination in block 454, the sample vial may be handled differently. In block 456, upon determining the characteristic falls outside of the expected range, the sample vial may be accessioned according to exemplary embodiments described herein. For example, the sample vial may be removed from a container, and a sample vial cap removed. In some embodiments, the sample vial may also be flagged within a database (e.g., a LIMS) as passing the check of blocks 452 and 454. In block 458, upon determining the characteristic falls outside of the expected range, the sample vial is flagged in a database as failing. In some embodiments, the flag may include the reasoning for the failure (e.g., falling outside of the expected range for the particular characteristic). In some embodiments, information associated with the flag in the database may be provided to the submitter of the sample vial. In some embodiments, the sample vial may be removed from accessioning due to the failure. For example, the sample vial may be removed from a general stream of an accessioning process and may be moved to a quarantine area. In some embodiments, the method of FIG. 29 may be repeated for any number of characteristics, such that an accessioning system can ensure a sample is viable before accessioning a sample vial.

Figure 30A:
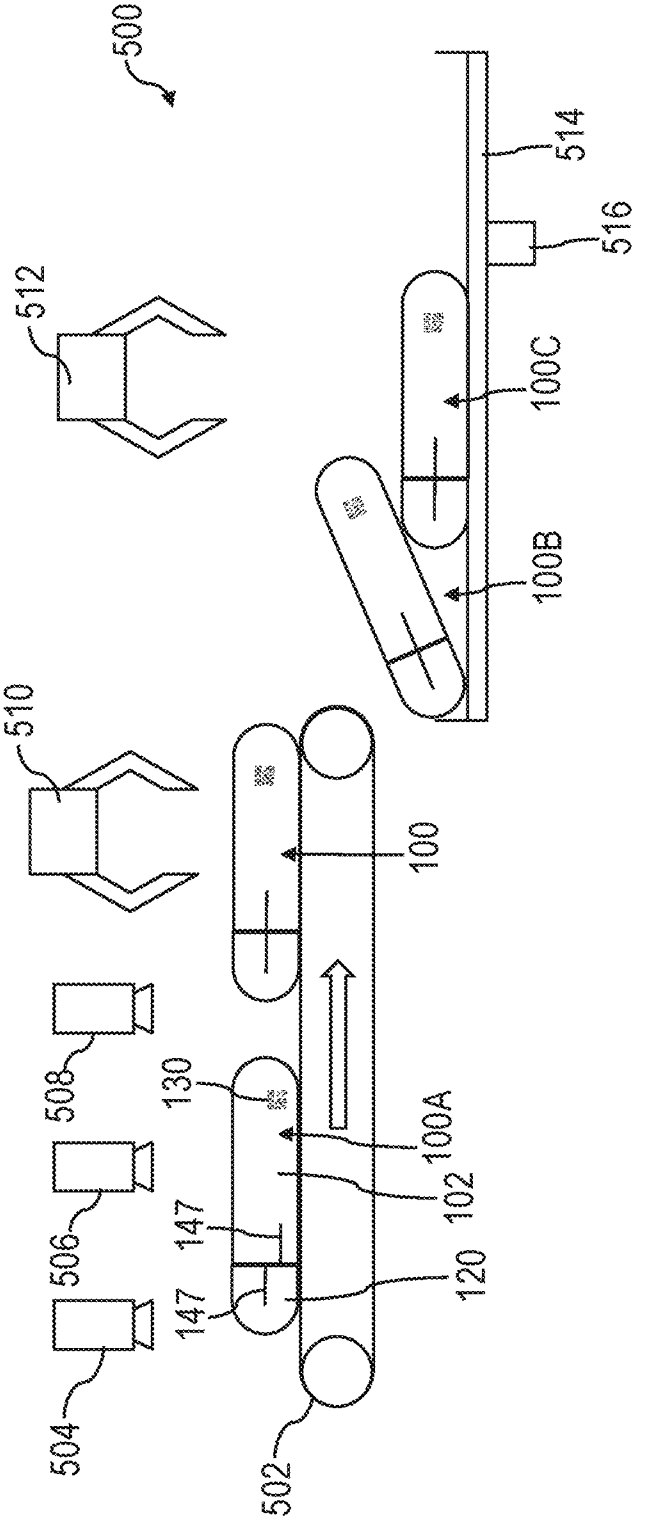
FIG. 30A depicts a schematic of one embodiment of a hopper, conveyor, imaging sensors, and containers in a first state.

FIG. 30A depicts a schematic of one embodiment of a hopper, conveyor, imaging sensors, and containers in a first state. The system 500 shown in FIG. 30A may form a part of a container accessioning system. In particular, the system of FIGS. 30A-30B may be employed as an initial stage of a container accessioning system. As shown in FIG. 30A, the system includes a conveyor 502 and a hopper 514. The conveyor 502 is arranged as a conveyor belt and may be configured to receive a plurality of containers 100 and convey them to the hopper 514. In other embodiments, other non-belt conveyor systems may be employed, as the present disclosure is not so limited. In some embodiments, the conveyor 502 is not present as part of system 500. In some such embodiments, the containers may be placed directly in the hopper 514. Disposed over the conveyor 502 is a series of imaging sensors. In particular, a first imaging sensor 504, a second imaging sensor 506, and a third imaging sensor 508 are arranged in series over the conveyor 502. In the depicted embodiment, the imaging sensors are configured to image the containers 100 disposed on the conveyor belt so that at least one processor may determine one or more characteristics of the container prior to the container reaching the hopper 514. In particular, the imaging sensors may collect information regarding the containers to ensure the samples contained within are not leaking, and therefore will not contaminate other downstream portions of an accessioning system (e.g., the hopper 514). In some embodiments where no conveyor 502 is employed, the imaging sensors may be disposed over the hopper 514 and may be configured to collect information regarding the containers within the hopper. Accordingly, in some embodiments, the processes described below with reference to the imaging sensors 504, 506, 508 and the conveyor 502 may also be employed with one or more imaging sensors and containers disposed in a hopper, as the present disclosure is not so limited.

The first imaging sensor 504 is configured to image the containers 100 disposed on the conveyor 502 to detect moisture associated with a container. The first imaging sensor may send an image to at least one processor, which may use any suitable technique, such as machine learning or imaging processing, to detect the presence of moisture on an exterior of the container 100. For example, colors associated with a sample may be detected. As another example, droplets may be detected. In some embodiments, the first imaging sensor 504 may be configured to image an internal volume of a container (e.g., through a transparent or translucent wall of the container), which may include a hydrochromic indicator as discussed with reference to some embodiments herein. In some such embodiments, at least one processor may detect the presence of moisture in an interior of the container 100 through analysis of an image of the internal volume provided by the first imaging sensor 504. For example, a specific color of the hydrochromic indicator may be detected. If at least one processor detects moisture from the information provided by the first imaging sensor 504, a first gripper 510 may be configured to remove the container in question from the conveyor 502 before the container reaches the hopper 514. The first gripper 510 may place the container in a quarantine location or otherwise remove the container from the general stream of the accessioning system. In this manner, contamination and associated cleaning of the accessioning system may be limited to the conveyor rather than downstream portions of an accessioning system. In some embodiments, the conveyor 502 may be stopped upon a detection of moisture to avoid spreading any leaked sample. In some embodiments, detection of moisture may also cause the at least one processor to flag the container in a database (e.g., a LIMS) with the information related to the detection of moisture. While in the embodiment of FIG. 30A an imaging sensor is employed, any suitable moisture sensor may be employed to detect moisture associated with the container in other embodiments, as the present disclosure is not so limited.

The second imaging sensor 506 is configured to image the containers 100 disposed on the conveyor to detect a closure status of a container. As discussed previously, in some embodiments, a container may include one or more alignment features that are visually accessible to an imaging sensor that indicate a closed status of the container. In the embodiment of FIG. 30A, each container includes lines 147, which form a stripe when aligned that is indicative of a closed container. The second imaging sensor 506 may provide information to at least one processor, which may detect whether the lines 147 are aligned and form a stripe. If the lines do form a stripe, the at least one processor may determine the container is fully closed and is allowed to proceed to the hopper 514. If the lines do not form a stripe and are offset or otherwise spaced from one another (see container 100A), the at least one processor may determine the container is not fully closed or is otherwise improperly closed. In this case, the at least one processor may cause the first gripper 510 to remove the not fully closed container from the conveyor 502 before the container reaches the hopper 514. Such a container may be placed in a quarantine location or otherwise removed from the general stream of the accessioning system. In some embodiments, detection of improper closure may also cause the at least one processor to flag the container in a database (e.g., a LIMS) with the information related to the improper closure. In some embodiments, the at least one processor may cause the first gripper 510 or another gripper or tool to fully close the container and place it back on the conveyor 502 or directly into the hopper 514.

The third imaging sensor 508 is configured to image or scan an identification marker 130 (e.g., a QR code) or another barcode. The third imaging sensor may provide information to at least one processor, which may retrieve information associated with the QR code (e.g., sample type, assay type, identification of the submitter, etc.). Such information may be employed to sort or prioritize a particular container, as discussed with reference to other exemplary embodiments described herein. For example, a container holding a sample with a limited time of viability may be prioritized for accession over a container holding a sample with a longer time of viability. The detection of a QR code or other barcode may also allow the at least one processor to update a database with information that the container was received at the accessioning system. In some embodiments, if there is no QR code or other bar code, and the container is not able to be identified, the at least one processor may cause the first gripper 510 to remove the container from the conveyor 502 prior to the container reaching the hopper 514. The unidentified container may be moved to a quarantine location or otherwise may be removed from the general stream of the accessioning system for further processing.

Figure 30B:
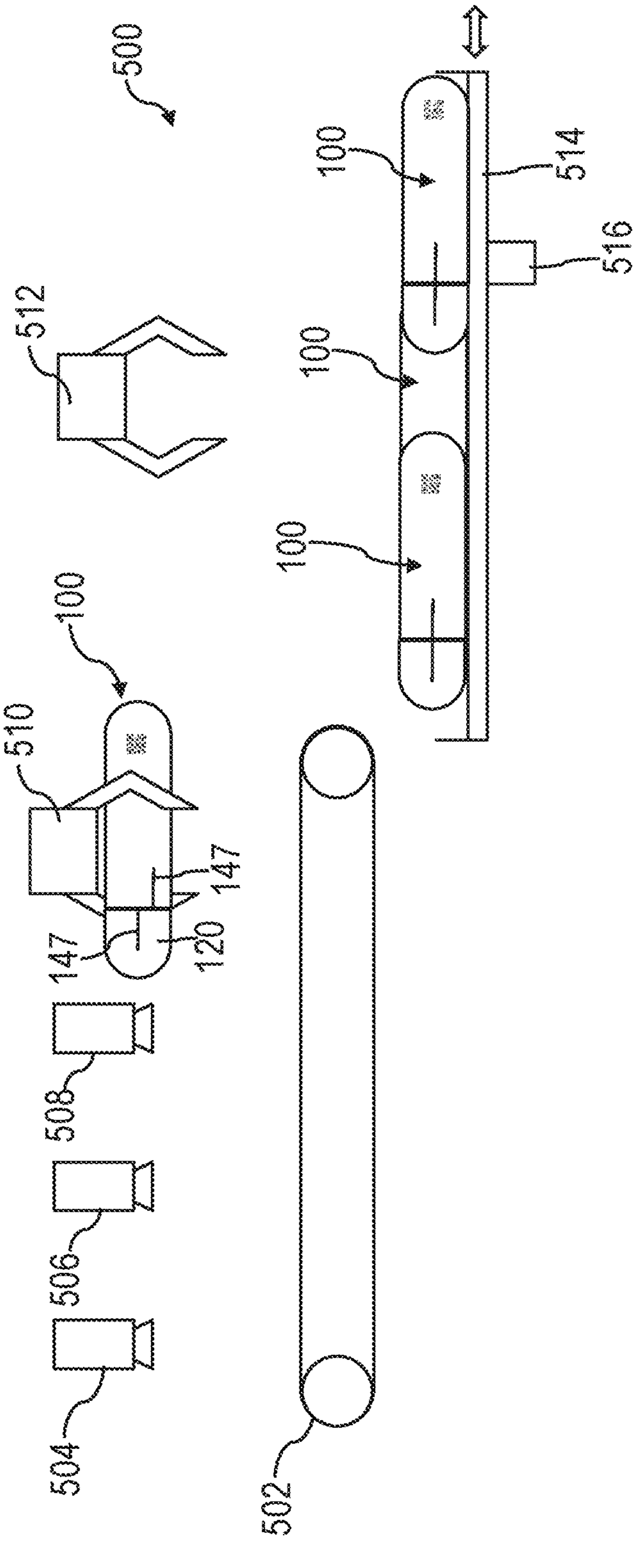
FIG. 30B depicts a schematic of the hopper, conveyor, imaging sensors, and containers in a second state.

While, in the embodiment of FIGS. 30A-30B, three imaging sensors are employed, in other embodiments any number of imaging sensors may be employed, as the present disclosure is not so limited. For example, in some embodiments a single imaging sensor may be employed. Information from the single imaging sensor may be processed (e.g., in multiple parallel threads) to make the various determinations related to the containers disposed on the conveyor. In some other embodiments, each imaging sensor may be associated with its own processor, such that each determination is performed in series. While a particular order is shown in FIGS. 30A-30B, any suitable order for imaging sensors and their associated processes may be employed, as the present disclosure is not so limited. In some embodiments, detection of a QR code or other barcode may be performed first, such that the determinations of closure and moisture may be associated with an identified container (e.g., in a database). Such an arrangement may be desirable to ensure a submitter of a sample may be notified when a container is flagged for removal from the conveyor and is not accessioned. While in the embodiment of FIGS. 30A-30B a single gripper is shown associated with the conveyor 502, in other embodiments any number of grippers may be employed, as the present disclosure is not so limited.

As shown in FIG. 30A, the hopper 514 is configured as a vibratory shake table. The hopper includes a vibratory motor 516 configured to vibrate and oscillate the hopper 514. The vibratory motor may include an eccentric mass or another suitable arrangement configured to generate vibrations. The vibration of the hopper 514 is configured to ensure the containers 100 lay flat on the hopper. As shown in FIG. 30A, a second gripper 512 is configured to pick containers from the hopper and place the containers in the next stage of an accessioning system (e.g., another conveyor, a conveyor receptacle, etc.). Ensuring the containers lay flat on the hopper may simplify the pick and place by the second gripper. In some embodiments, the second gripper may employ machine vision to identify and grasp the containers from the hoppers. In other embodiments any suitable arrangement may be employed to control the second gripper, as the present disclosure is not so limited. In some embodiments, the hopper 514 may be associated with an imaging sensor configured to detect moisture (e.g., in a similar manner to the first imaging sensor 504 described above). If moisture is detected in the hopper 514, at least one processor may stop the vibration of the hopper to inhibit the spread of any leaked sample. In some embodiments, the hopper 514 may vibrate continuously. In some embodiments, the hopper may vibrate cyclically, stopping to allow the second gripper to more easily grasp stationary containers.

The states shown in FIGS. 30A and 30B demonstrate the functionality of the system 500. In the first state shown in FIG. 30A, containers are advanced on the conveyor 502 until they are deposited in the hopper 514. As the containers move along the conveyor, the imaging sensors determine if the containers are suitable to move along in a general steam of an accessioning system by checking for moisture and closure status of each container. As shown in FIG. 30A, a container 100A is improperly closed. The lines 147 indicating closure are not aligned, meaning the container is not fully closed. At least one processor of the system may flag the container 100A for removal from the conveyor 502 before reaching the hopper 514. As also shown in FIG. 30A, containers in the hopper 514 may stack on top of one another in some instances. Container 100B is disposed at an angle on top of container 100C.

In the second state of FIG. 30B, the container 100A is removed from the conveyor by the first gripper 510 due to the detection of the misaligned lines 147. The vibratory motor 516 of the hopper 514 has been activated to vibrate the hopper. The oscillation moves the containers, allowing the container 100B to fall off of the container 100C. Accordingly, all of the containers are lying flat after the hopper is vibrated. A third container is shown behind the two front containers in FIG. 30B. In other embodiments, the hopper may accommodate any number of containers, as the present disclosure is not so limited. Once the containers are lying flat, the second gripper 512 may grasp a container from the hopper and move it to another portion of an accessioning system. In some embodiments, while the hopper is vibrated, the conveyor 502 may be stopped to avoid additional containers falling on top of the containers lying flat in the hopper. In such an embodiment, once the containers from the hopper are all removed, the conveyor may be restarted to bring additional containers to the hopper.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the embodiments described herein may be implemented as a computer program, which may be embodied in a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium). The computer program may be encoded such that, when executed on one or more computers or other processors, perform methods that implement the various embodiments discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present disclosure as discussed above. As used herein, the term "computer-readable storage medium" encompasses only a non-transitory computer-readable medium that can be considered to be a manufacture (i.e., article of manufacture) or a machine. Alternatively or additionally, the disclosure may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

ADDITIONAL EMBODIMENTS

The present disclosure further provide embodiments described in the following numbered paragraphs:

1. A container comprising:
- a base including a base internal volume, wherein the base has a base longitudinal length; and
- a cap configured to removably couple to the base, wherein the cap includes a cap internal volume and an external cap key, the external cap key configured to engage with a gripper of a decapper for removal of the cap off of the base,
- wherein the cap internal volume is greater than the base internal volume, and wherein the cap has a cap longitudinal length, and
- wherein the cap longitudinal length is greater than the base longitudinal length.

2. The container of paragraph 1, wherein the cap longitudinal length is 2 to 4 times greater than the base longitudinal length.

3. The container of any one of paragraphs 1-2, further comprising a watertight seal configured to seal the container when the base and the cap are coupled together.

4. The container of paragraph 3, wherein the base includes a radial projection, and wherein the cap includes a channel configured to receive the radial projection, wherein rotation of the base relative to the cap while the radial projection is disposed in the channel is configured to form the watertight seal between the base and the cap.

5. The container of any one of paragraphs 1-2, wherein the base includes base threads, and wherein the cap includes cap threads configured to threadedly engage the base threads.

6. The container of any one of paragraphs 1-2, wherein the base includes a radial projection, and wherein the cap includes a channel configured to receive the radial projection.

7. The container of any one of paragraphs 1-2, wherein the cap includes a radial projection, and wherein the base includes a channel configured to receive the radial projection.

8. The container of any one of paragraphs 1-7, wherein at least a portion of the container is translucent.

9. The container of paragraph 8, wherein the cap is translucent.

10. The container of paragraph 8, wherein the base is translucent.

11. The container of paragraph 8, wherein the cap includes a hydrochromic indicator disposed in the cap internal volume, wherein the hydrochromic indicator is configured to irreversibly change color when exposed to liquid.

12. The container of paragraph 11, wherein the hydrochromic indicator is configured to irreversibly change color when exposed to liquid internal to the container.

13. The container of any one of paragraphs 1-7, further comprising a hydrochromic indicator, wherein the hydrochromic indicator is configured to irreversibly change color when exposed to liquid.

14. The container of paragraph 13, wherein the hydrochromic indicator is disposed in the base.

15. The container of any one of paragraphs 1-14, further comprising a desiccant removably disposed in the cap internal volume.

16. The container of any one of paragraphs 1-15, further comprising an identification marker disposed on an exterior surface of the base.

17. The container of any one of paragraphs 1-16, wherein the external cap key is configured to engage the gripper to transmit torque between the cap and the gripper.

18. The container of any one of paragraphs 1-17, further comprising an environmental control configured to maintain an environmental condition of the cap internal volume and the base internal volume.

19. The container of paragraph 18, wherein the environmental control is a cold pack.

20. A container comprising:
- a base including a base internal volume and an external base key;
- a cap configured to receive and removably couple to the base, wherein the cap includes a cap internal volume and an external cap key; and
- a closure configured to couple the base to the cap, wherein the closure includes a radial projection and a channel configured to receive the radial projection, wherein the channel terminates in a closed end,
- the closure further including a protrusion, the protrusion being spaced from the closed end, wherein sliding of the radial projection past the protrusion produces auditory and/or tactile feedback, and
- wherein the base and the cap mate together to form a watertight seal.

21. The container of paragraph 20, wherein the auditory and/or tactile feedback comprises a click.

22. The container of any one of paragraphs 20-21, wherein the channel includes a first portion and a second portion, the first portion being configured to receive the radial projection in a first longitudinal direction and the second portion extending in a circumferential direction and terminating in the closed end.

23. The container of any one of paragraphs 20-22, wherein the protrusion and the closed end define a recess configured to retain the radial projection in the channel and inhibit relative longitudinal movement of the cap and the base.

24. The container of any one of paragraphs 20-23, wherein the channel is disposed on the cap and the radial projection is disposed on the base.

25. The container of any one of paragraphs 20-23, wherein the channel is disposed on the base and the radial projection is disposed on the cap.

26. The container of any one of paragraphs 20-25, wherein the cap internal volume is greater than the base internal volume.

27. The container of any one of paragraphs 20-26, wherein when the radial projection is received in the channel, relative rotation of the base and the cap moves the base further into the cap.

28. The container of paragraph 27, wherein the radial projection includes a first cam surface, wherein the channel includes a second cam surface configured to slidingly engage the first cam surface.

29. The container of any one of paragraphs 20-28, wherein the closure includes a second radial projection, a third radial projection, and a fourth radial projection, and wherein the closure includes a second channel, a third channel, and a fourth channel.

30 The container of any one of paragraphs 20-29, wherein at least a portion of the container is translucent.

31. The container of paragraph 30, wherein the cap includes a moisture indicator, wherein the moisture indicator is configured to change from a first state to a second state when moisture is detected.

32. The container of paragraph 31, wherein the moisture indicator comprises a hydrochromic indicator, wherein the hydrochromic indicator is configured to irreversibly change color when exposed to liquid.

33. The container of any one of paragraphs 20-32, further comprising a desiccant removably disposed in the cap internal volume.

34. The container of any one of paragraphs 20-32, further comprising an environmental control configured to maintain an environmental condition of the cap internal volume and the base internal volume.

35. The container of paragraph 34, wherein the environmental control is a cold pack.

36. A container comprising:

a base including a base internal volume and an external base key;

a cap configured to receive and removably couple to the base, wherein the cap includes a cap internal volume and an external cap key; and a closure configured to couple the base to the cap, wherein the closure forms a watertight seal when the base is coupled to the cap, wherein the base internal volume and the cap internal volume combine to form an internal volume when the base is coupled to the cap, and wherein the internal volume is configured to receive and enclose a sample vial.

37. The container of paragraph 36, wherein the closure includes a radial projection and a channel configured to receive the radial projection, wherein the channel terminates in a closed end.

38. The container of any one of paragraphs 36-37, wherein the closure is a threaded closure.

39. The container of paragraph 38, wherein the base includes base threads, and wherein the cap includes cap threads configured to threadedly engage the base threads.

40. The container of any one of paragraphs 36-39, wherein at least a portion of the container is translucent.

41. The container of paragraph 40, wherein the cap is translucent.

42. The container of paragraph 40, wherein the base is translucent.

43. The container of any one of paragraphs 36-42, further comprising a hydrochromic indicator, wherein the hydrochromic indicator is configured to irreversibly change color when exposed to liquid.

44. The container of any one of paragraphs 36-43, further comprising a desiccant removably disposed in the cap internal volume.

45. The container of any one of paragraphs 36-44, further comprising an identification marker disposed on an exterior surface of the base.

46. The container of any one of paragraphs 36-45, wherein the external cap key is configured to engage a gripper to transmit torque between the cap and the gripper.

47. The container of any one of paragraphs 36-46, further comprising an environmental control configured to maintain an environmental condition of the cap internal volume and the base internal volume.

48. The container of paragraph 47, wherein the environmental control is a cold pack.

49. A method of detecting leakage of a sample vial inside of a container, wherein the container includes a base and a cap, the method comprising:

imaging an internal volume of the container through a wall of the container with an imaging sensor, wherein the internal volume contains the sample vial;

detecting, based on the imaging, a state of an indicator disposed inside of the internal volume, wherein the indicator has a first state and a second state wherein exposing the indicator to liquid causes the indicator to change from the first state to the second state;

upon detecting the first state of the indicator, removing the cap from the base with a gripper; and upon detecting the second state of the indicator, allowing the cap to remain on the base.

50. The method of paragraph 49, wherein the indicator comprises a hydrochromic indicator, and in the first state, the hydrochromic indicator is a first color, and in the second state, the hydrochromic indicator is a second color.

51. The method of paragraph 49, wherein the wall of the container is a wall of the cap.

52. The method of any one of paragraphs 49-51, wherein the indicator is a hydrochromic dye.

53. The method of paragraph 49, wherein the indicator is a hydrochromic coating disposed on an inner wall of the container.

54. The method of paragraph 49, wherein the indicator is a liquid contact indicator.

55. The method of any one of paragraphs 49-54, further comprising absorbing liquid in the internal volume with a desiccant disposed in the internal volume.

56. The method of any one of paragraphs 49-54, wherein removing the cap from the base includes rotating the cap relative to the base.

57. The method of any one of paragraphs 49-56, further comprising reading an identification marker disposed on an exterior surface of the base, and further comprising updating a status of the container in a database after detecting the second state of the indicator.

58. The method of any one of paragraphs 49-57, further comprising removing the container from a conveyor and placing the container in a quarantine receptacle after detecting the second state of the indicator.

59. The method of any one of paragraphs 49-58, wherein at least a portion of the container is translucent.

60. A method of removing a sample vial from a container, wherein the container includes a base and a cap, the method comprising:

removing the cap from the base to expose the sample vial, the sample vial being supported by the base;

imaging a portion of the sample vial with an imaging sensor;

determining an orientation state of the sample vial, wherein the sample vial has an upright orientation where a vial cap of the sample vial is above a bottom portion of the sample vial, and wherein the sample vial has an inverted orientation where the bottom portion of the sample vial is above the vial cap;

grasping the sample vial with a first gripper;

lifting the sample vial out of the base with the first gripper; and upon detecting the inverted orientation, rotating the sample vial from the inverted orientation to the upright orientation.

61. The method of paragraph 60, wherein the cap has a cap longitudinal length and the base has a base longitudinal length, the cap longitudinal length being greater than the base longitudinal length, wherein the sample vial has a vial longitudinal length greater than the base longitudinal length.

62. The method of any one of paragraphs 60-61, wherein the portion of the sample vial extends out of the base.

63. The method of any one of paragraphs 60-62, further comprising reading an identification marker disposed on an external surface of the base.

64 The method of paragraph 63, further comprising:

detecting a height of the sample vial relative to the first gripper; and grasping the sample vial with a second gripper.

65. The method of paragraph 64, further comprising placing the sample vial in a rack based on the identification marker with the second gripper.

66. The method of paragraph 63, wherein the identification marker is a QR code.

67. The method of paragraph 66, wherein the QR code provides information regarding a type of sample contained in the sample vial to a reader.

68. The method of any one of paragraphs 60-67, wherein removing the cap from the base includes rotating the cap relative to the base.

69. A container retrieval system for retrieving sample vials from containers, the containers including a container comprising a base, a cap, an internal volume, the internal volume having both an indicator and a sample vial disposed therein, the system comprising:

a conveyor configured to support and move the container;

an imaging sensor configured to obtain an image of the indicator through a wall of the container for detecting a state of the indicator, wherein at least a part of the wall is translucent; and a processor configured to:

obtain the image of the indicator obtained by the imaging sensor;

detect, by processing the image, the state of the indicator; and determine, based on the detected state of the indicator, whether the indicator was exposed to liquid.

70. The container retrieval system of paragraph 69, wherein the indicator comprises a hydrochromic indicator configured to change from a first color to a second color when exposed to liquid.

71. The container retrieval system of any one of paragraphs 69-70, wherein the indicator is configured to irreversibly change color when exposed to liquid.

72. The container retrieval system of any one of paragraphs 69-70, wherein the indicator is a hydrochromic dye.

73. The container retrieval system of any one of paragraphs 69-70, wherein the indicator is a hydrochromic coating disposed on an inner wall of the cap.

74. The container retrieval system of any one of paragraphs 69-70, wherein the indicator is a liquid contact indicator.

75. The container retrieval system of any one of any one of paragraphs 69-70, wherein the cap includes a cap internal volume greater than a base internal volume of the base.

76. The container retrieval system of any one of paragraphs 69-75, further comprising an identification marker disposed on an exterior surface of the base.

77. The container retrieval system of any one of paragraphs 69-76, further comprising a desiccant removably disposed in the internal volume.

78. The container retrieval system of any one of paragraphs 69-77, wherein the container includes a watertight seal configured to seal the internal volume.

79. A system for retrieving a sample vial from a container, the container comprising a base, a cap, and an internal volume, and a sample vial disposed in the internal volume, the system comprising:

a conveyor configured to support and move the container by the base, wherein the conveyor inhibits rotation of the base;

a first gripper configured to remove the cap from the base by rotating the cap relative to the base;

an imaging sensor configured to determine an orientation state of the sample vial, wherein the sample vial has an upright orientation where a vial cap of the sample vial is above a bottom portion of the sample vial, and wherein the sample vial has an inverted orientation where the bottom portion of the sample vial is above the vial cap; and a second gripper configured to grasp the sample vial and lift the sample vial out of the base, and wherein the second gripper is configured to rotate the sample vial from the inverted orientation to the upright orientation.

80. The system of paragraph 79, wherein the cap has a cap longitudinal length greater than a base longitudinal length of the base.

81. The system of paragraph 80, wherein the sample vial has a vial longitudinal length greater than the base longitudinal length.

82. The system of any one of paragraphs 79-81, further comprising:

an identification marker disposed on an exterior surface of the base; and a second imaging sensor configured to observe the identification marker.

83. The system of any one of paragraphs 79-82, further comprising a height sensor configured to detect a height of the sample vial relative to the second gripper.

84. The system of paragraph 83, further comprising a third gripper configured to grasp the sample vial and remove the sample vial from the second gripper.

85. The system of any one of paragraphs 79-84, wherein the cap includes a cap internal volume greater than a base internal volume of the base.

86. The system of any one of paragraphs 79-85, wherein at least a portion of the container is translucent.

87 The system of any one of paragraphs 79-86, wherein the cap includes a hydrochromic indicator disposed in the internal volume, wherein the hydrochromic indicator is configured to irreversibly change color when exposed to liquid.

88. The system of any one of paragraphs 79-87, further comprising a desiccant removably disposed in the internal volume.

89 The system of any one of paragraphs 79-88, further comprising the container and the sample vial, the container comprising a base, a cap and an internal volume.

90. A system for retrieving sample vials from a plurality of containers, each container of the plurality of containers comprising a base, a cap, and an internal volume, and a sample vial disposed in the internal volume, the system comprising:

- a hopper configured to receive the plurality of containers;
- a receiver configured to receive a first container from the hopper, wherein the receiver is configured to orient the first container in a first orientation, wherein in the first orientation the cap is positioned above the base;
- a conveyor configured to receive the first container from the receiver, wherein the conveyor is configured to support and move the first container by the base, wherein the conveyor inhibits rotation of the base; and
- a first gripper configured to remove the cap from the base by rotating the cap relative to the base.

91. The system of paragraph 90, wherein the receiver is a transporter track.

92. The system of paragraph 90, wherein the receiver is a second gripper.

93. The system of any one of paragraphs 90-92, wherein the cap has a cap longitudinal length greater than a base longitudinal length of the base.

94. The system of paragraph 93, wherein the sample vial has a vial longitudinal length greater than the base longitudinal length.

95. The system of any one of paragraphs 90-94, further comprising:

- an identification marker disposed on an exterior surface of the base; and
- an imaging sensor configured to observe the identification marker.

96. The system of any one of paragraphs 90-95, wherein the cap includes a cap internal volume greater than a base internal volume of the base.

97 The system of any one of paragraphs 90-96, wherein at least a portion of each container of the plurality of containers is translucent.

98. The system of paragraph 97, wherein the cap includes a hydrochromic indicator disposed in the internal volume, wherein the hydrochromic indicator is configured to irreversibly change color when exposed to liquid.

99. The system of any one of paragraphs 90-97, further comprising the plurality of containers and the first container.

100. A method of removing sample vials from a plurality of containers, wherein each container of the plurality of containers includes a base and a cap, the method comprising:

- placing the plurality of containers in a hopper;
- transferring a first container of the plurality of containers from the hopper to a receiver;
- orienting the first container to a first orientation where the cap is positioned above the base with the receiver;
- transferring the first container to a conveyor, wherein the conveyor supports the first container by the base; and
- removing the cap from the base to expose a sample vial disposed in the first container, the sample vial being supported by the base.

101. The method of paragraph 100, wherein the conveyor inhibits rotation of the base.

102. The method of any one of paragraphs 100-101, wherein the cap has a cap longitudinal length and the base has a base longitudinal length, the cap longitudinal length being greater than the base longitudinal length, wherein the sample vials have a vial longitudinal length greater than the base longitudinal length.

103. The method of any one of paragraphs 100-102, wherein the receiver is a transporter track.

104. The method of any one of paragraphs 100-103, wherein the receiver is a first gripper configured to grasp the first container.

105. The method of any one of any one of paragraphs 100-104, wherein a portion of the sample vial extends out of the base.

106. The method of any one of any one of paragraphs 100-105, further comprising reading an identification marker disposed on an external surface of the base.

107. The method of paragraph 106, wherein the identification marker is a QR code.

108. The method of paragraph 107, wherein the QR code provides information regarding a type of sample contained in the sample vial to a reader.

109. The method of any one of paragraphs 100-108, wherein removing the cap from the base includes rotating the cap relative to the base.

110. A computer program comprising computer executable instructions which when executed by a processor cause the processor to perform the steps of any one of the preceding methods of any one of paragraphs 49-68 and 100-109.

111. The computer program of paragraph 110, wherein the computer program is embodied in a computer readable medium.

112. A method of assembling a container, wherein the container includes a base and a cap, the method comprising:

- placing a sample vial in the base with an automated assembly system;
- placing the cap on the base with the automated assembly system; and
- rotating the cap relative to the base with the automated assembly system to couple the cap to the base.

113. The method of paragraph 112, further comprising placing a hydrochromic indicator in the base with the automated assembly system.

114. The method of paragraph 112, further comprising placing an environmental control in the base with the automated assembly system.

115. The method of any one of paragraphs 112-114, further comprising imaging the container with an imaging sensor.

116. The method of paragraph 115, further comprising:

- detecting a closed state or open state of the container based on the image from the imaging sensor;
- upon detecting the open state of the container, moving the container off of a conveyor track; and
- upon detecting the closed state of the container, allowing the container to remain on the conveyor track.

117. The method of any one of paragraphs 112-116, wherein rotating the cap relative to the base includes:
engaging an external base key with a base receptacle; and
engaging an external cap key with a gripper.

118. The method of any one of paragraphs 112-117, wherein the base has a base longitudinal length, the cap has a cap longitudinal length, and wherein the cap longitudinal length is greater than the base longitudinal length.

119. The method of any one of paragraphs 112-118, wherein placing a sample vial in the base includes placing the sample vial in the base with a first gripper, wherein placing the cap on the base includes placing the cap of the base with a second gripper, and wherein rotating the cap relative to the base includes rotating the cap with the second gripper.

120. A method of assembling a container, wherein the container includes a base and a cap, the method comprising:
placing an object in the base with an automated assembly system;
placing the cap on the base with the automated assembly system; and
rotating the cap relative to the base with the automated assembly system to couple the cap to the base, wherein rotating the cap relative to the base includes:
engaging an external base key with a base receptacle, and
engaging an external cap key with a gripper.

121. The method of paragraph 120, further comprising placing a hydrochromic indicator in the base with the automated assembly system.

122. The method of paragraph 120, further comprising placing an environmental control in the base with the automated assembly system.

123. The method of any one of paragraphs 120-122, further comprising imaging the container with an imaging sensor.

124. The method of paragraph 123, further comprising:
detecting a closed state or open state of the container based on the image from the imaging sensor;
upon detecting the open state of the container, moving the container off of a conveyor track; and
upon detecting the closed state of the container, allowing the container to remain on the conveyor track.

125. The method of any one of paragraphs 120-124, wherein the base has a base longitudinal length, the cap has a cap longitudinal length, and wherein the cap longitudinal length is greater than the base longitudinal length.

126. The method of any one of paragraphs 120-125, wherein the gripper is a first gripper, wherein placing a sample vial in the base includes placing the sample vial in the base with a second gripper, wherein placing the cap on the base includes placing the cap of the base with the first gripper, and wherein rotating the cap relative to the base includes rotating the cap with the first gripper.

127. A computer program comprising computer executable instructions which when executed by a processor cause the processor to perform the steps of any one of the preceding methods of any one of paragraphs 112-126.

128. The computer program of paragraph 127, wherein the computer program is embodied in a computer readable medium.

129. The container of any one of paragraphs 11-14, wherein the hydrochromic indicator includes a desiccant configured to absorb liquid internal to the container.

130. The container of paragraph 15, wherein the desiccant further comprises a hydrochromic indicator configured to irreversibly change color when exposed to liquid, a solution, or other substance.

131. The container of paragraph 31, wherein the moisture indicator includes a desiccant configured to absorb liquid internal to the container.

132. The container of paragraph 33, the desiccant further comprises a hydrochromic indicator configured to irreversibly change color when exposed to liquid, a solution, or other substance.

133. The container of paragraph 43, wherein the hydrochromic indicator includes a desiccant configured to absorb liquid internal to the container.

134. The container of paragraph 44, the desiccant further comprises a hydrochromic indicator configured to irreversibly change color when exposed to liquid, a solution, or other substance.

135. The method of any one of paragraphs 49-53, wherein the indicator includes a desiccant configured to absorb liquid internal to the container.

136. The container retrieval system of any one of paragraphs 69-73, wherein the indicator includes a desiccant configured to absorb liquid.

137. The system of paragraph 87, wherein the hydrochromic indicator includes a desiccant configured to absorb liquid.

138. The system of paragraph 88, wherein the desiccant and the hydrochromic indicator are combined.

139. The system of paragraph 98, wherein the hydrochromic indicator includes a desiccant configured to absorb liquid internal to the internal volume.

140. The method of paragraph 112, wherein the indicator includes a desiccant configured to absorb liquid internal to the container.

141. The method of paragraph 121, wherein the hydrochromic indicator includes a desiccant configured to absorb liquid.

142. A system for retrieving sample vials from a plurality of containers, each container of the plurality of containers comprising a base, a cap, and an internal volume, and a sample vial disposed in the internal volume, the system comprising:
a conveyor configured to receive and move the plurality of containers;
at least one imaging sensor configured to observe at least one characteristic of each container of the plurality of containers disposed on the conveyor;
a first gripper configured to remove a first container of the plurality of containers from the conveyor;
a hopper configured to receive the plurality of containers from the conveyor, wherein the hopper is configured to vibrate containers disposed in the hopper; and
a second gripper configured to remove a second container of the plurality of containers from the hopper.

143. The system of paragraph 142, wherein the at least one characteristic is selected from a group of moisture disposed in or on the first container or the second container and a closed status of the first container or the second container.

144. The system of any of paragraphs 142-143, wherein each container of the plurality of containers includes a first line disposed on the base and a second line disposed on the cap, wherein alignment of the first line and the second line indicates the closed status of a corresponding container.

145. The system of any of paragraphs 142-144, wherein the first gripper is configured to remove the first container of the plurality of containers from the conveyor based on a detection of the at least one characteristic by the at least one imaging sensor.

146. The system of any of paragraphs 142-145, wherein the second gripper is configured to remove the second container of the plurality of containers from the hopper based on a lack of detection of the at least one characteristic by the at least one imaging sensor.

147. A method of operating a container accessioning system, the method comprising:

imaging an internal volume of a sample vial;

determining a characteristic of a sample disposed within the internal volume of the sample vial;

determining if the characteristic of the sample falls within an expected range;

upon determining the characteristic falls within the expected range, accessioning the sample vial; and upon determining the characteristic falls outside of the expected range, updating a status of the sample vial in a database.

148. The method of paragraph 147, wherein accessioning the sample vial comprises:

removing the sample vial from a container internal volume with a gripper; and removing a sample vial cap from the sample vial.

149. The method of any of paragraphs 147-148, wherein the characteristic is a viscosity of the sample.

150. The method of any of paragraphs 147-148, wherein the characteristic is a consistency of the sample.

151. The method of any of paragraphs 147-148, wherein the characteristic is a color of the sample.

152. The method of any of paragraphs 147-148, wherein the characteristic is a volume of the sample.

153. The method of any of paragraphs 147-152, further comprising, upon determining the characteristic falls outside of the expected range, moving the sample vial to a quarantine area.

154. At least one non-transitory computer-readable storage medium storing programming instructions that, when executed by at least one processor, causes the at least one processor to perform the method of any of paragraphs 49-68, 100-109, 112-126, 135, 140-141, and 147-153.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A system for retrieving sample vials from a plurality of containers, each container of the plurality of containers comprising a base, a cap, and an internal volume, and a sample vial disposed in the internal volume, the system comprising:

a hopper configured to receive the plurality of containers;

a receiver configured to receive a first container from the hopper, wherein the receiver is configured to orient the first container in a first orientation, wherein in the first orientation the cap is positioned above the base;

a conveyor configured to receive the first container from the receiver, wherein the conveyor is configured to support and move the first container by the base, wherein the conveyor inhibits rotation of the base;

a first gripper configured to remove the cap from the base by rotating the cap relative to the base; and a processor configured to:

place a plurality of containers in a hopper, wherein each container of the plurality of containers includes a base and a cap;

transfer a first container of the plurality of containers from the hopper to a receiver:

orient the first container to a first orientation where the cap is positioned above the base with the receiver:

transfer the first container to a conveyor, wherein the conveyor supports the first container by the base, and wherein the conveyor inhibits rotation of the base; and remove the cap from the base to expose a sample vial disposed in the first container, the sample vial being supported by the base, wherein the cap has a cap longitudinal length and the base has a base longitudinal length, the cap longitudinal length being greater than the base longitudinal length, wherein the sample vials have a vial longitudinal length greater than the base longitudinal length.

2. The system of claim 1, wherein the receiver is a transporter track.

3. The system of claim 1, wherein the receiver is a second gripper.

4. The system of claim 1, further comprising:

an identification marker disposed on an exterior surface of the base; and an imaging sensor configured to observe the identification marker.

5. The system of claim 1, wherein the cap includes a cap internal volume greater than a base internal volume of the base.

6. The system of claim 1, wherein at least a portion of each container of the plurality of containers is translucent.

7. The system of claim 6, wherein the cap includes a hydrochromic indicator disposed in the internal volume, wherein the hydrochromic indicator is configured to irreversibly change color when exposed to liquid.

8. The system of claim 1, further comprising the plurality of containers and the first container.

9. A method of removing sample vials from a plurality of containers, wherein each container of the plurality of containers includes a base and a cap, the method comprising:

placing the plurality of containers in a hopper;

transferring a first container of the plurality of containers from the hopper to a receiver;

orienting the first container to a first orientation where the cap is positioned above the base with the receiver;

transferring the first container to a conveyor, wherein the conveyor supports the first container by the base, and wherein the conveyor inhibits rotation of the base; and removing the cap from the base to expose a sample vial disposed in the first container, the sample vial being supported by the base, wherein the cap has a cap longitudinal length and the base has a base longitudinal length, the cap longitudinal length being greater than the base longitudinal length, wherein the sample vials have a vial longitudinal length greater than the base longitudinal length.

10. The method of claim 9, wherein a portion of the sample vial extends out of the base.

11. The method of claim 9, further comprising reading an identification marker disposed on an external surface of the base.

12. The method of claim 11, wherein the identification marker is a QR code, and wherein the QR code provides information regarding a type of sample contained in the sample vial to a reader.

13. The method of claim 9, wherein removing the cap from the base includes rotating the cap relative to the base.

14. The method of claim 11, wherein the identification marker is a QR code.

15. The method of claim 9, wherein the receiver is a transporter track.

16. The method of claim 9, wherein the receiver is a first gripper configured to grasp the first container.

17. At least one non-transitory computer-readable storage medium storing programming instructions that, when executed by at least one processor, cause the at least one processor to:

place a plurality of containers in a hopper, wherein each container of the plurality of containers includes a base and a cap;

transfer a first container of the plurality of containers from the hopper to a receiver;

orient the first container to a first orientation where the cap is positioned above the base with the receiver;

transfer the first container to a conveyor, wherein the conveyor supports the first container by the base, and wherein the conveyor inhibits rotation of the base; and remove the cap from the base to expose a sample vial disposed in the first container, the sample vial being supported by the base, wherein the cap has a cap longitudinal length and the base has a base longitudinal length, the cap longitudinal length being greater than the base longitudinal length, wherein the sample vials have a vial longitudinal length greater than the base longitudinal length.

* * * * *